US012799263B2

(12) United States Patent
Jebors et al.

(10) Patent No.: US 12,799,263 B2
(45) Date of Patent: Nov. 17, 2026

(54) POLYMER COMPOUND COMPRISING PENDENT PEPTIDES, METHOD FOR PREPARING SAME AND USES THEREOF

(71) Applicant: GENEPEP, Saint Jean de Vedas (FR)

(72) Inventors: Saïd Jebors, Montpellier (FR); Karine Puget, Saint Jean de Vedas (FR)

(73) Assignee: GENEPEP, Saint Jean de Vedas (FR)

( * ) Notice: Subject to any disclaimer, the term of this patent is extended or adjusted under 35 U.S.C. 154(b) by 526 days.

(21) Appl. No.: 18/266,834

(22) PCT Filed: Dec. 13, 2021

(86) PCT No.: PCT/EP2021/085532
§ 371 (c)(1),
(2) Date: Jun. 13, 2023

(87) PCT Pub. No.: WO2022/128940
PCT Pub. Date: Jun. 23, 2022

(65) Prior Publication Data

US 2024/0084068 A1 Mar. 14, 2024

(30) Foreign Application Priority Data

Dec. 14, 2020 (EP) .................................... 20306561

(51) Int. Cl.

| | |
|---|---|
| ***C08G 18/64*** | (2006.01) |
| ***C07K 5/072*** | (2006.01) |
| ***C07K 7/06*** | (2006.01) |
| ***C08G 18/08*** | (2006.01) |
| ***C08G 18/24*** | (2006.01) |
| ***C08G 18/32*** | (2006.01) |
| ***C08G 18/48*** | (2006.01) |
| ***C08G 18/65*** | (2006.01) |
| ***C08G 18/66*** | (2006.01) |
| ***C08G 18/76*** | (2006.01) |
| ***C08G 63/91*** | (2006.01) |

(52) U.S. Cl.
CPC ...... *C08G 18/6446* (2013.01); *C07K 5/06095* (2013.01); *C07K 7/06* (2013.01); *C08G 18/0852* (2013.01); *C08G 18/246* (2013.01); *C08G 18/3206* (2013.01); *C08G 18/3215* (2013.01); *C08G 18/4854* (2013.01); *C08G 18/6511* (2013.01); *C08G 18/6674* (2013.01); *C08G 18/7671* (2013.01); *C08G 63/916* (2013.01)

(58) Field of Classification Search
CPC ............ C08G 18/6446; C08G 18/0852; C08G 18/246; C08G 18/3206; C08G 18/3215; C08G 18/4854; C08G 18/6511; C08G 18/6674; C08G 18/7671; C08G 63/916; C08G 69/26; C07K 5/06095; C07K 7/06; C07K 5/06078; C07K 5/0806; C07K 5/1016; C07K 5/1019; C08L 75/04
See application file for complete search history.

(56) References Cited

PUBLICATIONS

Written Opinion in International Application No. PCT/EP2021/085532, Apr. 8, 2022, pp. 1-8.

(Continued)

*Primary Examiner* — Doris L Lee
(74) *Attorney, Agent, or Firm* — SALIWANCHIK, LLOYD & EISENSCHENK

(57) ABSTRACT

The present invention relates to a polymer compound comprising pendent peptides, to a method for preparing same and to the use thereof in the manufacture of a material or an article.

7 Claims, 4 Drawing Sheets

(56) References Cited

PUBLICATIONS

Gokhale, S. et al. "A Library of Multifunctional Polyesters with "Peptide-Like" Pendant Functional Groups" *Biomacromolecules*, Jun. 24, 2013, pp. 2489-2493, vol. 14, No. 8.
Lin, H.-B. et al. "Synthesis, surface, and cell-adhesion properties of polyurethanes containing covalently grafted RGD-peptides" *Journal of Biomedical Materials Research*, 1994, pp. 329-342, vol. 28, No. 3.
Wu, G. et al. "Elastic polyurethane bearing pendant TGF-β1 affinity peptide for potential tissue engineering applications" *Materials Science & Engineering C*, 2018, pp. 67-77, vol. 83.
Andersson, L. et al. "Poly(ethylene glycol)-Poly(ester-carbonate) Block Copolymers Carrying PEG-Peptidyl-Doxorubicin Pendant Side Chains: Synthesis and Evaluation as Anticancer Conjugates" *Biomacromolecules*, 2005, pp. 914-926, vol. 6, No. 2.

Route D

Route E

Route F

POLYMER COMPOUND COMPRISING PENDENT PEPTIDES, METHOD FOR PREPARING SAME AND USES THEREOF

CROSS-REFERENCE TO RELATED APPLICATION

This application is the U.S. national stage application of International Patent Application No. PCT/EP2021/085532, filed Dec. 13, 2021.

SUBJECT MATTER OF THE INVENTION

The present invention relates to a polymer compound with pendant peptides, a method for preparing same and uses thereof in the manufacture of a material or an article.

BACKGROUND OF THE INVENTION

Polyesters and polyamides are among the polymers most used in everyday life. These polymers, which are mainly encountered in the form of fibers, in particular display great durability, strength and stability, properties that are essential in many applications. To impart certain properties that are required for specific applications, it is generally necessary to insert particular functional groups, sometimes also in particular positions of the polymer and in particular proportions. In particular, in the biomedical field, the formation of polymers modified by the introduction of bioactive molecules has aroused interest in the scientific community in recent years. Depending on the method elaborated, the peptides added to the polymer may be incorporated within the actual structure of the polymer, or may just be adsorbed on its surface.

For example, patent U.S. Pat. No. 7,709,601 describes a method in which functionalization of the polymer with the peptides takes place after polymerization, and this then results in adsorption of the peptides on the surface of the polymer.

Patent application WO 2017/098018 describes a method of interfacial polymerization of an acyl dihalide with one or more amino acids or peptides performing the role of a diamine, or else with a diamine substituted with a peptide. Polyamides having peptides incorporated actually within the polymer backbone, or else pendant, and having $—CO_2H$ and/or $—NH_2$ ends, are obtained by said method. This type of polymer is particularly useful for making biomaterials, in particular with antibacterial properties. It has been found, however, that said method of interfacial polymerization cannot provide a large variety of polymers, and is difficult to implement industrially. Therefore there is still a real need to develop new polymers bearing peptides, and that may be obtained by a simple method allowing good control of the distribution of the peptides along the polymer chain.

SUMMARY OF THE INVENTION

In this context, the inventors have developed a polymer compound, on which there are one or more pendant peptides. The structure of the polymer compound may be likened to a comb structure, in which the polymer backbone is linear and consists of repeat units, and each "branch" or "tooth" attached to the backbone consists of a peptide. The method elaborated by the inventors consists of mixing, in a molten medium, monomers substituted with a peptide, and unsubstituted monomers, in conditions allowing homogeneous and/or controlled distribution of the pendant peptides on the polymer thus obtained. A large variety of polymers could be prepared by this method, in particular polyamides, polyesters and polyurethanes. The polymer compound obtained offers advantages as a component used in the manufacture of a (bio)material or of an article, in particular with antibacterial properties.

The invention therefore relates to a polymer compound comprising:

repeat units of formula (I):

(I)

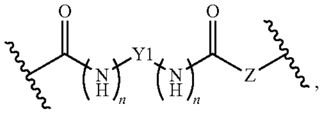

in which n has a value of 0 or 1;

Y1 represents a radical selected from a $(C_1-C_{12})$alkyl, an aryl and an aryl-$(C_1-C_{12})$alkaryl; and Z represents a radical selected from:

a group represented by the following formula (Ia):

(Ia)

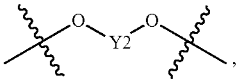

in which Y2 represents a $(C_1-C_{12})$alkyl, aryl, or polyalkylene glycol; and a group represented by the following formula (Ib):

(Ib)

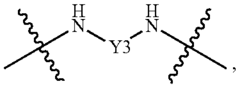

in which Y3 represents a $(C_1-C_{12})$alkyl, aryl or polyalkylene glycol;

and in which at least one of Y1, Y2, and Y3 is joined to a peptide residue via a functional residue, the functional residue and the peptide residue optionally being separated by a spacer fragment;

and repeat units of formula (II):

(II)

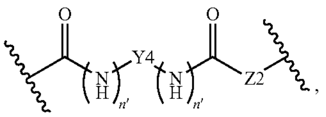

in which n' has a value of 0 or 1;

Y4 represents a radical selected from a $(C_1-C_{12})$alkyl, an aryl and an aryl-$(C_1-C_{12})$alkaryl; and Z2 represents a radical selected from:

a group represented by the following formula (IIa):

(IIa)

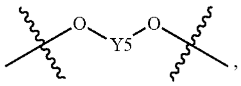

in which Y5 represents a ($C_1$-$C_{12}$)alkyl, aryl, or polyalkylene glycol; and a group represented by the following formula (IIb):

(IIb)

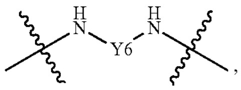

in which Y6 represents a ($C_1$-$C_{12}$)alkyl, aryl, or polyalkylene glycol, provided that when n and n' have a value of 0 and Y3 is joined to a peptide residue via a functional residue, the polymer has at least one end of formula (E10) or (E40):

(E10)

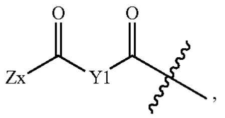

(E40)

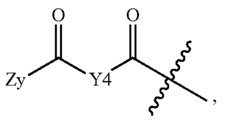

in which Zx and Zy represent independently a ($C_1$-$C_{12}$) alkyl-O— or aryl-O—.

It also relates to a monomer compound represented by the following formula (III-1):

(III-1)

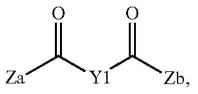

in which

Y1 represents a radical selected from a ($C_1$-$C_{12}$)alkyl, an aryl, and an aryl-($C_1$-$C_{12}$)alkaryl;

Za represents a radical selected from:

a ($C_1$-$C_{12}$)alkyl-O—, an aryl-O—, a chlorine; and, a group represented by the following formula (IIIa):

(IIIa)

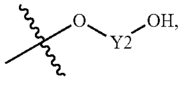

in which Y2 represents a ($C_1$-$C_{12}$)alkyl, aryl, or polyalkylene glycol; and Zb represents a radical selected from:

a ($C_1$-$C_{12}$)alkyl-O—, an aryl-O—, a chlorine;

a group represented by the following formula (IIIa):

(IIIa)

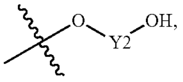

in which Y2 represents a ($C_1$-$C_{12}$)alkyl, aryl or polyalkylene glycol; and a group represented by the following formula (IIIb):

(IIIb)

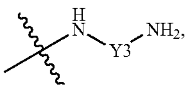

in which Y3 represents a ($C_1$-$C_{12}$)alkyl, aryl, or polyalkylene glycol;

and in which at least one of Y1, Y2, and Y3 is joined to a peptide residue via a functional residue, the functional residue and the peptide residue optionally being separated by a spacer fragment, provided that when Y3 is joined to a peptide residue via a functional residue, Za is selected from a ($C_1$-$C_{12}$) alkyl-O— and an aryl-O—.

It also relates to a monomer compound represented by the following formula (III-2):

HO—Y2-OH (III-2), in which Y2 represents a ($C_1$-$C_{12}$)alkyl, aryl or polyalkylene glycol, where Y2 is joined to a peptide residue via a functional residue, the functional residue and the peptide residue optionally being separated by a spacer fragment.

It also relates to a method for preparing a polymer compound as defined above, comprising a polycondensation reaction in a molten medium, involving:

at least one monomer compound selected from:

a monomer compound of formula Za-C(O)—Y1-C(O)-Zb, where:

Y1 represents a radical selected from a ($C_1$-$C_{12}$)alkyl, an aryl and an aryl-($C_1$-$C_{12}$)alkaryl;

Za represents a radical selected from a ($C_1$-$C_{12}$)alkyl-O—, an aryl-O—, a chlorine, and a group of formula (IIIa) where Y2 represents a ($C_1$-$C_{12}$)alkyl, aryl, or polyalkylene glycol, Zb represents a radical selected from a ($C_1$-$C_{12}$)alkyl-O—, an aryl-O—, a chlorine, a group of formula (IIIa) where Y2 represents a ($C_1$-$C_{12}$)alkyl, aryl, or polyalkylene glycol, and a group of formula (IIIb) where Y3 represents a ($C_1$-$C_{12}$)alkyl, aryl, or polyalkylene glycol;

OCN—Y1-NCO, where Y1 represents a ($C_1$-$C_{12}$)alkyl, aryl, or an aryl-($C_1$-$C_{12}$)alkaryl, HO—Y2-OH where Y2 represents a ($C_1$-$C_{12}$)alkyl, aryl, or polyalkylene glycol, and $H_2N$—Y3—$NH_2$ where Y3 represents a ($C_1$-$C_{12}$)alkyl, aryl, or polyalkylene glycol, where at least one of Y1, Y2, and Y3 is joined to a peptide residue via a functional residue, the functional residue and the peptide residue optionally being separated by a spacer fragment;

and at least one monomer compound selected from:

a monomer compound represented by the following formula (V):

(V)

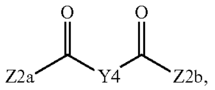

in which

Y4 represents a radical selected from a $(C_1-C_{12})$alkyl, an aryl, and an aryl-$(C_1-C_{12})$alkaryl;

Z2a represents a radical selected from:

a $(C_1-C_{12})$alkyl-O—, an aryl-O—, a chlorine; and a group represented by the following formula (Va):

(Va)

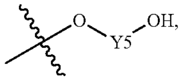

in which Y5 represents a $(C_1-C_{12})$alkyl, aryl or polyalkylene glycol; and

Z2b represents a radical selected from:

a $(C_1-C_{12})$alkyl-O—, an aryl-O—, a chlorine;

a group represented by the following formula (Va):

(Va)

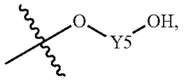

in which Y5 represents a $(C_1-C_{12})$alkyl, aryl or polyalkylene glycol; and a group represented by the following formula (Vb):

(Vb)

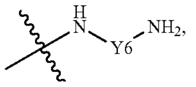

in which Y6 represents a $(C_1-C_{12})$alkyl, aryl, or polyalkylene glycol,

OCN—Y4-NCO, where Y4 represents a $(C_1-C_{12})$alkyl, aryl or aryl-$(C_1-C_{12})$alkaryl, HO—Y5-OH, where Y5 represents a $(C_1-C_{12})$alkyl, aryl, or polyalkylene glycol, and $H_2N$—Y6-$NH_2$, where Y6 represents a $(C_1-C_{12})$alkyl, aryl, or polyalkylene glycol.

It also relates to the use of a polymer compound as defined above in the manufacture of a material or an article.

It further relates to a material comprising a polymer compound as defined above.

It further relates to an article comprising a polymer compound as defined above.

DETAILED DESCRIPTION

Definitions

Figure 1:
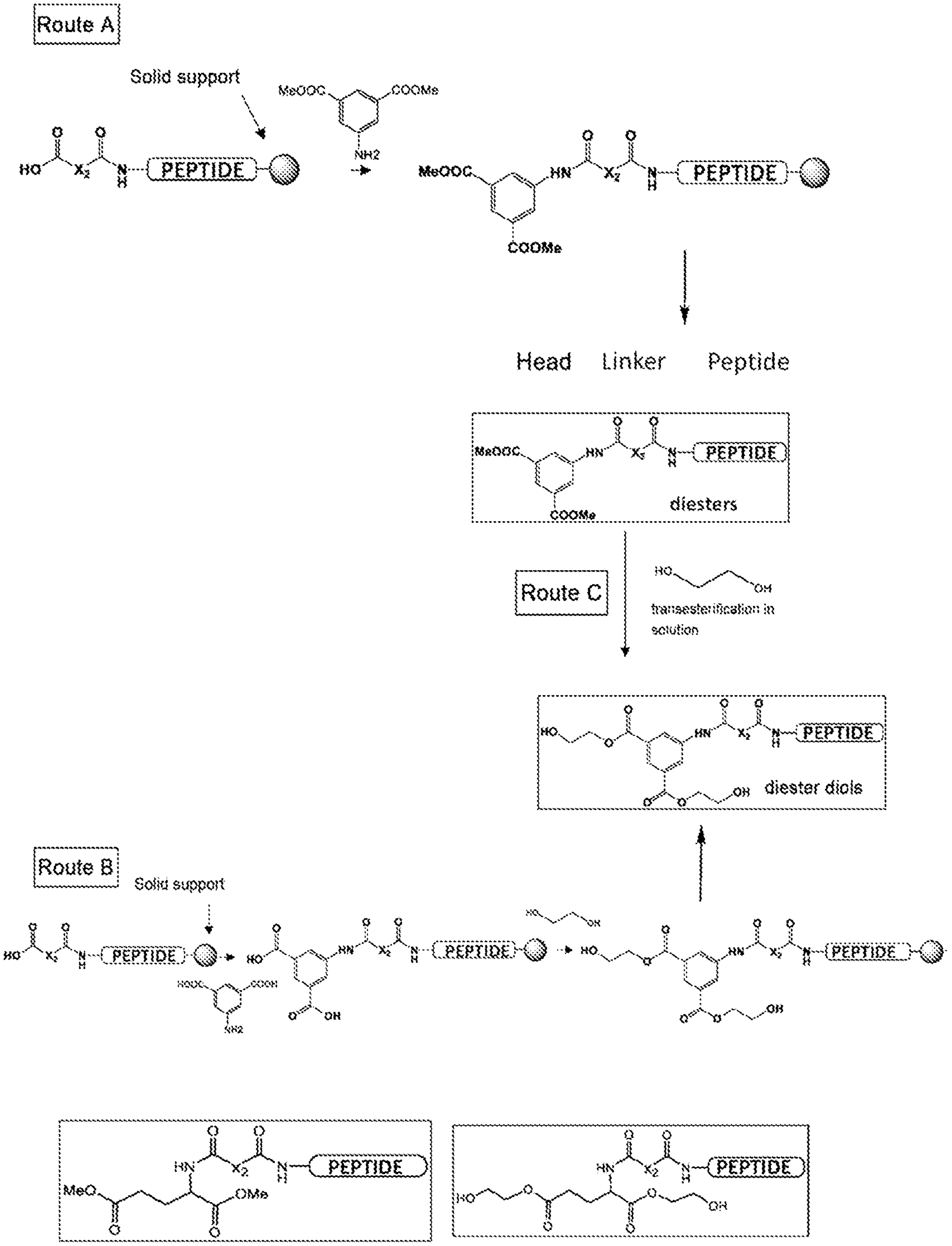
FIG. 1 shows a scheme of various syntheses of dimethyl isophthalate monomers substituted with a peptide (Route A) or bis(2-hydroxyethyl) isophthalate monomers substituted with a peptide (Routes B and C) (X2=$(C_1-C_{12})$alkyl, aryl, or polyalkylene glycol).

"Alkyl" means a saturated, linear or branched aliphatic hydrocarbon group. The expression "$(C_1-C_{12})$alkyl" denotes an alkyl containing from 1 to 12 carbon atoms, in particular a methyl, ethyl, propyl, isopropyl, butyl, isobutyl, pentyl, hexyl, heptyl, octyl, nonyl, decyl, undecyl, or dodecyl group. Examples of preferred $(C_1-C_{12})$ alkyl groups are in particular $(C_1-C_6)$alkyl groups such as methyl, ethyl, propyl, butyl, pentyl, and hexyl groups. Preferably, a $(C_1-C_{12})$alkyl group is a $(C_1-C_6)$alkyl group.

"Aryl" means an aromatic carbocyclic group with 6 to 14 ring members, mono- or polycyclic. Examples of aryl groups are phenyl and naphthyl, preferably phenyl.

"Aryl-$(C_1-C_{12})$alkaryl" means a divalent group consisting of an alkyl having 1 to 12 carbon atoms attached to two aryls, where each bond with said aryls involves the same carbon or two different carbons of the alkyl and where each of the two aryls is attached to the rest of the molecule. An aryl-$(C_1-C_{12})$alkaryl is preferably an aryl-$(C_1-C_6)$alkaryl such as the phenyl-methyl-phenyl group, which may in particular be represented as follows:

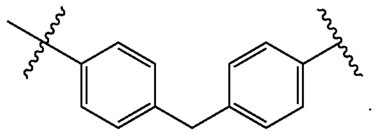 [SMILES: *c1ccc(Cc2ccc(*)cc2)cc1]

"Polyalkylene glycol" (or "polyoxyalkylene") means an oligomer or polymer group of an alkylene glycol, such as polyethylene glycol, polypropylene glycol, or polybutylene glycol. In particular, the polyalkylene glycol group is of formula $—[(CHR^5)_i—O]_k—(CHR^5)_i—$ where:

each $R^5$ is independently a hydrogen or a $C_1$-$C_6$ alkyl (preferably a hydrogen), i is an integer from 1 to 12 (preferably from 2 to 6), and k is an integer from 1 to 250 (preferably from 2 to 50, better still from 2 to 20).

The polyethylene glycol group is in particular of formula $—[(CH_2)_2—O]_k—(CH_2)_2—$ with k an integer from 1 to 250 (preferably from 2 to 50, better still from 2 to 20).

The polypropylene glycol group is in particular of formula $—[CH(CH_3)—CH_2—O]_x—CH(CH_3)—CH_2—$ with k an integer from 1 to 250 (preferably from 2 to 50, better still from 2 to 20). The polybutylene glycol group (or polytetrahydrofuran or polytetramethylene glycol) is in particular of formula $-[(CH_2)_4-O]_k-(CH_2)_4-$ with k an integer from 1 to 250 (preferably from 2 to 50, better still from 2 to 20).

The alkyl and aryl groups as defined above may also be mono- or polysubstituted with groups including in particular the alkyls, cycloalkyls, heterocycloalkyls, aryls, heteroaryls, perfluoroalkyls, alkoxy, alkylthio, alkylamino, halogens, a cyano, a nitro, etc.

"Cycloalkyl" means a mono-, bi- or tricyclic alkyl group, bridged or not. Examples of cycloalkyl are in particular cyclopropyl, cyclobutyl, cyclopentyl, cyclohexyl, cycloheptyl, cyclooctyl, cyclodecyl, or cyclododecyl.

"Heterocycloalkyl" means a mono-, bi- or tricyclic hydrocarbon group, bridged or not, saturated or unsaturated, and comprising at least one heteroatom, such as N (azacycloalkyl), O (oxacycloalkyl) or S (thiacycloalkyl). Examples of heterocycloalkyl are in particular an oxirane, oxetane, 3-dioxolane, benzo-[1,3]-dioxolyl, pyrazolinyl, pyranyl, thiomorpholinyl, pyrazolidinyl, piperidyl, piperazinyl, 1,4-dioxanyl, imidazolinyl, pyrrolinyl, pyrrolidinyl, piperidinyl, imidazolidinyl, morpholinyl, 1,4-dithianyl, pyrrolidinyl, quinolizinyl, oxozolinyl, oxazolidinyl, isoxazolinyl, isoxazolidinyl, thiazolinyl, thiazolidinyl, isothiazolinyl, isothiazolidinyl, dihydropyranyl, or tetrahydrofuranyl.

"Heteroaryl" means a monocyclic or polycyclic aromatic group, comprising at least one heteroatom such as nitrogen, oxygen or sulfur. In particular, a heteroaryl denotes a pyridinyl, thiazolyl, thiophenyl, furanyl, pyrrolyl, imidazolyl, triazolyl, tetrazolyl, benzofuranyl, thianaphthalenyl, indolyl, indolinyl, quinolinyl, isoquinolinyl, benzimidazolyl, triazinyl, thianthrenyl, isobenzofuranyl, phenoxanthinyl, isothiazolyl, isoxazolyl, pyrazinyl, pyridazinyl, indolizinyl, isoindolyl, indazolyl, purinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, benzotriazolyl, benzoxazolyl, benzisoxazolyl, oxindolyl, benzothienyl, benzothiazolyl, s-triazinyl, oxazolyl, or thiofuranyl.

"Alkyloxy" or "alkoxy" means an —O-alkyl group where the alkyl group is as defined above. Examples of alkoxy are in particular a methoxy, ethoxy, propoxy, isopropoxy, butoxy, iso-butoxy, tert-butoxy, pentoxy, or hexyloxy group.

"Alkylthio" means an —S-(alkyl) group, where the alkyl group is as defined above. An example of alkylthio is in particular a methylthio.

"Alkylamino" means an —NH-(alkyl) or $-N(alkyl)_2$ group where the alkyl group is as defined above. Examples of alkylamino are in particular methylamino, ethylamino, or dimethylamino.

"Perfluoroalkyl" means an alkyl group in which the hydrogens have been replaced with a fluorine. An example of perfluoroalkyl is in particular $CF_3$.

"Halogen" means an atom of fluorine, chlorine, bromine or iodine.

"Solvent" means both an organic solvent and an inorganic solvent, or a mixture thereof. Examples of organic solvents are in particular the aliphatic, cyclic or acyclic hydrocarbons such as cyclohexane or pentane, the aromatic hydrocarbons such as benzene, toluene or xylene, the halogenated hydrocarbons such as dichloromethane, chloroform or chlorobenzene, the azotized solvents such as acetonitrile or triethylamine, the oxygenated solvents, in particular the ketones such as acetone, the ethers such as diethyl ether, tert-butylmethyl ether (TBME), tetrahydrofuran (THF), the alcohols such as methanol or ethanol, the esters such as ethyl acetate, or the amides such as dimethylformamide (DMF), dimethyl acetamide (DMAc), the sulfur-containing solvents such as dimethylsulfoxide (DMSO), and a mixture thereof. An example of inorganic solvent is in particular water.

Polymer Compound

The invention relates to a polymer compound comprising (preferably, consisting of):

repeat units of formula (I):

(I)

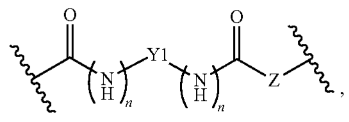

in which n has a value of 0 or 1;

Y1 represents a radical selected from a $(C_1-C_{12})$alkyl, an aryl, and an aryl-$(C_1-C_{12})$alkaryl; and Z represents a radical selected from:

a group represented by the following formula (Ia):

(Ia)

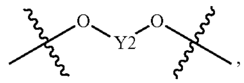

in which Y2 represents a $(C_1-C_{12})$alkyl, aryl or polyalkylene glycol; and a group represented by the following formula (Ib):

(Ib)

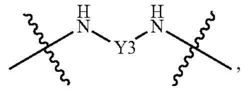

in which Y3 represents a $(C_1-C_{12})$alkyl, aryl, or polyalkylene glycol (preferably a $(C_1-C_{12})$alkyl or aryl);

and in which at least one of Y1, Y2, and Y3 is joined to a peptide residue via a functional residue, the functional residue and the peptide residue optionally being separated by a spacer fragment;

and repeat units of formula (II):

(II)

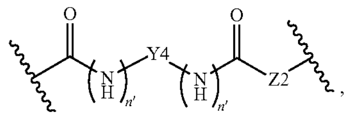

in which n' has a value of 0 or 1;

Y4 represents a radical selected from a $(C_1-C_{12})$alkyl, an aryl, and an aryl-$(C_1-C_{12})$alkaryl; and represents a radical selected from:

a group represented by the following formula (IIa):

(IIa)

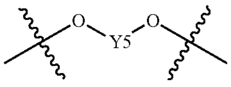, in which Y5 represents a ($C_1$-$C_{12}$)alkyl, aryl or polyalkylene glycol; and a group represented by the following formula (IIb):

(IIb)

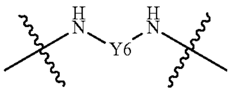, in which Y6 represents a ($C_1$-$C_{12}$)alkyl, aryl, or polyalkylene glycol (preferably, a ($C_1$-$C_{12}$)alkyl or aryl), provided that when n and n' have a value of 0 and Y3 is joined to a peptide residue via a functional residue, the polymer has at least one end of formula (E10) or (E40):

(E10)

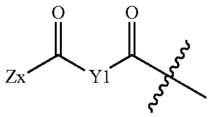, (E40)

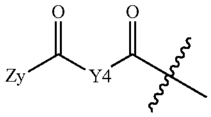

in which Zx and Zy represent independently a ($C_1$-$C_{12}$) alkyl-O— or aryl-O—.

The polymer compound according to the invention comprises (preferably, consists of) repeat units, some of which are substituted with peptides (units of formula (I)). The structure of the polymer compound may be likened to at a comb structure, in which the polymer backbone is linear and is made up of repeat units, and each "branch" or "tooth" attached to the backbone consists of a peptide. It may thus be called a polymer compound with pendant peptides.

More particularly, the polymer compound is of the polyester, polyamide, or polyurethane type, or a combination thereof.

The repeat units of formula (I) of the polymer compound of the invention may be identical to or different than one another.

The repeat units of formula (II) of the polymer compound of the invention may be identical to or different than one another.

In the present invention, the indices n of a repeat unit of formula (I) are identical to each other.

In the same way, the indices n' of a repeat unit of formula (II) are identical to each other. Preferably, the indices n and n', respectively repeat units of formula (I) and (II) of the polymer compound, are identical to each other.

In a particular embodiment, the polymer compound comprises (preferably, consists of) repeat units of formula (I) in which n=0 and repeat units of formula (II) in which n'=0.

In another particular embodiment, the polymer compound comprises (preferably, consists of) repeat units of formula (I) in which n=1 and repeat units of formula (II) in which n'=1.

In certain embodiments, other repeat units may be present in the polymer compound of the invention. Preferably, the repeat units of formula (I) and (II) represent at least 30%, at least 40%, at least 50%, at least 60%, at least 70%, at least 80%, at least 90%, at least 95% by number relative to the total number of repeat units making up the polymer compound of the invention. In a particular embodiment, the polymer compound of the invention only consists of repeat units of formula (I) and (II), i.e. the repeat units of formula (I) and (II) represent 100% by number relative to the total number of repeat units making up the polymer compound of the invention.

The various physicochemical characteristics of the polymer compound according to the invention, such as the number-average or weight-average molecular weight, polydispersity, chemical composition, purity, chemical structure, may be determined by various methods familiar to a person skilled in the art, such as differential scanning calorimetry, elemental analysis, size-exclusion chromatography, mass spectrometry, and/or NMR spectroscopy.

"Polymer compound" means one or more macromolecules (or polymer chain), identical or different, comprising repeat units (or monomer units) joined to one another by covalent bonds, and linearly in such a way that these units form a chain.

The symbol

represents the point of attachment between two units or two fragments of units in the polymer chain, or more generally the point of attachment between two molecular groups. This point of attachment is translated physically by a covalent bond.

The repeat units shown with a symbol

at each end are chained from left to right. The left end of a given unit is connected to the right end of the preceding adjacent unit in the polymer chain and the right end of the given unit is connected to the left end of the adjacent unit that follows in the polymer chain.

According to a particular embodiment, the ratio of the number of repeat units of formula (I) to the total number of repeat units (formula (I) and formula (II)) is between 0.0001/100 and 50/100, preferably between 0.001/100 and 10/100, better still between 0.005/100 and 1/100, or even between 0.0075/100 and 0.1/100.

According to a particular embodiment, the number-average molecular weight of the polymer compound according to the invention is between 1000 and 150000 g/mol, preferably between 5000 and 15000 g/mol. According to a particular embodiment, the weight-average molecular weight of the polymer compound according to the invention is between 1000 and 250000 g/mol, preferably between 5000 and 35000 g/mol.

The weight-average or number-average molecular weight may in particular be determined by size exclusion chromatography, or any other suitable technique known by a person skilled in the art.

According to a particular embodiment, the polydispersity of the polymer compound according to the invention is between 1 and 5, preferably between 1 and 3, better still between 1 and 2.

Within one and the same chain of the polymer compound according to the invention, the repeat units of formula (I), the repeat units of formula (II) (and any other repeat units) may in particular be chained:

- randomly: the probability of finding a repeat unit of formula (I) or (II) at a given point of the chain is independent of the nature of the adjacent units. An example of random chain or part of chain may in particular be -A-A-B-A-B-A-A-B-B-B-A-B-B-A-;
- periodically, and in particular alternating: the repeat units of formula (I) and (II) are chained according to a regular sequential order, for example alternating. An example of periodic chain or part of chain may in particular be -A-B-A-B-A-B-A-B-A-B-; or
- in blocks. An example of chain or part of chain in blocks may in particular be -A-A-A-A-A-A-A-B-B-B-B-B-B-B-B-;

where A represents a repeat unit of formula (I) and B represents a repeat unit of formula (II).

Of course, when the polymer compound comprises several chains, the repeat units of formula (I) and of formula (II) may be chained randomly within one and the same chain, but also from one chain to another, so that the distribution of the repeat units of formula (I) and of formula (II) between the chains is random.

Each chain of the polymer compound according to the invention has two ends. According to a particular embodiment, each end of each chain is represented independently by a formula selected from the following formulas (E1) to (E6):

(E1)

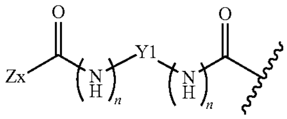

, (E2)

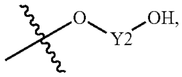

(E3)

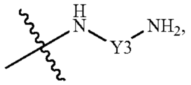

(E4)

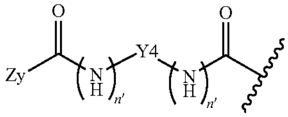

, (E5)

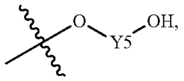

and (E6)

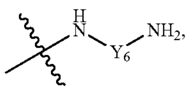

in which n, n', Y1, Y2, Y3, Y4, Y5, and Y6 are as defined above and Zx and Zy represent independently a hydroxy, a chlorine, a ($C_1$-$C_{12}$)alkyl-O— or an aryl-O— (preferably, a chlorine, a ($C_1$-$C_{12}$)alkyl-O— or an aryl-O—, better still a ($C_1$-$C_{12}$)alkyl-O— or an aryl-O), and a salified form thereof.

Of course, the ends of polymer chain as represented by the formulas (E1), (E2), (E3), (E4), (E5), (E6), (E10) and (E40) may include a fragment of repeat unit of formula (I) or (II) making up the polymer chain.

"Salified form" means acid salts or basic salts of the compound or group specified. The acid salts comprise, but are not limited to, salts of hydrochloride, hydrobromide, hydriodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, and para-toluenesulfonate. Basic salts comprise, but are not limited to, salts of aluminum, calcium, lithium, magnesium, potassium, sodium, zinc, and diethanolamine.

According to an embodiment in which Y3 is joined to a peptide residue via a functional residue, the polymer compound according to the invention has at least one end (in particular, consisting of at least one chain having at least one of its two ends, and preferably, each chain having at least one of its two ends) of formula (E10) or (E40):

(E10)

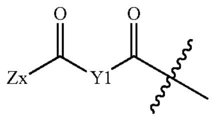

, (E40)

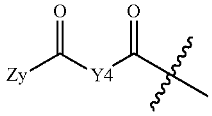

in which Y1 and Y4 are as defined above and Zx and Zy represent independently a ($C_1$-$C_{12}$)alkyl-O— or aryl-O—.

In the unit of formula (I), at least one of Y1, Y2, and Y3 is joined to a peptide residue via a functional residue, the functional residue and the peptide residue optionally being separated by a spacer fragment.

"Peptide residue" means a peptide lacking one or more atoms or group(s) of atoms (for example, —H or —OH) of one of its functional groups. The peptide residue results typically from the reaction of this functional group with a coupling function joined to the rest of the unit of formula (I) (or a spacer), more particularly joined to at least one of Y1, Y2, and Y3.

Examples of peptide functional groups are in particular —$NH_2$ or —$CO_2H$.

The functional groups of the peptide residue are typically —NH— and —CO—.

"Functional residue" means a coupling function joined to the rest of the unit of formula (I), more particularly joined to at least one of Y1, Y2, and Y3, and lacking one or more atoms or group(s) of atoms (for example, —H or —OH). The functional residue results typically from the reaction of this coupling function with a functional group of a peptide (or of a spacer).

Examples of coupling functions are in particular —$NH_2$ or —$CO_2H$.

The functional residues are typically —NH— and —CO—.

"Spacer fragment" means a chemical fragment that separates the repeat unit of formula (I), more precisely the functional residue, and the peptide residue. This fragment lacks one or more atoms or group(s) of atoms (for example, —H or —OH) at the level of one or more of these functional groups. The spacer fragment results from the reaction between a functional group of a spacer with a coupling function and of another functional group of this spacer with a peptide.

According to a first embodiment of the invention, the functional residue and the peptide residue (or more precisely the functional group of the peptide residue) are not separated by a spacer fragment. In said embodiment, the coupling function and the functional group of a peptide are advantageously selected so that they have complementary reactivity. For example, when the coupling function is a group $—NH_2$, the functional group of the peptide is advantageously $—CO_2H$ or a derivative of this group (ester, acyl chloride etc.), thus reacting to form a fragment -(functional residue)-(functional group of the peptide residue)- in the form of an amide (—NH—CO—); and when the coupling function is a group $—CO_2H$ or a derivative of this group (ester, acyl chloride etc.), the functional group of the peptide is advantageously $—NH_2$, thus reacting to form a fragment -(functional residue)-(functional group of the peptide residue)- in the form of an amide (—CO—NH—).

Preferably, the functional residue and the functional group of the peptide residue are respectively —CO— and —NH—, or —NH— and —CO—, thus forming an amide (—CO—NH— or —NH—CO—).

According to a second embodiment of the invention, the functional residue and the peptide residue (or more precisely a functional group of the peptide residue) are separated by a spacer fragment. In such an embodiment:

the coupling function reacts with a first functional group of a spacer (with the result that the functional residue is joined to the spacer fragment), and a functional group of the peptide reacts with a second functional group of the spacer (with the result that the peptide residue is joined to the spacer fragment).

The various groups or functional residues are selected in such a way that they have complementary reactivity.

For example:

when the coupling function or the functional group of the peptide is a group $—NH_2$, the functional group of the spacer is advantageously $—CO_2H$ or a derivative of $—CO_2H$ (ester, acyl chloride etc.), thus reacting to form an amide (—NH—CO—); and when the coupling function or the functional group of the peptide is a group $—CO_2H$ or a derivative of $—CO_2H$ (ester, acyl chloride etc.), the functional group of the spacer is advantageously $—NH_2$, thus reacting to form an amide (—CO—NH—).

According to a particular embodiment, the spacer fragment is of formula -(X1)-(X2)-(X3)-, in which X1 and X3 represent, each independently, —NH— or —CO—, and X2 represents a $(C_1\text{-}C_{12})$alkyl, aryl or polyalkylene glycol.

According to a particular embodiment, X1 and X3 represent —CO—. In an embodiment of this kind, the functional residue and the functional group of the peptide residue are advantageously —NH—.

According to another particular embodiment, X1 represents —NH— and X3 represents —CO—. In an embodiment of this kind, the functional residue and the functional group of the peptide residue are advantageously —CO— and —NH—, respectively. It is considered here, arbitrarily, that X1 is joined to the functional residue and X3 is joined to the peptide residue.

According to another particular embodiment, X2 represents a $(C_1\text{-}C_6)$alkyl, better still a methyl, a propyl (e.g. 1,3-propyl) or a pentyl (e.g. 1,5-pentyl).

According to a particular embodiment, Y1 and/or Y3 are joined to a peptide residue via a functional residue, the functional residue and the peptide residue optionally being separated by a spacer fragment.

According to another particular embodiment, Y2 is joined to a peptide residue via a functional residue, the functional residue and the peptide residue optionally being separated by a spacer fragment.

According to a preferred embodiment, Y1 is joined to a peptide residue via a functional residue, the functional residue and the peptide residue optionally being separated by a spacer fragment.

According to another preferred embodiment, Y3 is joined to a peptide residue via a functional residue, the functional residue and the peptide residue optionally being separated by a spacer fragment.

According to a particular embodiment, Y1 is selected from an ethyl, a propyl, a butyl, a pentyl, a hexyl, a phenyl, and a phenyl-methyl-phenyl.

According to another particular embodiment, Y2 is selected from an ethyl, a propyl, a butyl, a pentyl, a hexyl, a phenyl, a polyethylene glycol, polypropylene glycol, and a polybutylene glycol.

According to another particular embodiment, Y3 is selected from an ethyl, a propyl, a butyl, a pentyl, a hexyl, a phenyl, a polyethylene glycol, polypropylene glycol, and a polybutylene glycol.

According to another particular embodiment, Y4 is selected from an ethyl, a propyl, a butyl, a pentyl, a hexyl, a phenyl, and a phenyl-methyl-phenyl.

According to another particular embodiment, Y5 is selected from an ethyl, a propyl, a butyl, a pentyl, a hexyl, a phenyl, a polyethylene glycol, a polypropylene glycol and a polybutylene glycol.

According to another particular embodiment, Y6 is selected from an ethyl, a propyl, a butyl, a pentyl, a hexyl, a phenyl, a polyethylene glycol, polypropylene glycol, and a polybutylene glycol.

The groups Y1 to Y6 are divalent groups, i.e. they are attached to the rest of the molecule by two bonds, each bond involving the same carbon (of said divalent group) or two different carbons (of said divalent group).

Preferably, a divalent group of the "alkyl" type is attached to the rest of the molecule by the carbons at the ends of the alkyl chain.

A divalent group of the "propyl" type includes in particular 1,1-propyl, 1,2-propyl, and 1,3-propyl, and preferably 1,3-propyl.

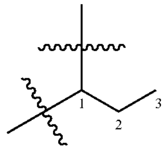
, (1,1-propyl)

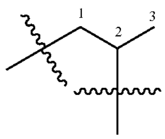
, (1,2-propyl)

-continued

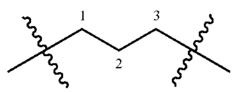

(1,3-propyl)

A preferred divalent group of the “ethyl” type is 1,2-ethyl.

A preferred divalent group of the “butyl” type is 1,4-butyl.

A preferred divalent group of the “pentyl” type is 1,5-pentyl.

A preferred divalent group of the “hexyl” type is 1,6-hexyl.

A divalent group of the “phenyl” type includes in particular 1,2-phenyl, 1,3-phenyl and 1,4-phenyl, preferably 1,3-phenyl and 1,4-phenyl, and better still, 1,4-phenyl.

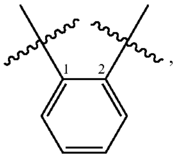, (1,2-phenyl)

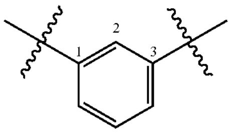, (1,3-phenyl)

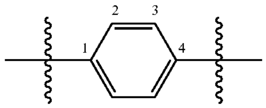

(1,4-phenyl)

Preferably, a divalent group of the “polyalkylene glycol” type is attached to the rest of the molecule by the atoms at the ends of the polyalkylene glycol chain.

According to a particular embodiment, Y1 is selected from a 1,2-ethyl, a 1,3-propyl, a 1,4-butyl, a 1,5-pentyl, a 1,6-hexyl, a 1,3-phenyl, a 1,4-phenyl, and a phenyl-methyl-phenyl.

According to another particular embodiment, Y2 is selected from a 1,2-ethyl, a 1,3-propyl, a 1,4-butyl, a 1,5-pentyl, a 1,6-hexyl, a 1,3-phenyl, a 1,4-phenyl, a polyethylene glycol, a polypropylene glycol and a polybutylene glycol.

According to another particular embodiment, Y3 is selected from a 1,2-ethyl, a 1,3-propyl, a 1,4-butyl, a 1,5-pentyl, a 1,6-hexyl, a 1,3-phenyl, a 1,4-phenyl, a polyethylene glycol, a polypropylene glycol and a polybutylene glycol.

According to another particular embodiment, Y4 is selected from a 1,2-ethyl, a 1,3-propyl, a 1,4-butyl, a 1,5-pentyl, a 1,6-hexyl, a 1,3-phenyl, a 1,4-phenyl, and a phenyl-methyl-phenyl.

According to another particular embodiment, Y5 is selected from a 1,2-ethyl, a 1,3-propyl, a 1,4-butyl, a 1,5-pentyl, a 1,6-hexyl, a 1,3-phenyl, a 1,4-phenyl, a polyethylene glycol, a polypropylene glycol and a polybutylene glycol.

According to another particular embodiment, Y6 is selected from a 1,2-ethyl, a 1,3-propyl, a 1,4-butyl, a 1,5-pentyl, a 1,6-hexyl, a 1,3-phenyl, a 1,4-phenyl, a polyethylene glycol, a polypropylene glycol and a polybutylene glycol.

The functional residue (or the coupling function) may be attached in any position of said divalent group Y1, Y2, or Y3, thus forming a “Y-(functional residue)” structure, where Y is at least one of Y1, Y2 or Y3 joined to a peptide residue via the functional residue (and optionally a spacer fragment).

Examples of “Y-(functional residue)” structures are, in particular:

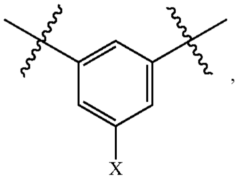, 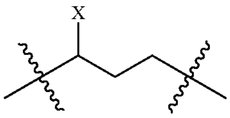, or

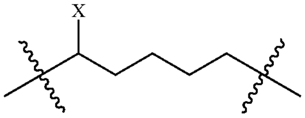, where X represents the functional residue, in particular —CO— or —NH—.

According to an embodiment where Y is Y1, the “Y-(functional residue)” structure is advantageously

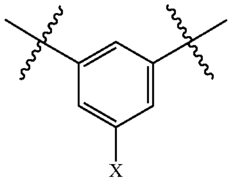 or 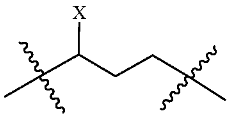, where X represents the functional residue —CO— or —NH—, preferably —NH—. In an embodiment of this kind, preferably the “Y-(functional residue)” structure is:

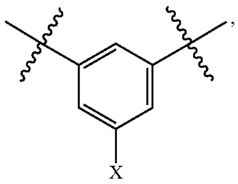, where X represents the functional residue, in particular —CO— or —NH—, preferably —NH—.

According to an embodiment where Y is Y3, the “Y-(functional residue)” structure is advantageously:

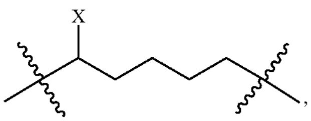, where X represents the functional residue —CO— or —NH—, preferably —CO—.

According to a particular embodiment, Y1 and Y4 are identical.

According to another particular embodiment, Y2 and Y5 are identical.

According to another particular embodiment, Y3 and Y6 are identical.

Peptide

"Peptide" means a homo- or hetero-oligomer or polymer of amino acids joined together by peptide bonds (i.e. bonds of the amide type). More particularly, the peptide may correspond to the following formula:

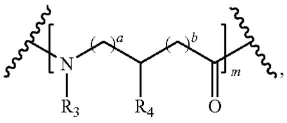, in which,

- m is an integer between 2 and 200, more particularly between 2 and 50, even more particularly between 2 and 10;
- R3 represents a hydrogen atom, or a ($C_1$-$C_6$)alkyl optionally substituted with an aryl;
- R4 represents a side chain of amino acid, in particular of natural amino acid, of nonnatural amino acid, of modified or protected amino acid;
- or, R3 and R4, taken together with the group $—N—(CH_2)_a—CH—$ to which they are attached, may form a ring; and
- a and b are integers selected in such a way that the sum (a+b) is an integer from 0 to 10.

According to a particular embodiment, the peptide is a protein.

According to another particular embodiment, the peptide is a single amino acid (natural or nonnatural, modified or unmodified).

Preferably, said peptide is a bioactive peptide.

In particular, the bioactive peptide may be an antimicrobial peptide, a peptide promoting adhesion and/or cellular proliferation, an anti-inflammatory, pro-cicatricial peptide, or promoting osteointegration.

Examples of such peptides are in particular RGD, DGEA, GHK, the magainin peptides, the peptides of sequence BBXB where B is a basic amino acid and X is a nonbasic amino acid, the peptides of pro-collagen sequence of the type Gly-PRO-X or Gly-X-Hyp (where X denotes any amino acid), peptides whose sequence is derived from Tenascin X.

Preferably, said peptide is an antimicrobial peptide, and more particularly a cationic antimicrobial peptide. An antimicrobial peptide (or cationic antimicrobial peptide) generally comprises positively charged amino acids, such as arginine or lysine, and hydrophobic amino acids, such as phenylalanine, leucine or isoleucine. Said peptide may further comprise other amino acids.

In a particular embodiment, the peptide is selected from Gly-Phe-Arg, Arg-Phe (also designated RF), Phe-Arg (also designated FR), Arg-Phe-Arg-Phe (also designated RFRF or $(RF)_2$), Phe-Arg-Phe-Arg (also designated FRFR or $(FR)_2$), Arg-Phe-Arg-Phe-Arg-Phe (also designated RFRFRF or $(RF)_3$), Phe-Arg-Phe-Arg-Phe-Arg (also designated FRFRFR or $(FR)_3$), Arg-Phe-Arg-Phe-Arg-Phe-Arg-Phe (also designated RFRFRFRF or $(RF)_4$), Phe-Arg-Phe-Arg-Phe-Arg-Phe-Arg (also designated FRFRFRFR or $(FR)_4$), and Arg-Arg-Palm (also designated RR-Palm or $(R)_2$-Palm).

In a preferred embodiment, the peptide is Arg-Phe-Arg-Phe-Arg-Phe-Arg-Phe, Phe-Arg-Phe-Arg-Phe-Arg-Phe-Arg or Arg-Arg-Palm. More preferably, the peptide is Arg-Phe-Arg-Phe-Arg-Phe-Arg-Phe, or Phe-Arg-Phe-Arg-Phe-Arg-Phe-Arg. Better still, the peptide is Arg-Phe-Arg-Phe-Arg-Phe-Arg-Phe.

The 3-letter abbreviation "Gly" or single letter abbreviation "G" corresponds to glycine. The 3-letter abbreviation "Phe" or single letter abbreviation "F" corresponds to phenylalanine. The 3-letter abbreviation "Arg" or single letter abbreviation "R" corresponds to arginine. The 3-letter abbreviation "Lys" or single letter abbreviation "K" corresponds to lysine. The 3-letter abbreviation "Asp" or single letter abbreviation "D" corresponds to aspartic acid (or aspartate).

The 3-letter abbreviation "Ala" or single letter abbreviation "A" corresponds to alanine. The 3-letter abbreviation "Glu" or single letter abbreviation "E" corresponds to glutamic acid (or glutamate). The 3-letter abbreviation "His" or single letter abbreviation "H" corresponds to histidine. The 3-letter abbreviation "Pro" or single letter abbreviation "P" corresponds to proline. The 3-letter abbreviation "Hyp" corresponds to hydroxyproline. The abbreviation "Palm" corresponds to a palmityl residue (and may be represented by the formula $—(CH_2)_{15}—CH_3$).

For the peptides described in the present application, the convention for writing the sequences places the C-terminal end on the right, the sequence being written from left to right, from the N-terminal end to the C-terminal end.

In the peptide Arg-Arg-Palm, the palmityl residue is typically joined to the C-terminal of Arg by an amine function. The peptide Arg-Arg-Palm may be represented as follows:

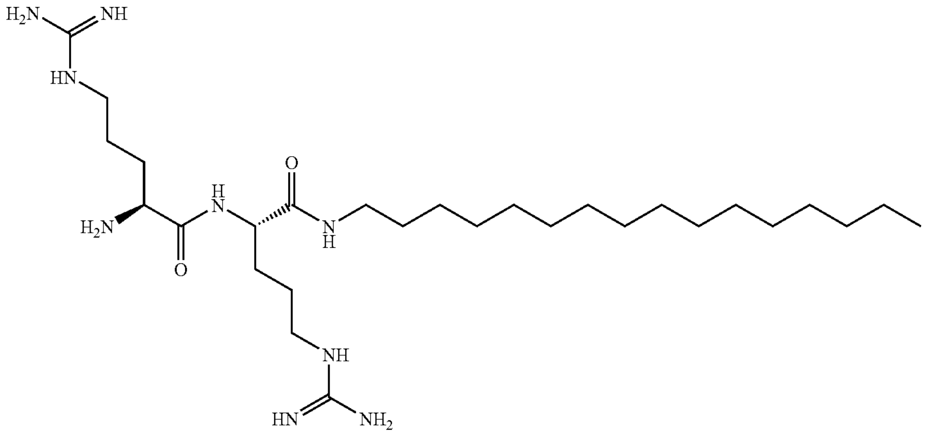.

In the peptide Arg-Phe-Arg-Phe-Arg-Phe-Arg-Phe, the C-terminal end may in particular be joined to an amine function. The peptide Arg-Phe-Arg-Phe-Arg-Phe-Arg-Phe may in particular be represented as follows:

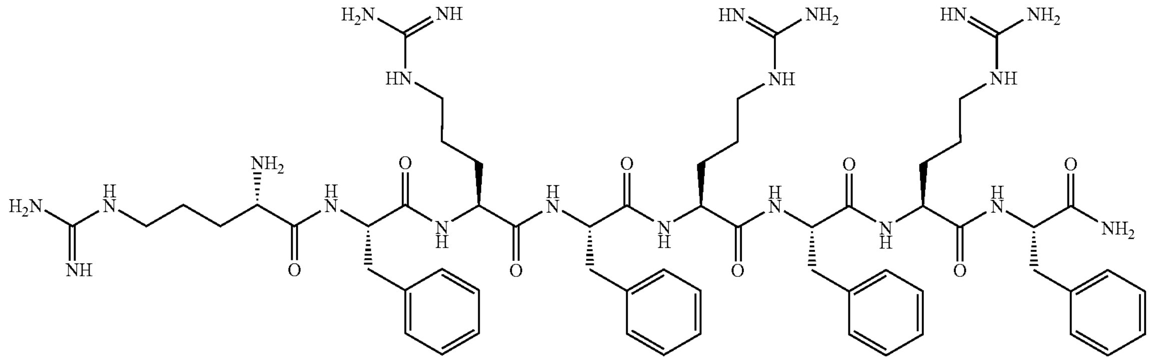 [SMILES: N=C(N)NCCC[C@H](NC(=O)[C@H](Cc1ccccc1)NC(=O)[C@H](CCCNC(=N)N)NC(=O)[C@H](Cc1ccccc1)NC(=O)[C@H](CCCNC(=N)N)NC(=O)[C@H](Cc1ccccc1)NC(=O)[C@@H](N)CCCNC(=N)N)C(=O)N[C@@H](Cc1ccccc1)C(N)=O]

In the peptide Phe-Arg-Phe-Arg-Phe-Arg-Phe-Arg, the N-terminal end may in particular be joined to an acetyl function. The peptide Phe-Arg-Phe-Arg-Phe-Arg-Phe-Arg may in particular be represented as follows:

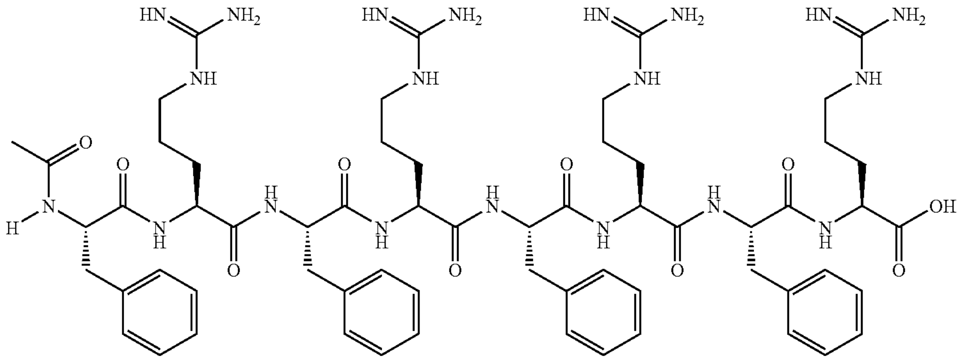

The peptide, or a peptide residue thereof, may be joined to the monomer or polymer of the invention (optionally via a spacer fragment) by its N-terminal end, C-terminal end, or by any other functional group borne by the peptide. Preferably, the peptide, or a peptide residue thereof, is joined to the monomer or polymer of the invention (optionally via a spacer fragment) by its N-terminal end or C-terminal end, better still by its N-terminal end.

In a particular embodiment, the peptide Arg-Phe-Arg-Phe-Arg-Phe-Arg-Phe or a peptide residue thereof is joined to the monomer or polymer of the invention (optionally via a spacer fragment) by its N-terminal end.

In another particular embodiment, the peptide Phe-Arg-Phe-Arg-Phe-Arg-Phe-Arg or a peptide residue thereof is joined to the monomer or polymer of the invention (optionally via a spacer fragment) by its C-terminal end.

The peptide may be prepared by any technique known by a person skilled in the art. Advantageously, the peptide is prepared by peptide synthesis on a solid support. The solid support may in particular be a silica, an alumina, glass, a polystyrene type resin, a polyethylene glycol type resin. The solid support may be a support functionalized with a chemical group suitable for peptide synthesis, for example a resin functionalized with a group 4-((2,4-dimethoxyphenyl)(Fmoc-amino)methyl)phenoxyalkyl (e.g. Rink-Amide® Resin) or with a 2-chlorotrityl chloride group. As a variant, the peptide may be synthesized in solution. The peptides described in the present application may be in protected or unprotected form (preferably unprotected). The protective groups of the peptides are familiar to a person skilled in the art, and are for example the group Pbf (pentamethylbenzofuranylsulfonyl), Boc (tert-butoxycarbonyl), or Fmoc (fluorenylmethoxycarbonyl).

Polyesters

According to a particular embodiment, the polymer compound of the invention is a polyester comprising (preferably consisting of) repeat units of formula (I) in which:

n=0;

Z is a group represented by the following formula (Ia):

(Ia)

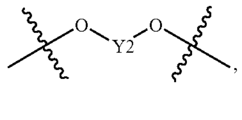

in which Y2 represents a $(C_1\text{-}C_{12})$alkyl, aryl or polyalkylene glycol; and repeat units of formula (II) in which:

n'=0;

Z2 is a group represented by the following formula (IIa):

(IIa)

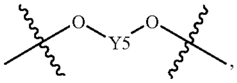

in which Y5 represents a $(C_1\text{-}C_{12})$alkyl, aryl or polyalkylene glycol, and in which at least one of Y1 and Y2, preferably Y1, is joined to a peptide residue via a functional residue, the functional residue and the peptide residue optionally being separated by a spacer fragment.

In an embodiment of this kind, the peptide residue is advantageously a residue of the peptide Arg-Phe-Arg-Phe-Arg-Phe-Arg-Phe, Phe-Arg-Phe-Arg-Phe-Arg-Phe-Arg, or Arg-Arg-Palm, better still Arg-Phe-Arg-Phe-Arg-Phe-Arg-Phe.

According to a particular embodiment, Y1, Y2, Y4 and Y5 are selected, independently, from a $(C_1\text{-}C_6)$alkyl and a phenyl.

According to a more particular embodiment, Y1, Y2, Y4 and Y5 are selected, independently, from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl. According to a preferred embodiment, Y1 represents a phenyl (in particular a 1,3-phenyl) or a propyl (in particular a 1,3-propyl).

According to another preferred embodiment, the "Y-(functional residue)" structure, where Y is Y1 and/or Y2, preferably Y1, is:

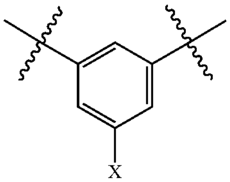

or

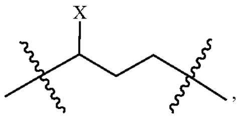

where X represents the functional residue, in particular —CO— or —NH—, preferably —NH—, which is itself joined to the peptide residue, the functional residue and the peptide residue optionally being separated by a spacer fragment.

In a particular embodiment, Y2 and Y5 are identical. Preferably, Y2 and Y5 represent a $(C_1\text{-}C_6)$alkyl, more preferably a 1,2-ethyl or a 1,4-butyl, better still a 1,4-butyl.

In a preferred embodiment, the polymer compound of the invention comprises:

- repeat units of formula (I) in which n=n'=0, Y1 represents a 1,3-propyl or 1,3-phenyl (preferably, a 1,3-phenyl) and Z is a group of formula (Ia) in which Y2 represents a 1,2-ethyl or 1,4-butyl (preferably a 1,4-butyl); where Y1 is joined to a peptide residue via a functional residue, the functional residue and the peptide residue optionally being separated by a spacer fragment;
- repeat units of formula (II) in which Y4 is a 1,2-ethyl or a 1,4-butyl (preferably a 1,4-butyl), and Z2 is a group of formula (IIa) in which Y5 represents a 1,2-ethyl or 1,4-butyl (preferably a 1,4-butyl); and
- optionally, repeat units of formula (II) in which Y4 is a 1,4-phenyl, and Z2 is a group of formula (IIa) in which Y5 represents a 1,2-ethyl or 1,4-butyl (preferably a 1,4-butyl).

In a preferred embodiment of this kind, the functional residue is advantageously —NH—, and the spacer fragment is advantageously of formula -(X1)-(X2)-(X3)- where X1 and X3 represent —CO— and X2 is a $(C_1\text{-}C_6)$alkyl, such as a 1,3-propyl.

In a preferred embodiment of this kind, the peptide residue is advantageously a residue of the peptide Arg-Phe-Arg-Phe-Arg-Phe-Arg-Phe, Phe-Arg-Phe-Arg-Phe-Arg-Phe-Arg, or Arg-Arg-Palm, better still Arg-Phe-Arg-Phe-Arg-Phe-Arg-Phe.

Polyamides

According to another particular embodiment, the polymer compound of the invention is a polyamide comprising (preferably, consisting of) repeat units of formula (I) in which:

n=0;

Z is a group represented by the following formula (Ib):

(Ib)

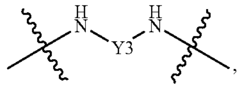

in which Y3 represents a $(C_1\text{-}C_{12})$alkyl, aryl, or polyalkylene glycol (preferably, a $(C_1\text{-}C_{12})$alkyl, or aryl);

and repeat units of formula (II) in which:

n'=0

Z2 is a group represented by the following formula (IIb):

(IIb)

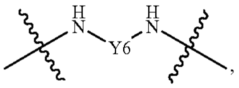

in which Y6 represents a $(C_1\text{-}C_{12})$alkyl, aryl, or polyalkylene glycol (preferably, a $(C_1\text{-}C_{12})$alkyl or aryl), and in which at least one of Y1 and Y3 is joined to a peptide residue via a functional residue, the functional residue and the peptide residue optionally being separated by a spacer fragment.

In an embodiment of this kind, the peptide residue is advantageously a residue of the peptide Arg-Phe-Arg-Phe-Arg-Phe-Arg-Phe, Phe-Arg-Phe-Arg-Phe-Arg-Phe-Arg, or Arg-Arg-Palm, better still Arg-Phe-Arg-Phe-Arg-Phe-Arg-Phe or Phe-Arg-Phe-Arg-Phe-Arg-Phe-Arg.

According to a particular embodiment, Y1, Y3, Y4 and Y6 are selected, independently, from a $(C_1\text{-}C_6)$alkyl and a phenyl.

According to a more particular embodiment, Y1, Y3, Y4 and Y6 are selected, independently, from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl.

According to a preferred embodiment, Y1 is joined to a peptide residue via a functional residue, the functional residue and the peptide residue optionally being separated by a spacer fragment. According to this preferred embodiment, the "Y-(functional residue)" structure, where Y is Y1, is advantageously:

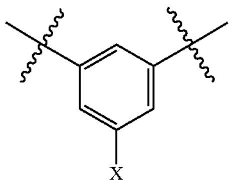

or

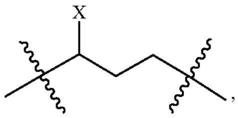

, where X represents the functional residue, in particular —CO— or —NH—, preferably NH, and preferably,

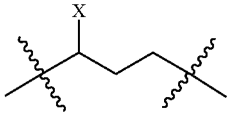

, where X represents the functional residue —NH—.

According to another preferred embodiment, Y3 is joined to a peptide residue via a functional residue, the functional residue and the peptide residue optionally being separated by a spacer fragment.

According to this preferred embodiment, the "Y-(functional residue)" structure, where Y is Y3, is advantageously:

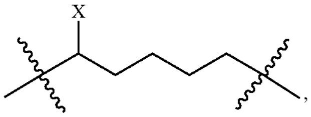

, where X represents the functional residue —CO— or —NH—, preferably —CO—.

According to this preferred embodiment, the polymer compound that is a polyamide has at least one end (in particular, consisting of at least one chain having at least one of its two ends, and preferably, each chain having at least one of its two ends) of formula (E10) or (E40):

(E10)

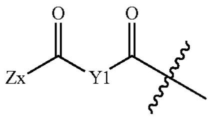

, (E40)

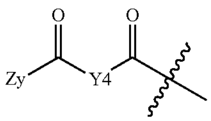

in which Y1 and Y4 are as defined above and Zx and Zy represent independently a $(C_1-C_{12})$alkyl-O— or aryl-O—.

In a particular embodiment, Y3 and Y6 are identical. Preferably, Y3 and Y6 represent a $(C_1-C_6)$alkyl.

Polyurethanes

According to another particular embodiment, the polymer compound of the invention is a polyurethane comprising (preferably, consisting of) repeat units of formula (I) in which:

n=1;

Y1 represents a radical selected from a $(C_1-C_{12})$alkyl, an aryl, and an aryl-$(C_1-C_{12})$alkaryl; and Z represents a radical selected from:

a group represented by the following formula (Ia):

(Ia)

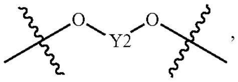

, in which Y2 represents a $(C_1-C_{12})$alkyl, aryl or polyalkylene glycol; and a group represented by the following formula (Ib):

(Ib)

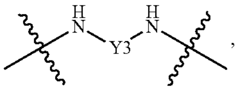

, in which Y3 represents a $(C_1-C_{12})$alkyl, aryl, or polyalkylene glycol;

in which at least one of Y2 and Y3 is joined to a peptide residue via a functional residue, the functional residue and the peptide residue optionally being separated by a spacer fragment;

and repeat units of formula (II) in which:

n'=1;

Y4 represents a radical selected from a $(C_1-C_{12})$alkyl, an aryl, and an aryl-$(C_1-C_{12})$alkaryl; and Z2 represents a radical selected from:

a group represented by the following formula (IIa):

(IIa)

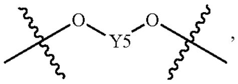

, in which Y5 represents a $(C_1-C_{12})$alkyl, aryl or polyalkylene glycol; and a group represented by the following formula (IIb):

(IIb)

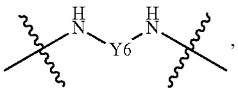

, in which Y6 represents a $(C_1-C_{12})$alkyl, aryl, or polyalkylene glycol.

In an embodiment of this kind, the peptide residue is advantageously a residue of the peptide Arg-Phe-Arg-Phe-Arg-Phe-Arg-Phe, Phe-Arg-Phe-Arg-Phe-Arg-Phe-Arg, or Arg-Arg-Palm, better still Arg-Phe-Arg-Phe-Arg-Phe-Arg-Phe.

According to a particular embodiment, Y1 and Y4 are identical and are preferably an aryl-$(C_1-C_{12})$alkaryl such as a phenyl-methyl-phenyl.

According to another particular embodiment, Y3 and Y6 are selected, independently, from a $(C_1-C_{12})$alkyl and aryl.

According to a particular embodiment, Y1 and Y4 are selected, independently, from a $(C_1-C_6)$alkyl, a phenyl-methyl-phenyl and a phenyl, and Y2, Y3, Y5, and Y6 are selected, independently, from a ($C_1$-$C_6$)alkyl, a phenyl, a polyethylene glycol, a polypropylene glycol, and a polybutadiene glycol.

According to a particular embodiment, Y1, Y2, Y3, Y4, Y5, and Y6 are selected, independently, from a ($C_1$-$C_6$)alkyl and a phenyl.

According to a more particular embodiment, Y1, Y2, Y3, Y4, Y5, and Y6 are selected, independently, from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl.

In another particular embodiment, the polymer compound comprises:

- repeat units of formula (I) in which:
  - n has a value of 0;
  - Y1 represents a radical selected from a ($C_1$-$C_{12}$)alkyl, an aryl, and an aryl-($C_1$-$C_{12}$)alkaryl (preferably from a ($C_1$-$C_6$)alkyl and an aryl, better still Y1 is a phenyl); and
  - Z represents a group represented by the following formula (Ia):

(Ia)

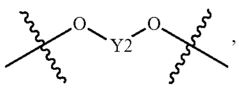,

- in which Y2 represents a ($C_1$-$C_{12}$)alkyl, aryl, or polyalkylene glycol (preferably a ($C_1$-$C_6$)alkyl, or polyalkylene glycol, better still a ($C_1$-$C_6$)alkyl); and
- in which Y1 is joined to a peptide residue via a functional residue, the functional residue and the peptide residue optionally being separated by a spacer fragment; and
- repeat units of formula (II) in which:
  - n' has a value of 1;
  - Y4 represents a radical selected from a ($C_1$-$C_{12}$)alkyl, an aryl and an aryl-($C_1$-$C_{12}$)alkaryl (preferably an aryl-($C_1$-$C_{12}$)alkaryl, such as a phenyl-methyl-phenyl); and
  - Z2 represents a group represented by the following formula (IIa):

(IIa)

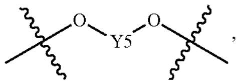,

- in which Y5 represents a ($C_1$-$C_{12}$)alkyl, aryl, or polyalkylene glycol (preferably a ($C_1$-$C_6$)alkyl or polyalkylene glycol).

In an embodiment of this kind, the units of formula (II) may in particular be a combination of:

- repeat units of formula (II) as defined above where Y5 represents a ($C_1$-$C_{12}$)alkyl; and
- repeat units of formula (II) as defined above where Y5 represents a polyalkylene glycol.

In another embodiment, the polymer compound of the invention further comprises other monomer or polymer units known by a person skilled in the art. In particular, the polymer compound may comprise a block consisting of units of formula (I) and (II) as defined above, and one or more other polymer blocks consisting of repeat units known by a person skilled in the art, such as a polycaprolactone block.

In one embodiment, the polymer compound comprises units of formula (I) of the polymer compound in which:

- n=0 or 1, preferably 0, and
- the group Y1 is joined to a peptide residue via a functional residue, the functional residue and the peptide residue being separated by a spacer fragment, according to any one of the formulas (Y1-M1) and (Y1-M2):

(Y1-M1)

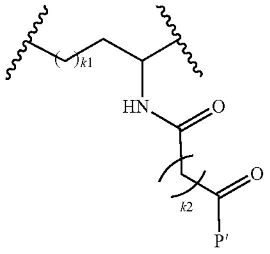

(Y1-M2)

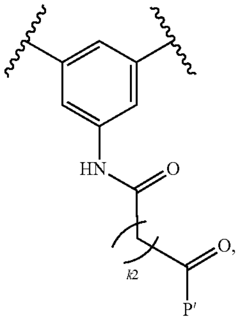

where, in each of said formulas:

- k1 is an integer from 1 to 8, preferably from 1 to 4, better still k1 has a value of 1;
- each k2 is an integer from 1 to 8, preferably from 1 to 6, better still k2 has a value of 3; and
- P' represents a peptide residue, preferably a residue of the peptide Arg-Phe-Arg-Phe-Arg-Phe-Arg-Phe, of the peptide Phe-Arg-Phe-Arg-Phe-Arg-Phe-Arg, or of the peptide Arg-Arg-Palm, better still a residue of the peptide Arg-Phe-Arg-Phe-Arg-Phe-Arg-Phe.

In an embodiment of this kind, Z is preferably a group of formula (Ia) where Y2 represents a ($C_1$-$C_{12}$)alkyl (preferably, a ($C_1$-$C_6$)alkyl such as an ethyl or butyl).

In another particular embodiment, the polymer compound comprises units of formula (I) of the polymer compound in which:

- n=0 or 1, preferably 0, and
- the group Y1 is joined to a peptide residue via a functional residue, the functional residue and the peptide residue being separated by a spacer fragment, according to the following formula (Y1-M3):

(Y1-M3)

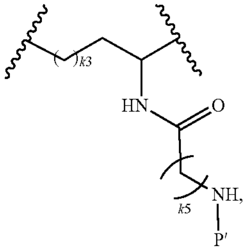

in which:

k3 is an integer from 1 to 8, preferably from 1 to 4, better still k3 has a value of 1;

k5 is an integer from 1 to 8, preferably from 1 to 6, better still k5 has a value of 5; and P' represents a peptide residue, preferably a residue of the peptide Arg-Phe-Arg-Phe-Arg-Phe-Arg-Phe, Phe-Arg-Phe-Arg-Phe-Arg-Phe-Arg or of the peptide Arg-Arg-Palm, better still of the peptide Phe-Arg-Phe-Arg-Phe-Arg-Phe-Arg.

In an embodiment of this kind, Z is preferably a group of formula (Ib) where Y3 represents a $(C_3-C_{10})$alkyl (preferably a $(C_3-C_8)$alkyl such as a hexyl).

In another particular embodiment, the polymer compound comprises units of formula (I) of the polymer compound in which:

n=0 or 1; preferably 1, and

Z is a group of formula (Ia) where Y2 is joined to a peptide residue via a functional residue, the functional residue and the peptide residue being separated by a spacer fragment, according to the formula (Y2-M4):

(Y2-M4)

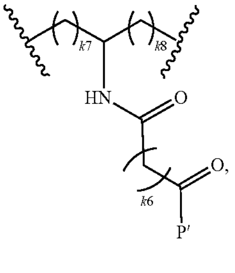

in which:

k6 is an integer from 1 to 8, preferably from 1 to 4, better still k6 has a value of 1;

k7 is an integer from 1 to 8, preferably from 1 to 4, better still k7 has a value of 1;

k8 is an integer from 1 to 8, preferably from 1 to 4, better still k8 has a value of 1; and P' represents a peptide residue, preferably a residue of the peptide Arg-Phe-Arg-Phe-Arg-Phe-Arg-Phe, Phe-Arg-Phe-Arg-Phe-Arg-Phe-Arg, or of the peptide Arg-Arg-Palm.

Monomer Compound

The invention also relates to a monomer compound represented by the following formula (III-1):

(III-1)

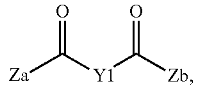

in which

Y1 represents a radical selected from a $(C_1-C_{12})$alkyl, an aryl, and an aryl-$(C_1-C_{12})$alkaryl;

Za represents a radical selected from:

a $(C_1-C_{12})$alkyl-O—, an aryl-O—, a chlorine; and, a group represented by the following formula (IIIa):

(IIIa)

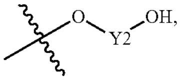

in which Y2 represents a $(C_1-C_{12})$alkyl, aryl or polyalkylene glycol (preferably a $(C_1-C_{12})$alkyl or aryl); and Zb represents a radical selected from:

a $(C_1-C_{12})$alkyl-O—, an aryl-O—, a chlorine;

a group represented by the following formula (IIIa):

(IIIa)

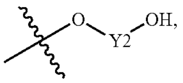

in which Y2 represents a $(C_1-C_{12})$alkyl, aryl, or polyalkylene glycol (preferably a $(C_1-C_{12})$alkyl or aryl); and a group represented by the following formula (IIIb):

(IIIb)

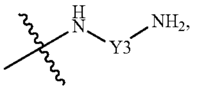

in which Y3 represents a $(C_1-C_{12})$alkyl, aryl, or polyalkylene glycol (preferably a $(C_1-C_{12})$alkyl or aryl);

and in which at least one of Y1, Y2, and Y3 is joined to a peptide residue via a functional residue, the functional residue and the peptide residue optionally being separated by a spacer fragment, provided that when Y3 is joined to a peptide residue via a functional residue, the functional residue and the peptide residue optionally being separated by a spacer fragment, Za is selected from a $(C_1-C_{12})$alkyl-O— and an aryl-O—.

In a particular embodiment, the peptide residue is a residue of the peptide Arg-Phe-Arg-Phe-Arg-Phe-Arg-Phe, Phe-Arg-Phe-Arg-Phe-Arg-Phe-Arg, or Arg-Arg-Palm, better still Arg-Phe-Arg-Phe-Arg-Phe-Arg-Phe.

In a particular embodiment, said spacer fragment is of formula -(X1)-(X2)-(X3)-, in which X1 and X3 represent, each independently, —NH— or —CO—, and X2 represents a $(C_1-C_{12})$alkyl, aryl, or polyalkylene glycol.

According to a particular embodiment, Y1 represents a radical selected from a $(C_1-C_{12})$alkyl and an aryl.

According to a particular embodiment, Y1 to Y3 are each selected, independently, from an ethyl, a propyl, a butyl, a pentyl, a hexyl and a phenyl, and preferably from a 1,2-ethyl, 1,3-propyl, 1,4-butyl, 1,5-pentyl, 1,6-hexyl, 1,2-phenyl, 1,3-phenyl and 1,4-phenyl.

According to a particular embodiment, Za and Zb represent, each independently, a chlorine, a $(C_1\text{-}C_{12})$alkyl-O—, such as a methyl-O— or an ethyl-O—, or an aryl-O—, such as a phenyl-O—, preferably a $(C_1\text{-}C_{12})$alkyl-O— or an aryl-O— (better still, a $(C_1\text{-}C_{12})$alkyl-O—), and Y1 is joined to a peptide residue via a functional residue, the functional residue and the peptide residue optionally being separated by a spacer fragment. In an embodiment of this kind, Za and Zb are advantageously identical.

According to another embodiment, Za and Zb are a group represented by the following formula (IIIa):

(IIIa)

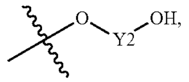

in which Y2 represents a $(C_1\text{-}C_{12})$alkyl, aryl or polyalkylene glycol, and at least one of Y1 and Y2, preferably Y1, is joined to a peptide residue via a functional residue, the functional residue and the peptide residue optionally being separated by a spacer fragment. In an embodiment of this kind, Za and Zb are advantageously identical.

According to a particular embodiment, Y1 is a $(C_1\text{-}C_6)$ alkyl or a phenyl.

According to a preferred embodiment, Y1 is selected from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl. More preferably, Y1 represents a phenyl (in particular a 1,3-phenyl) or a propyl (in particular a 1,3-propyl).

According to a particular embodiment, Y2 is a $(C_1\text{-}C_6)$ alkyl and a phenyl.

According to a preferred embodiment, Y2 is selected from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl.

According to a preferred embodiment, Y1 is joined to a peptide residue via a functional residue, the functional residue and the peptide residue optionally being separated by a spacer fragment. According to another preferred embodiment, the "Y-(functional residue)" structure, where Y is Y1 and/or Y2, preferably Y1, is:

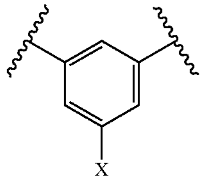

or

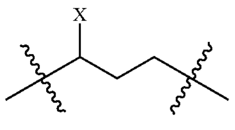

, where X represents the functional residue, in particular —CO— or —NH—, preferably —NH—, itself joined to a peptide residue, the functional residue and the peptide residue optionally being separated by a spacer fragment.

In a preferred embodiment, the monomer compound is a compound of formula (III-1), in which:

Y1 is a 1,3-propyl or a 1,3-phenyl (preferably a 1,3-phenyl); and

Za and Zb, identical or different (preferably identical), represent a methyl-O— or a group of formula (IIIa) in which Y2 is a 1,2-ethyl or a 1,4-butyl (preferably a 1,4-butyl);

and in which Y1 is joined to a peptide residue via a functional residue, the functional residue and the peptide residue optionally being separated by a spacer fragment.

In a preferred embodiment of this kind, the functional residue is advantageously —NH—, and the spacer fragment is advantageously of formula -(X1)-(X2)-(X3)- where X1 and X3 represent —CO— and X2 is a $(C_1\text{-}C_6)$alkyl, better still a 1,1-methyl or a 1,3-propyl.

In a preferred embodiment of this kind, the peptide residue is advantageously a residue of the peptide Arg-Phe-Arg-Phe-Arg-Phe-Arg-Phe, Phe-Arg-Phe-Arg-Phe-Arg-Phe-Arg, or Arg-Arg-Palm, better still Arg-Phe-Arg-Phe-Arg-Phe-Arg-Phe.

Preferably, Za and Zb represent a methyl-O—.

According to another embodiment, the monomer compound is represented by the formula (III-1), in which:

Za is a $(C_1\text{-}C_{12})$alkyl-O—, an aryl-O—, or a chlorine, preferably a $(C_1\text{-}C_{12})$alkyl-O— or an aryl-O—; and Zb is a group represented by the following formula (IIIb):

(IIIb)

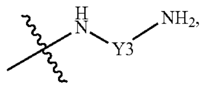

in which Y3 represents a $(C_1\text{-}C_{12})$alkyl, aryl, or polyalkylene glycol (preferably a $(C_1\text{-}C_{12})$alkyl or aryl), where at least one of Y1 and Y3 is substituted with a peptide and provided that when Y3 is joined to a peptide residue via a functional residue, Za is selected from a $(C_1\text{-}C_{12})$alkyl-O— and an aryl-O—.

According to a particular embodiment, Y1 is a $(C_1\text{-}C_6)$ alkyl or a phenyl.

According to a more particular embodiment, Y1 is selected from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl.

According to a particular embodiment, Y3 is a $(C_1\text{-}C_6)$ alkyl or a phenyl.

According to a more particular embodiment, Y3 is selected from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl.

According to a preferred embodiment, Y1 is joined to a peptide residue via a functional residue, the functional residue and the peptide residue optionally being separated by a spacer fragment.

According to this preferred embodiment, the "Y-(functional residue)" structure, where Y is Y1 and/or Y3, preferably Y1, is advantageously:

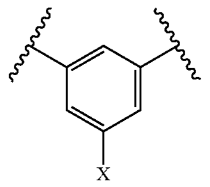

or

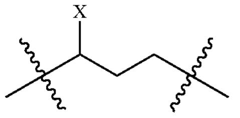

, where X represents the functional residue, in particular —CO— or —NH—, preferably NH, and preferably,

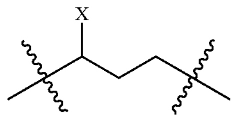

, where X represents the functional residue —NH—, said functional residue being joined to a peptide residue, and the functional residue and the peptide residue optionally being separated by a spacer fragment.

According to another preferred embodiment, Y3 is joined to a peptide residue via a functional residue, the functional residue and the peptide residue optionally being separated by a spacer fragment.

According to this preferred embodiment, the "Y-(functional residue)" structure, where Y is Y3, is advantageously

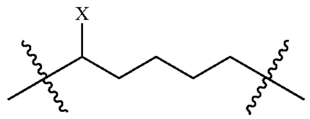

, where X represents the functional residue —CO— or —NH—, preferably —CO—, itself joined to a peptide residue, the functional residue and the peptide residue optionally being separated by a spacer fragment.

In another preferred embodiment, the monomer compound is a compound of formula (III-1), in which:

Y1 is a 1,3-propyl;

Za represents a methyl-O; and

Zb represents a group represented by the formula (IIIb) in which Y3 represents a 1,6-hexyl; and in which Y1 is joined to a peptide residue via a functional residue, the functional residue and the peptide residue optionally being separated by a spacer fragment.

In a preferred embodiment of this kind, the functional residue is advantageously —NH—, and the spacer fragment is advantageously of formula -(X1)-(X2)-(X3)- where X1 and X3 represent —CO— and —NH— respectively, and X2 is a ($C_1$-$C_6$)alkyl, better still a 1,5-pentyl.

In a preferred embodiment of this kind, the peptide residue is advantageously a residue of the peptide Arg-Phe-Arg-Phe-Arg-Phe-Arg-Phe, Phe-Arg-Phe-Arg-Phe-Arg-Phe-Arg, or Arg-Arg-Palm, better still Arg-Phe-Arg-Phe-Arg-Phe-Arg-Phe.

The present invention also relates to a monomer compound represented by the following formula (III-2):

HO—Y2-OH (III-2), in which Y2 represents a ($C_1$-$C_{12}$)alkyl, aryl or polyalkylene glycol, where Y2 is joined to a peptide residue via a functional residue, the functional residue and the peptide residue optionally being separated by a spacer fragment.

Preferably, the peptide residue is a residue of the peptide Arg-Phe-Arg-Phe-Arg-Phe-Arg-Phe, Phe-Arg-Phe-Arg-Phe-Arg-Phe-Arg, or Arg-Arg-Palm, better still Arg-Phe-Arg-Phe-Arg-Phe-Arg-Phe.

In a particular embodiment, the monomer of formula (III-1) is selected from the following formulas (M1) and (M2):

(M1)

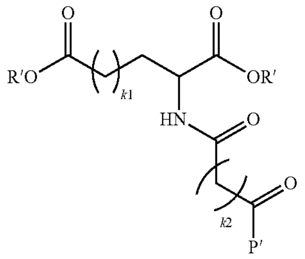

(m$^2$)

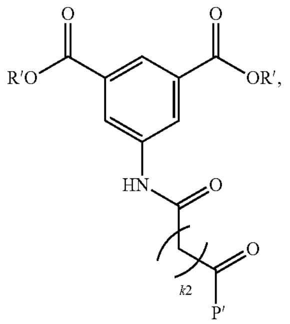

where, in each of said formulas:

k1 is an integer from 1 to 8, preferably from 1 to 4, better still k1 has a value of 1;

each k2 is an integer from 1 to 8, preferably from 1 to 6, better still k2 has a value of 3;

each R' represents independently a ($C_1$-$C_6$)-alkyl (preferably, a methyl) or a hydroxy-($C_1$-$C_{12}$)alkyl (preferably, a hydroxy-($C_1$-$C_6$)alkyl such as a 2-hydroxyethyl or a 4-hydroxybutyl);

P' represents a peptide residue, preferably a residue of the peptide Arg-Phe-Arg-Phe-Arg-Phe-Arg-Phe, Phe-Arg-Phe-Arg-Phe-Arg-Phe-Arg, or of the peptide Arg-Arg-Palm, better still a residue of the peptide Arg-Phe-Arg-Phe-Arg-Phe-Arg-Phe.

In another particular embodiment, the monomer of formula (III-1) is represented by the following formula (M3):

(M3)

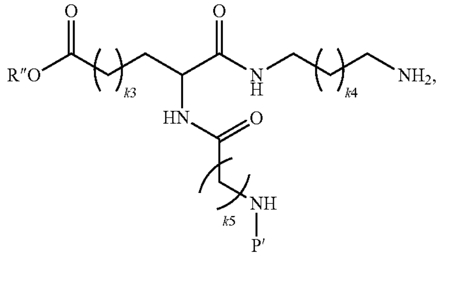

in which:

k3 is an integer from 1 to 8, preferably from 1 to 4, better still k3 has a value of 1;

k4 is an integer from 1 to 8, preferably from 1 to 4, better still k4 has a value of 4;

k5 is an integer from 1 to 8, preferably from 1 to 6, better still k5 has a value of 5;

R" is a ($C_1$-$C_6$)-alkyl, preferably a methyl;

P' represents a peptide residue, preferably a residue of the peptide Arg-Phe-Arg-Phe-Arg-Phe-Arg-Phe, Phe-Arg-Phe-Arg-Phe-Arg-Phe-Arg, or of the peptide Arg-Arg-Palm, better still of the peptide Phe-Arg-Phe-Arg-Phe-Arg-Phe-Arg.

In another particular embodiment, the monomer of formula (III-2) is represented by the following formula (M4):

(M4)

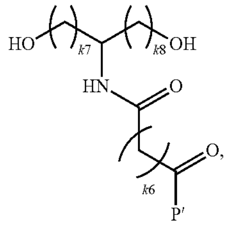

in which:

k6 is an integer from 1 to 8, preferably from 1 to 4, better still k6 has a value of 1;

k7 is an integer from 1 to 8, preferably from 1 to 4, better still k7 has a value of 1;

k8 is an integer from 1 to 8, preferably from 1 to 4, better still k8 has a value of 1;

P' represents a peptide residue, preferably a residue of the peptide Arg-Phe-Arg-Phe-Arg-Phe-Arg-Phe, Phe-Arg-Phe-Arg-Phe-Arg-Phe-Arg, or of the peptide Arg-Arg-Palm.

According to a particular embodiment, the monomer compound according to the invention is grafted on a solid support, such as a silica, an alumina, glass, a polystyrene type resin, a polyethylene glycol type resin. According to one embodiment, the monomer compound is attached to the solid support via the peptide residue.

Method for Preparing the Polymer compound

In the present application, the formula

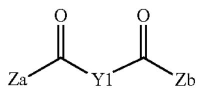

may also be written: Za-C(O)—Y1-C(O)-Zb.

The invention further relates to a method for preparing a polymer compound according to the invention, comprising a polycondensation reaction in a molten medium, involving: at least one monomer compound selected from:

a monomer compound of formula Za-C(O)—Y1-C(O)-Zb, where:

Y1 represents a radical selected from a ($C_1$-$C_{12}$)alkyl, an aryl and an aryl-($C_1$-$C_{12}$)alkaryl;

Za represents a radical selected from a ($C_1$-$C_{12}$)alkyl-O—, an aryl-O—, a chlorine, and a group of formula (IIIa):

(IIIa)

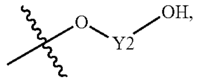

where Y2 represents a ($C_1$-$C_{12}$)alkyl, aryl, or polyalkylene glycol;

Zb represents a radical selected from a ($C_1$-$C_{12}$)alkyl-O—, an aryl-O—, a chlorine, a group of formula (IIIa) and a group of formula (IIIb);

(IIIa)

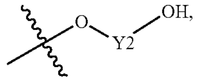

(IIIb)

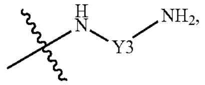

where Y2 represents a ($C_1$-$C_{12}$)alkyl, aryl, or polyalkylene glycol, and Y3 represents a ($C_1$-$C_{12}$)alkyl, aryl, or polyalkylene glycol;

OCN—Y1-NCO, where Y1 represents a ($C_1$-$C_{12}$)alkyl, aryl, or an aryl-($C_1$-$C_{12}$)alkaryl;

HO—Y2-OH, where Y2 represents a ($C_1$-$C_{12}$)alkyl, aryl or polyalkylene glycol, and $H_2N$—Y3—$NH_2$, where Y3 represents a ($C_1$-$C_{12}$)alkyl, aryl, or polyalkylene glycol;

where at least one of Y1, Y2, and Y3 is joined to a peptide residue via a functional residue, the functional residue and the peptide residue optionally being separated by a spacer fragment;

and at least one monomer compound selected from:

a monomer compound represented by the following formula (V):

(V)

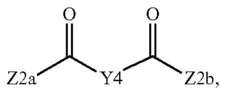

in which

Y4 represents a radical selected from a ($C_1$-$C_{12}$)alkyl, an aryl and an aryl-($C_1$-$C_{12}$)alkaryl;

Z2a represents a radical selected from:

a ($C_1$-$C_{12}$)alkyl-O—, an aryl-O—, a chlorine; and a group represented by the following formula (Va):

(Va)

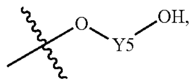

in which Y5 represents a ($C_1$-$C_{12}$)alkyl, aryl or polyalkylene glycol; and Z2b represents a radical selected from:

a $(C_1-C_{12})$alkyl-O—, an aryl-O—, a chlorine;

a group represented by the following formula (Va):

(Va)

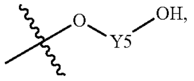

in which Y5 represents a $(C_1-C_{12})$alkyl, aryl or polyalkylene glycol; and a group represented by the following formula (Vb):

(Vb)

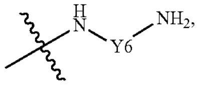

in which Y6 represents a $(C_1-C_{12})$alkyl, aryl, or polyalkylene glycol,

OCN—Y4-NCO, where Y4 represents a $(C_1-C_{12})$alkyl, aryl, or an aryl-$(C_1-C_{12})$alkaryl, HO—Y5-OH, where Y5 represents a $(C_1-C_{12})$alkyl, aryl or polyalkylene glycol and $H_2N$—Y6-$NH_2$, where Y6 represents a $(C_1-C_{12})$alkyl, aryl, or polyalkylene glycol.

In the method of the invention, Y3 and Y6 are preferably a $(C_1-C_{12})$alkyl or aryl.

In the method of the invention, preferably, when Y3 is joined to a peptide residue via a functional residue, the functional residue and the peptide residue optionally being separated by a spacer fragment, Za, Zb, Z2a and Z2b are selected, independently, from a $(C_1-C_{12})$alkyl-O— and an aryl-O—.

In a particular embodiment, the peptide residue is advantageously a residue of the peptide Arg-Phe-Arg-Phe-Arg-Phe-Arg-Phe, Phe-Arg-Phe-Arg-Phe-Arg-Phe-Arg, or Arg-Arg-Palm, better still Arg-Phe-Arg-Phe-Arg-Phe-Arg-Phe.

In a particular embodiment, said at least one monomer compound of formula Za-C(O)—Y1-C(O)-Zb used in the method according to the invention is a monomer compound of formula (III-1) as defined above.

In another particular embodiment, said at least one monomer compound of formula HO—Y2-OH used in the method according to the invention is a monomer compound of formula (III-2) as defined above.

The monomer compounds used for preparing the polymer compound of the invention are selected in such a way that they can react with one another according to a polycondensation reaction.

"Polycondensation reaction" means a polymerization reaction by adding a nucleophile onto an electrophile, optionally with elimination of a leaving group. Examples of polycondensation reaction are in particular:

polycondensation by esterification or transesterification: ester functions are created, for example by reaction between an alcohol function and a function derived from carboxylic acid such as an ester, anhydride, or acyl chloride;

polycondensation by amide coupling: reaction between an amine function and a function derived from carboxylic acid such as an ester, anhydride, or acyl chloride;

polycondensation by reaction between an alcohol or amine function, and an isocyanate function (a polycondensation involving an isocyanate function may also be called "polyaddition").

According to a particular embodiment, the method comprises a polycondensation reaction in a molten medium, involving:

at least one monomer compound of formula (III-1), in which Za and Zb represent a group of formula (IIIa), where at least one of Y1 and Y2, preferably Y1, is joined to a peptide residue via a functional residue, the functional residue and the peptide residue optionally being separated by a spacer fragment;

and at least one monomer compound of formula (V) as defined above in which Z2a and Z2b represent a group of formula (Va).

According to another particular embodiment, the method comprises a polycondensation reaction in a molten medium, involving:

at least one monomer compound of formula (III-1), in which Za and Zb represent, each independently, a $(C_1-C_{12})$alkyl-O—, aryl-O—, or chlorine, preferably a $(C_1-C_{12})$alkyl-O— or aryl-O—;

at least one HO—Y2-OH;

where at least one of Y1 and Y2, preferably Y1, is joined to a peptide residue via a functional residue, the functional residue and the peptide residue optionally being separated by a spacer fragment;

at least one monomer compound of formula (V), in which Z2a and Z2b each represent a $(C_1-C_{12})$alkyl-O—, aryl-O—, or chlorine, preferably a $(C_1-C_{12})$alkyl-O— or aryl-O—; and, at least one HO—Y5-OH.

According to a particular embodiment, Y1, Y2, Y4, and Y5 represent, each independently, a $(C_1-C_{12})$alkyl, such as an ethyl, a propyl, a butyl, a pentyl, or a hexyl.

According to another particular embodiment, Y1, Y2, Y4, and Y5 represent, each independently, an aryl, such as a phenyl.

According to another particular embodiment, Y1 and Y4 are identical.

According to another particular embodiment, Y2 and Y5 are identical. Preferably, Y2 and Y5 represent a $(C_1-C_6)$ alkyl, more preferably a 1,2-ethyl or a 1,4-butyl, better still a 1,4-butyl.

According to a particular embodiment, Y1, Y2, Y4 and Y5 are selected, independently, from a $(C_1-C_6)$alkyl and a phenyl.

According to a more particular embodiment, Y1, Y2, Y4 and Y5 are selected, independently, from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl.

According to a particular embodiment, Y1 and/or Y2 are selected, independently, from a $(C_1-C_6)$alkyl and a phenyl, in particular from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl.

According to a preferred embodiment, Y1 is joined to a peptide residue via a functional residue, the functional residue and the peptide residue optionally being separated by a spacer fragment.

According to a preferred embodiment, Y1 represents a phenyl (in particular a 1,3-phenyl) or a propyl (in particular a 1,3-propyl).

According to another preferred embodiment, the "Y-(functional residue)" structure, where Y is Y1 and/or Y2, preferably Y1, is:

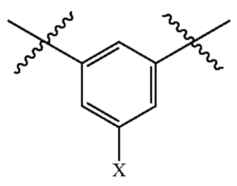
or
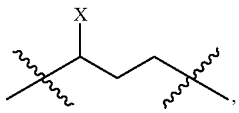
, where X represents the functional residue, in particular —CO— or —NH—, preferably —NH—, itself joined to a peptide residue, the functional residue and the peptide residue optionally being separated by a spacer fragment.

According to another more particular embodiment, the method comprises a polycondensation reaction in a molten medium, involving:

a monomer compound of formula (III-1), in which Y1 represents a $(C_1-C_{12})$alkyl or an aryl, and Za and Zb represent a $(C_1-C_{12})$alkyl-O—;

where Y1 is joined to a peptide residue via a functional residue, the functional residue and the peptide residue optionally being separated by a spacer fragment;

at least one monomer compound of formula (V), in which Y4 is a $(C_1-C_{12})$alkyl or an aryl, and Z2a and Z2b represent a $(C_1-C_{12})$alkyl-O—; and, at least one compound of formula HO—$(C_1-C_{12})$alkyl-OH or HO-aryl-OH, preferably of formula HO—$(C_1-C_{12})$alkyl-OH.

In said particular embodiment, the functional residue is advantageously —NH—, and the spacer fragment is advantageously of formula -(X1)-(X2)-(X3)- where X1 and X3 represent —CO— and X2 is a $(C_1-C_6)$alkyl.

Preferably, the method comprises a polycondensation reaction in a molten medium, involving:

a monomer compound of formula (III-1), in which Y1 represents a 1,3-propyl or a 1,3-phenyl (better, a 1,3-phenyl), Za and Zb represent a methyl-O—;

where Y1 is joined to a peptide residue via a functional residue, the functional residue and the peptide residue optionally being separated by a spacer fragment;

at least one monomer compound of formula (V), in which Y4 is a 1,4-phenyl, 1,2-ethyl or a 1,4-butyl, Z2a and Z2b represent a methyl-O—; and, ethane-1,2-diol or butane-1,4-diol, preferably butane-1,4-diol.

In said particular embodiment, the functional residue is advantageously —NH—, and the spacer fragment is advantageously of formula -(X1)-(X2)-(X3)- where X1 and X3 represent —CO— and X2 is a $(C_1-C_6)$alkyl, better still a 1,1-methyl or a 1,3-propyl.

According to another particular embodiment, the method comprises a polycondensation reaction in a molten medium, involving:

at least one monomer compound of formula (III-1), in which:

Za is a $(C_1-C_{12})$alkyl-O—, an aryl-O—, or a chlorine, preferably a $(C_1-C_{12})$alkyl-O- or aryl-O—; and Zb is a group of formula (IIIb);

where at least one of Y1 and Y3, preferably Y1 or Y3, is substituted with a peptide and provided that when Y3 is joined to a peptide residue via a functional residue, the functional residue and the peptide residue optionally being separated by a spacer fragment, Za is selected from a $(C_1-C_{12})$alkyl-O— and an aryl-O—, and at least one monomer compound of formula (V) as defined above in which:

Z2a is a $(C_1-C_{12})$alkyl-O—, an aryl-O—, or a chlorine, preferably a $(C_1-C_{12})$alkyl-O— or aryl-O—; and Z2b is a group of formula (Vb);

provided that when Y3 is joined to a peptide residue via a functional residue, the functional residue and the peptide residue optionally being separated by a spacer fragment, Za, Zb, Z2a and Z2b are selected, independently, from a $(C_1-C_{12})$alkyl-O— and an aryl-O—.

In said particular embodiment, said at least one monomer compound of formula Za-C(O)—Y1-C(O)-Zb may in particular be a monomer of formula (M3) as defined above.

According to another particular embodiment, the method comprises a polycondensation reaction in a molten medium, involving:

least one monomer compound of formula Za-C(O)—Y1-C(O)-Zb, in which Za and Zb represent, each independently, a $(C_1-C_{12})$alkyl-O—, aryl-O—, or a chlorine, preferably a $(C_1-C_{12})$alkyl-O— or aryl-O—;

at least one $H_2N$—Y3—$NH_2$;

where at least one of Y1 and Y3, preferably Y1 or Y3, is joined to a peptide residue via a functional residue, the functional residue and the peptide residue optionally being separated by a spacer fragment;

at least one monomer compound of formula (V), in which Z2a and Z2b each represent a $(C_1-C_{12})$alkyl-O—, aryl-O—, or a chlorine, preferably a $(C_1-C_{12})$alkyl-O— or aryl-O—; and, at least one $H_2N$—Y6-$NH_2$;

provided that when Y3 is joined to a peptide residue via a functional residue, the functional residue and the peptide residue optionally being separated by a spacer fragment, Za, Zb, Z2a and Z2b are selected, independently, from a $(C_1-C_{12})$alkyl-O— and an aryl-O—.

According to a particular embodiment, Y1, Y3, Y4, and Y6 represent, each independently, a $(C_1-C_{12})$alkyl, such as an ethyl, a propyl, a butyl, a pentyl, or a hexyl.

According to another particular embodiment, Y1, Y3, Y4, and Y6 represent, each independently, an aryl, such as a phenyl.

According to another particular embodiment, Y1 and Y4 are identical.

According to another particular embodiment, Y3 and Y6 are identical.

According to a particular embodiment, Y1, Y3, Y4 and Y6 are selected, independently, from a $(C_1-C_6)$alkyl and a phenyl.

According to a more particular embodiment, Y1, Y3, Y4 and Y6 are selected, independently, from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl.

According to a particular embodiment, Y1 and/or Y3 are selected, independently, from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl.

According to a preferred embodiment, Y1 is joined to a peptide residue via a functional residue, the functional residue and the peptide residue optionally being separated by a spacer fragment. According to this preferred embodiment, the "Y-(functional residue)" structure, where Y is Y1, is advantageously:

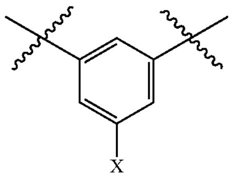
or
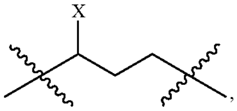, where X represents the functional residue, in particular —CO— or —NH—, preferably NH, and preferably,

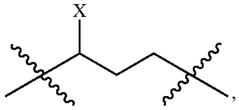, where X represents the functional residue —NH—, said functional residue being joined to a peptide residue, and the functional residue and the peptide residue optionally being separated by a spacer fragment.

According to another preferred embodiment, Y3 is joined to a peptide residue via a functional residue, the functional residue and the peptide residue optionally being separated by a spacer fragment.

According to this preferred embodiment, the "Y-(functional residue)" structure, where Y is Y3, is advantageously

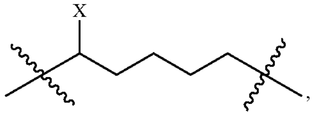, where X represents the functional residue —CO— or —NH—, preferably —CO—, itself joined to a peptide residue, the functional residue and the peptide residue optionally being separated by a spacer fragment.

In another particular embodiment, the method comprises a polycondensation reaction in a molten medium, involving:

- at least one compound OCN—Y1-NCO where Y1 represents a $(C_1\text{-}C_{12})$alkyl, aryl or aryl-$(C_1\text{-}C_{12})$alkaryl (preferably an aryl-$(C_1\text{-}C_{12})$alkaryl),
- at least one compound HO—Y2-OH where Y2 represents a $(C_1\text{-}C_{12})$alkyl, aryl, or polyalkylene glycol,
- optionally, at least one compound $H_2N$—Y3—$NH_2$ where Y3 represents a $(C_1\text{-}C_{12})$alkyl, aryl, or polyalkylene glycol,
- at least one compound OCN—Y4-NCO, where Y4 represents a $(C_1\text{-}C_{12})$alkyl, aryl, or aryl-$(C_1\text{-}C_{12})$alkaryl (preferably an aryl-$(C_1\text{-}C_{12})$alkaryl),
- at least one compound HO—Y5-OH, where Y5 represents a $(C_1\text{-}C_{12})$alkyl, aryl or polyalkylene glycol, and
- optionally $H_2N$—Y6-$NH_2$, where Y6 represents a $(C_1\text{-}C_{12})$alkyl, aryl, or polyalkylene glycol; where Y2 and/or Y3, preferably Y2 only, is joined to a peptide residue via a functional residue, the functional residue and the peptide residue optionally being separated by a spacer fragment.

In a more particular embodiment, the method comprises a polycondensation reaction in a molten medium, involving:

- at least one compound OCN—Y1-NCO where Y1 represents a $(C_1\text{-}C_{12})$alkyl, aryl or an aryl-$(C_1\text{-}C_{12})$alkaryl,
- at least one compound of formula (III-2) as defined above,
- optionally, at least one compound $H_2N$—Y3—$NH_2$ where Y3 represents a $(C_1\text{-}C_{12})$alkyl, aryl, or polyalkylene glycol,
- at least one compound OCN—Y4-NCO, where Y4 represents a $(C_1\text{-}C_{12})$alkyl, aryl, or an aryl-$(C_1\text{-}C_{12})$alkaryl),
- at least one compound HO—Y5-OH, where Y5 represents a $(C_1\text{-}C_{12})$alkyl, aryl, or polyalkylene glycol,
- optionally $H_2N$—Y6-$NH_2$, where Y6 represents a $(C_1\text{-}C_{12})$alkyl, aryl, or polyalkylene glycol where Y2 is joined to a peptide residue via a functional residue, the functional residue and the peptide residue optionally being separated by a spacer fragment.

Preferably, Y1 and Y4 are identical.

According to a particular embodiment, Y1 is selected from a 1,2-ethyl, a 1,3-propyl, a 1,4-butyl, a 1,5-pentyl, a 1,6-hexyl, a 1,3-phenyl, a 1,4-phenyl, and a phenyl-methyl-phenyl.

According to another particular embodiment, Y2 is selected from a 1,2-ethyl, a 1,3-propyl, a 1,4-butyl, a 1,5-pentyl, a 1,6-hexyl, a 1,3-phenyl, a 1,4-phenyl, a polyethylene glycol and a polybutylene glycol.

According to another particular embodiment, Y3 is selected from a 1,2-ethyl, a 1,3-propyl, a 1,4-butyl, a 1,5-pentyl, a 1,6-hexyl, a 1,3-phenyl, a 1,4-phenyl.

According to another particular embodiment, Y4 is selected from a 1,2-ethyl, a 1,3-propyl, a 1,4-butyl, a 1,5-pentyl, a 1,6-hexyl, a 1,3-phenyl, a 1,4-phenyl, and a phenyl-methyl-phenyl.

According to another particular embodiment, Y5 is selected from a 1,2-ethyl, a 1,3-propyl, a 1,4-butyl, a 1,5-pentyl, a 1,6-hexyl, a 1,3-phenyl, a 1,4-phenyl, a polyethylene glycol and a polybutylene glycol.

According to another particular embodiment, Y6 is selected from a 1,2-ethyl, a 1,3-propyl, a 1,4-butyl, a 1,5-pentyl, a 1,6-hexyl, a 1,3-phenyl, and a 1,4-phenyl.

In another embodiment, the method comprises a polycondensation reaction in a molten medium, involving:

- at least one monomer compound of formula (III-1), in which Za and Zb represent a group of formula (IIIa), where at least one of Y1 and Y2, preferably Y1, is joined to a peptide residue via a functional residue, the functional residue and the peptide residue optionally being separated by a spacer fragment,
- at least one OCN—Y4-NCO, where Y4 represents a $(C_1\text{-}C_{12})$alkyl, aryl or aryl-$(C_1\text{-}C_{12})$alkaryl (preferably an aryl-$(C_1\text{-}C_{12})$alkaryl),
- at least one HO—Y5-OH, where Y5 represents a $(C_1\text{-}C_{12})$alkyl, aryl, or polyalkylene glycol, and
- optionally at least one $H_2N$—Y6-$NH_2$, where Y6 represents a $(C_1\text{-}C_{12})$alkyl, aryl, or polyalkylene glycol.

preferably, said at least one HO—Y5-OH is a mixture of an HO—Y5-OH, where Y5 represents a $(C_1\text{-}C_{12})$alkyl (for example a 1,4-butyl) and of an HO—Y5-OH, where Y5 represents a polyalkylene glycol (preferably, polybutylene glycol).

In another embodiment, the method comprises:

(a) a first step of polycondensation reaction in a molten medium to form a first polymer compound, involving:
- at least one monomer compound of formula (III-1), in which Za and Zb represent, each independently, a $(C_1\text{-}C_{12})$alkyl-O—, aryl-O—, or chlorine, preferably a $(C_1\text{-}C_{12})$alkyl-O— or aryl-O—;
- at least one HO—Y2-OH, where Y2 represents a $(C_1\text{-}C_{12})$alkyl, aryl or polyalkylene glycol; where at least one of Y1 and Y2, preferably Y1, is joined to a peptide residue via a functional residue, the functional residue and the peptide residue optionally being separated by a spacer fragment; and at least one monomer compound of formula (V), in which Z2a and Z2b each represent a $(C_1\text{-}C_{12})$alkyl-O—, aryl-O—, or chlorine, preferably a $(C_1\text{-}C_{12})$alkyl-O— or aryl-O—; and, at least one HO—Y5-OH where Y5 represents a $(C_1\text{-}C_{12})$ alkyl, aryl or polyalkylene glycol; (b) a second step of polycondensation reaction in a molten medium to form a second polymer compound, involving:

the first polymer compound obtained in step (a);

at least one compound OCN—Y4-NCO, where Y4 represents a $(C_1\text{-}C_{12})$alkyl, aryl, or aryl-$(C_1\text{-}C_{12})$alkaryl (preferably an aryl-$(C_1\text{-}C_{12})$alkaryl), optionally at least one HO—Y5-OH, where Y5 represents a $(C_1\text{-}C_{12})$alkyl, aryl or polyalkylene glycol, and optionally at least one $H_2N$—Y6-$NH_2$, where Y6 represents a $(C_1\text{-}C_{12})$alkyl, aryl, or polyalkylene glycol.

In the method according to the invention, the weight ratio of the monomer compounds joined to a peptide residue, to all of the monomer compounds, is advantageously between 0.0001/100 and 50/100, preferably between 0.001/100 and 10/100, better still between 0.005/100 and 1/100, or even between 0.0075/100 and 0.1/100.

The monomers used in the polycondensation reaction are mixed without solvent, or are dissolved in a solvent, such as DMF, DMSO, or dichloromethane, or a mixture thereof. In these conditions, the polymer compound generally precipitates, and may be isolated, in particular by filtration. The polycondensation reaction may be carried out in the presence of a catalyst and/or a base, generally soluble in the reaction solvent(s). Examples of bases are in particular diisopropylethylamine (DIPEA) or triethylamine. Examples of catalysts are in particular a titanium(IV) complex such as titanium tetrabutanolate, tin dioctyl dilaurate, bismuth-based catalysts, or tertiary amine catalysts such as 1,8-diazabicyclo [5.4.0]undec-7-ene (DBU).

In a particular embodiment, the polycondensation reaction of the method for preparing the polymer compound is carried out by:

(i) bringing into contact the monomer compounds used in the polycondensation reaction (i.e., the monomer compounds of formula Za-C(O)—Y1-C(O)-Zb, HO—Y2-OH, of formula (V), $H_2N$—Y3—$NH_2$, HO—Y5-OH, $H_2N$—Y6-$NH_2$, in the presence of a polycondensation catalyst (in particular a titanium(IV) complex such as titanium tetrabutanolate);

(ii) heating the mixture obtained in step (i) at a temperature between 100 °C and 200 °C, at a pressure between 500 mbar and 1.5 bar;

(iii) heating the mixture obtained in step (ii) at a temperature between 100 °C and 200 °C, at a pressure between 0.1 mbar and 200 mbar; and (iv) recovering the polymer compound, for example by precipitation by means of one or more suitable organic solvents (such as a mixture of dichloromethane and methanol) and filtration.

Steps (i) to (iii) are advantageously carried out in an inert atmosphere (for example, in an atmosphere of nitrogen or argon).

The method of the invention may be carried out either in batch mode, for example in a closed reactor, or continuously, for example by reactive extrusion. The polymer compound of the invention may be formed by any technique known by a person skilled in the art. The polymer compound of the invention may be formed during the polymerization process, or after the polymerization process, especially if it is obtained in the form of granules or plates. The polymer compound may in particular be prepared in the form of threads, fibers, or as a molding.

Method for Preparing the Monomer Compound

The monomer compound according to the invention is prepared advantageously by a method on a solid support.

According to a first embodiment, the method for preparing a monomer according to the invention comprises:

(a) supplying a peptide grafted on a solid support;

(b) optionally reacting a functional group of the peptide grafted in step (a) with a first functional group of a spacer;

(c) reacting a coupling function joined to a compound A of formula selected from the following formulas:

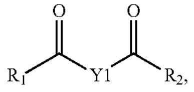

HO—Y2-OH, or $H_2N$—Y3-$NH_2$, in which Y1 represents a $(C_1\text{-}C_{12})$alkyl, an aryl or aryl-$(C_1\text{-}C_{12})$alkaryl, Y2 represents a $(C_1\text{-}C_{12})$alkyl, an aryl, or polyalkylene glycol, Y3 represents a $(C_1\text{-}C_{12})$alkyl, an aryl, or polyalkylene glycol, $R_1$ and $R_2$ represent, each independently, a chlorine, a hydroxy, a $(C_1\text{-}C_{12})$alkyl-O—, or an aryl-O—, and said coupling function is joined to Y1, Y2 or Y3;

with a functional group of the peptide grafted in step (a) or with a second functional group of the spacer provided in step (b); and, (d) removing the solid support from the compound thus obtained;

the method optionally comprising a step (x) of reaction of at least one compound B of formula selected from the following formulas:

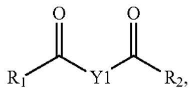

HO—Y2-OH, or $H_2N$—Y3-$NH_2$, in which

Y1 represents a $(C_1\text{-}C_{12})$alkyl, an aryl or aryl-$(C_1\text{-}C_{12})$ alkaryl, Y2 represents a $(C_1\text{-}C_{12})$alkyl, an aryl, or polyalkylene glycol, Y3 represents a $(C_1\text{-}C_{12})$alkyl, an aryl, or polyalkylene glycol, $R_1$ and $R_2$ represent, each independently, a chlorine, a hydroxy, a $(C_1\text{-}C_{12})$alkyl-O—, or an aryl-O—, with the compound obtained in step (c) or (d); and in which the compounds A and B are selected in such a way that they can react with one another according to a condensation reaction.

"Condensation reaction" means an addition reaction of a nucleophile on an electrophile, with elimination of a leaving group. The condensation reaction is typically a reaction of addition-elimination. Examples of condensation reaction are in particular:

esterification: reaction between an alcohol function and a carboxylic acid function or a function derived from carboxylic acid such as an ester, anhydride, or acyl chloride; or amide coupling: reaction between an amine function and a carboxylic acid function or a function derived from carboxylic acid such as an ester, anhydride, or acyl chloride.

According to a particular embodiment, the method comprises:

(a) supplying a peptide grafted on a solid support;

(b) optionally reacting a functional group of the peptide grafted in step (a) with a first functional group of a spacer;

(c) reacting a coupling function joined to a compound A of formula:

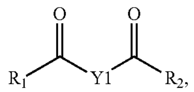

in which Y1 represents a ($C_1$-$C_{12}$)alkyl, an aryl, or aryl-($C_1$-$C_{12}$)alkaryl, $R_1$ and $R_2$ represent, each independently, a chlorine, a hydroxy, a ($C_1$-$C_{12}$)alkyl-O—, or an aryl-O—, and where said coupling function is joined to Y1;

with a functional group of the peptide grafted in step (a) or with a second functional group of the spacer provided in step (b);

(d) removing the solid support from the compound obtained in step (c) or (x); the method optionally comprising a step (x) of reaction of a compound B of formula HO—Y2-OH, or $H_2N$—Y3-$NH_2$, in which Y2 is a ($C_1$-$C_{12}$)alkyl, an aryl, or polyalkylene glycol, and Y3 is a ($C_1$-$C_{12}$)alkyl, an aryl, or polyalkylene glycol, with the compound obtained in step (c) or (d); and in which the compounds A and B are selected in such a way that they can react with one another according to a condensation reaction.

According to a particular embodiment, compound B is of formula HO—Y2-OH. In a particular embodiment of this kind, the groups $R_1$ and $R_2$ of compound A are advantageously identical, and are selected from a ($C_1$-$C_{12}$)alkyl-O— and an aryl-O, preferably a ($C_1$-$C_{12}$)alkyl-O— such as a methyl-O—.

According to another particular embodiment, compound B is of formula $H_2N$—Y3-$NH_2$. In a particular embodiment of this kind, the groups $R_1$ and $R_2$ of compound A are selected from a hydroxy, ($C_1$-$C_{12}$)alkyl-O— and an aryl-O, and at least one of $R_1$ and $R_2$ is a ($C_1$-$C_{12}$)alkyl-O— or an aryl-O. In an embodiment of this kind, preferably, one of $R_1$ and $R_2$ is a hydroxy, and the other of $R_1$ and $R_2$ is a ($C_1$-$C_{12}$)alkyl-O— or an aryl-O, preferably a ($C_1$-$C_{12}$)alkyl-O— such as a methyl-O—.

Y1 may in particular be selected from a ($C_1$-$C_6$)alkyl, in particular from an ethyl, a propyl, a butyl, a pentyl, a hexyl, and a phenyl, preferably from a 1,2-ethyl, 1,3-propyl, 1,4-butyl, 1,5-pentyl, 1,6-hexyl, 1,2-phenyl, 1,3-phenyl and 1,4-phenyl. More particularly, Y1 may be a phenyl (in particular a 1,3-phenyl) or a propyl (in particular a 1,3-propyl). Y2 may in particular be selected from an ethyl, a propyl, a butyl, a pentyl, a hexyl, a phenyl, a polyethylene glycol, a polypropylene glycol, and a polybutylene glycol, preferably from a 1,2-ethyl, 1,3-propyl, 1,4-butyl, 1,5-pentyl, 1,6-hexyl, 1,2-phenyl, 1,3-phenyl and 1,4-phenyl, better still Y2 is a 1,2-ethyl or a 1,4-butyl.

The "Y1-(coupling function)" structure is preferably:

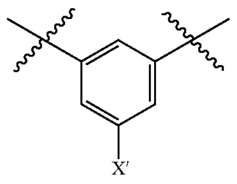

or

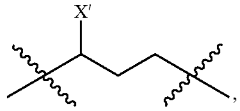

, where X' represents the coupling function, in particular —$CO_2H$ (or a derivative of $CO_2H$) or —$NH_2$, preferably —$NH_2$.

According to a particular embodiment, step (x) is not carried out. In an embodiment of this kind, step (d) comprises removal of the solid support from the compound obtained in step (c).

According to another embodiment, step (x) is carried out after step (c) and before step (d). In an embodiment of this kind, step (x) comprises reaction of said compound B with the compound obtained in step (c), and step (d) comprises removal of the solid support from the compound obtained in step (x).

According to another embodiment, step (x) is carried out after step (d). In an embodiment of this kind, step (d) comprises removal of the solid support from the compound obtained in step (c), and step (x) comprises reaction of said compound B with the compound obtained in step (d).

According to another particular embodiment, the method comprises:

(a) supplying a peptide grafted on a solid support;

(b) optionally reacting a functional group of the peptide grafted in step (a) with a first functional group of a spacer;

(c) reacting a coupling function joined to a compound A of formula HO—Y2-OH, or $H_2N$—Y3-$NH_2$, in which Y2 is a ($C_1$-$C_{12}$)alkyl, an aryl, or polyalkylene glycol, and Y3 is a ($C_1$-$C_{12}$)alkyl, an aryl, or polyalkylene glycol, said coupling function is joined to Y2 or Y3;

with a functional group of the peptide grafted in step (a) or with a second functional group of the spacer provided in step (b);

(x) reacting a compound B of formula:

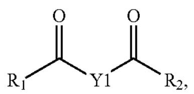

in which Y1 represents a ($C_1$-$C_{12}$)alkyl, an aryl or aryl-($C_1$-$C_{12}$)alkaryl, Y2 represents a ($C_1$-$C_{12}$)alkyl, an aryl, or polyalkylene glycol, Y3 represents a ($C_1$-$C_{12}$)alkyl, an aryl, or polyalkylene glycol, $R_1$ and $R_2$ represent, each independently, a chlorine, a hydroxy, a ($C_1$-$C_{12}$)alkyl-O—, or an aryl-O—, with the compound obtained in step (c); and (d) removing the solid support from the compound obtained in step (x);

in which the compounds A and B are selected in such a way that they can react with one another according to a condensation reaction.

According to a second embodiment, the method for preparing a monomer according to the invention comprises:

(a') grafting a compound A' of the following formula on a solid support

HO—Y2-OH or $H_2N$—Y3-$NH_2$, in which Y2 is a ($C_1$-$C_{12}$)alkyl, an aryl, or polyalkylene glycol and Y3 is a ($C_1$-$C_{12}$)alkyl, an aryl, or polyalkylene glycol;

(b') the condensation reaction of a compound B' of formula:

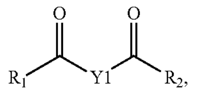

in which Y1 represents a ($C_1$-$C_{12}$)alkyl, an aryl or aryl-($C_1$-$C_{12}$)alkaryl, $R_1$ and $R_2$ represent, each independently, a chlorine, a hydroxy, a ($C_1$-$C_{12}$)alkyl-O—, or an aryl-O—, with compound A' grafted in step (a');

where a coupling function is joined to at least one of Y1, Y2 and Y3, preferably joined to Y1;

(c') reaction of said coupling function joined to at least one of Y1, Y2 and Y3, with a functional group of a peptide or with a first functional group of a spacer;

(d') optionally, reaction of a second functional group of the spacer provided in step (c') with a functional group of a peptide; and (e') removing the solid support from the compound obtained in step (c') or (d').

According to a preferred embodiment, compound A' is of formula $H_2N$—Y3-$NH_2$ in which Y3 represents a ($C_1$-$C_{12}$) alkyl (preferably a 1,6-hexyl), and compound B' is of formula:

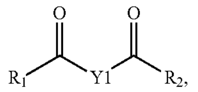

in which Y1 represents a ($C_1$-$C_{12}$)alkyl (preferably a 1,3-propyl), and $R_1$ and $R_2$ represent, each independently, a ($C_1$-$C_{12}$)alkyl-O— (preferably a methyl-O—) or a hydroxy (preferably, one of R1 and $R_2$ is a hydroxy and the other is a ($C_1$-$C_{12}$)alkyl-O—). In an embodiment of this kind, the coupling function is advantageously joined to Y1, and is preferably —$NH_2$ or a protected form of —$NH_2$ (for example —NH-Fmoc). An example of "Y1-(coupling function)" structure is:

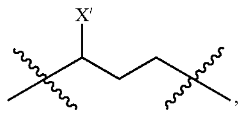

where X' represents the coupling function —$NH_2$ or a protected form thereof, such as —NHFmoc.

According to a particular embodiment, the spacer is of formula X-(X2)-X', in which X and X' represent independently —$NH_2$, —$CO_2$H or a derivative of —$CO_2$H (in particular an ester (e.g. —$CO_2$R where R is an alkyl or aryl) or an acyl halide), or together form an anhydride, and X2 represents a ($C_1$-$C_{12}$)alkyl, aryl, or a polyalkylene glycol, preferably a ($C_1$-$C_6$)alkyl, better still a methyl or propyl (e.g. 1,3-propyl).

According to a particular embodiment, X and X' are a —$CO_2$H, a derivative of —$CO_2$H, or together form an anhydride.

According to another particular embodiment, X is —$NH_2$ and X' is a —$CO_2$H or a derivative of —$CO_2$H.

According to a particular embodiment, $R_1$ and $R_2$ represent independently a ($C_1$-$C_{12}$)alkyl-O— or an aryl-O—, better still a ($C_1$-$C_{12}$)alkyl-O—, such as a methyl-O—. According to another particular embodiment, $R_1$ and $R_2$ are identical.

The solid support may in particular be a silica, an alumina, glass, a polystyrene type resin, a polyethylene glycol type resin. The solid support may be a support functionalized with a chemical group suitable for peptide synthesis, for example a resin functionalized with a group 4-((2,4-dimethoxyphenyl)(Fmoc-amino)methyl)phenoxyalkyl (e.g. Rink-Amide® Resin) or with a 2-chlorotrityl chloride group.

The reaction of each of steps (b), (c), (x), (b'), (c') and (d') is advantageously a condensation reaction, and is preferably carried out in the presence of a base and optionally a coupling agent. Examples of bases are in particular an amine, such as diisopropylethylamine (DIEA), or a pyridine such as dimethylaminopyridine (DMAP).

Nonlimiting examples of coupling agents are in particular those used in peptide synthesis, such as N-ethyl-N' carbodiimide (EDC), O-(7-azabenzotriazol-1-yl)-tetramethyluronium hexafluorophosphate (HATU), or benzotriazole-tetramethyluronium hexafluorophosphate (HBTU).

The reaction conditions such as amount of coupling agent or of base, temperature, and the solvent may be selected appropriately by a person skilled in the art.

Removal of the support in step (d) or in step (e') may in particular be carried out in the presence of an acid, such as trifluoroacetic acid (TFA), and a silane, such as triisopropylsilane (TIS) in a suitable solvent.

In a particular embodiment, the compounds of formula $H_2N$—Y3-$NH_2$ or HO—Y2-OH, more particularly $H_2N$—Y3-$NH_2$, may be used in a protected form. "Protected form" means a form of the compound in which one or more reactive functions have been converted to an unreactive function by introducing a protective group (protection reaction).

Examples of protective groups for a reactive function $NH_2$ or OH are in particular the group Boc (tert-butoxycarbonyl), Fmoc (fluorenylmethoxycarbonyl), NVoc (nitroveratryloxycarbonyl), Alloc (allyloxycarbonyl), Troc (trichloroethoxycarbonyl), Cbz (carboxybenzyl), trityl, THP (tetrahydropyranyl), or a silylated group such as TBS (tert-butyldimethylsilyl) or TMS (trimethylsilyl).

A suitable protective group and conditions for protection of one or more reactive functions may be selected appropriately by a person skilled in the art.

Deprotection consists of removing the protective group from one or more reactive functions, with the aim of restoring its reactivity. Deprotection may be carried out during or between any steps of the method for preparing the monomer compound. The conditions for deprotection of one or more protected reactive functions may be selected appropriately by a person skilled in the art.

According to a particular embodiment, several reactive functions of a compound of formula $H_2N$—Y3-$NH_2$ or HO—Y2-OH (more particularly $H_2N$—Y3-$NH_2$) are protected, and the corresponding protective groups are identical to or different than one another. Preferably, these protective groups are different, or even orthogonal relative to one another. Orthogonality makes it possible to protect or deprotect selectively different functions of one and the same compound. Two orthogonal protective groups are in particular Boc and Fmoc.

Uses

The present invention also relates to the use of a polymer compound of the invention in the manufacture of a material.

The invention further relates to a material comprising a polymer compound of the invention.

In a particular embodiment, said material is a biomaterial, and preferably an antibacterial material or biomaterial.

In another embodiment, said material is a detection material, more precisely a material that reacts to an environmental change, such as a biosensor. In an embodiment of this kind, the presence of peptides grafted on the polymer compound, in particular bioactive peptides, allows the material to be used as a detection material such as a biosensor.

In another embodiment, said material is absorbable, or even bioabsorbable.

Said material may in particular be an antibacterial, anti-inflammatory, biocidal and/or fungicidal material.

The present invention also relates to the use of a polymer compound of the invention in the manufacture of an article.

The invention further relates to an article comprising a polymer compound of the invention, such as a medical device or a fabric.

Said article advantageously has antibacterial, anti-inflammatory, biocidal and/or fungicidal properties.

Said article may in particular be a thread, a fiber, a fabric, a filter for body fluids, a suture, a catheter, a dressing or an implantable device. Examples of fabrics are in particular a sock, a sole, a stocking, a jacket, a shirt or a blouse.

Said article may in particular be a stopper, a seal, a capsule, a cover, or a tap. Said article may be some or all of bottles, flasks, pots, boxes, cans, barrels, tanks and various containers used for packaging and/or storage of food, dietary, cosmetic, dermatological or pharmaceutical products. Said article may be an article suitable for storage and/or distribution of pharmaceutical products (for example, spoons for sirup, syringes for administering for example a sirup, blister packs for tablets or capsules, infusion bags, tubes, cannulas, pumps and vials) or food (for example, trays, lids and packaging films).

Said article or said material according to the invention may be used for the manufacture of operating room equipment, sterile room equipment, surgical instruments, or a laboratory bench (work surface).

EXAMPLES

The invention will be better understood from the following examples, which are given purely for illustration and are not intended to limit the scope of the invention, which is defined by the accompanying claims.

A. Preparation of the Monomers Substituted with a Peptide

The peptides are synthesized on a solid support using a peptide synthesizer of the Symphony X type (Protein Technologies, Inc., USA) by Fmoc/tert-butyl strategy using nitrogen bubbling as the method of agitation for the cycles of coupling and deprotection of the Fmoc groups in N-terminal position.

The syntheses are carried out at a scale of 0.25 mmol on Fmoc-Rink-Amide polystyrene resin (481 mg/0.52 mmol/g) or 2-chlorotrityl chloride (892 mg, 0.28 mmol/g). The standard cycle of deprotection-coupling for each residue comprises six steps: Washing the resin with 5 ml of DMF (3×30 s). Deprotection of the Fmoc group with 5 ml of piperidine at 20% in DMF (3×3 min). Washing the resin with 5 mL of DMF (3×30 s). Coupling of the Fmoc-AA residue for 60 min using HATU and DIEA as coupling agent. At the end of the coupling cycle, a capping step is carried out with 5 mL of Ac2O at 10% in DMF for 7 min, and then the resin is washed with 5 mL of DMF (3×30 s).

Cleavage of the resin (Fmoc-Rink-Amide) is carried out 2×60 minutes in a cleavage cocktail (TFA/TIS/$H_2O$ 95/2.5/2.5) for the deprotected sequences and 2×60 minutes in a cleavage cocktail (AcOH/TFE/DCM 10/20/70) for the protected sequences (2-chlorotrityl chloride resin). Once the resin has been filtered, the solution is evaporated under vacuum and the peptide is precipitated in diethyl ether. The precipitated peptide is centrifuged (3500 RCF) and the supernatant is removed. (X3). The peptide in the form of TFA salts is then dissolved in $H_2O$/ACN mixture before being frozen and lyophilized.

The peptides are analyzed by UPLC and mass spectrometry ESI-MS, equipped with a BEH $C_{18}$ column (WATERS), 150*2.1 mm (150×2.1 mm) (flow rate: 0.6 ml/min). Solvents A and B are 0.1% of TFA in water and 0.1% of TFA in acetonitrile.

Purification of the peptides is carried out on WATERS HPLC 4000 apparatus equipped with a UV 486 detector and a Vydac Denali column 10 μm C18 120 Å (310×25 mm) at a flow rate of 50 ml/min. The solvents used are 0.1% of TFA in water (buffer A) and 0.1% of TFA in acetonitrile (buffer B).

Example 1: Preparation of Dimethyl Isophthalate Monomers Substituted with a Peptide a) Peptide: H—(RF)4—$NH_2$

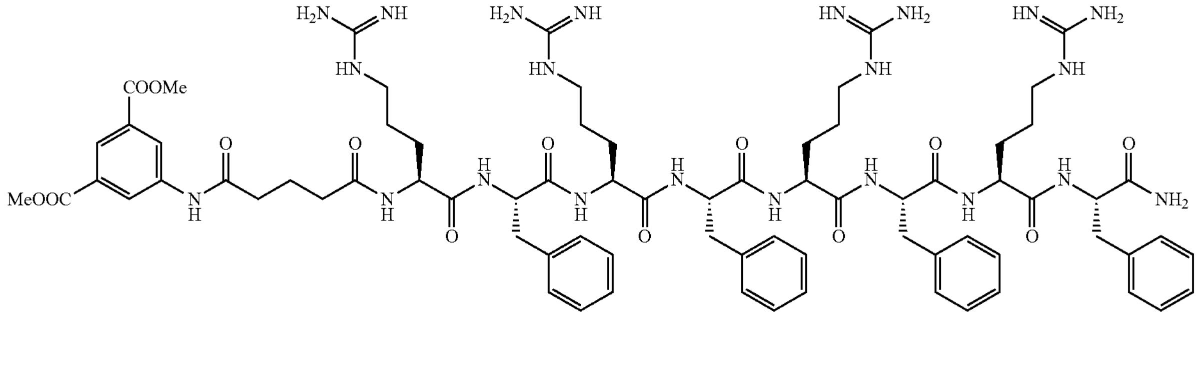 [SMILES: COC(=O)c1cc(NC(=O)CCCC(=O)N[C@@H](CCCNC(=N)N)C(=O)N[C@@H](Cc2ccccc2)C(=O)N[C@@H](CCCNC(=N)N)C(=O)N[C@@H](Cc2ccccc2)C(=O)N[C@@H](CCCNC(=N)N)C(=O)N[C@@H](Cc2ccccc2)C(=O)N[C@@H](CCCNC(=N)N)C(=O)N[C@@H](Cc2ccccc2)C(N)=O)cc(C(=O)OC)c1]

The antibacterial peptide H—(RF)4—$NH_2$ is synthesized on Rink Amide resin (load 0.52 mmol/g, synthesis scale: 0.25 mmol) by Fmoc/tBu strategy. Each coupling is followed by deprotection of the Fmoc group at N-ter. The peptide is then functionalized on a support after introduction of a glutaric spacer (or "linker") in DCM for 15 minutes using glutaric anhydride (5eq) in the presence of DIEA (7 eq). The resin is washed (3*DMF, 1 *MeOH and 1 *DCM). The amino dimethylisophthalate is coupled in DMF in the presence of 3 eq. of EDC.HCl and 1 eq. of DMAP. The reaction mixture is stirred overnight and then the resin is washed (3*DMF, 1*MeOH and 1*DCM) and cleaved in a DCM/TFA/TIS/$H_2O$ mixture 50/47.5/2.5/2.5 for 2×1 h. The "cleavage" solution is concentrated at reduced pressure, and then the antibacterial peptide is precipitated in diethyl ether and finally purified by preparative HPLC (Column Vydac Denali 10 μm C18 120 Å (310×25 mm) using a gradient from 20 to 60% of buffer B in 40 min).

ESI-MS (m/z): $[M+H]^+$ theoretical $C_{75}H_{103}N_{22}O_{14}$: 1536.78, experimental: 1536.84

HPLC (retention time, min): 3.24 b) Peptide H-$(R)_2$-Palm

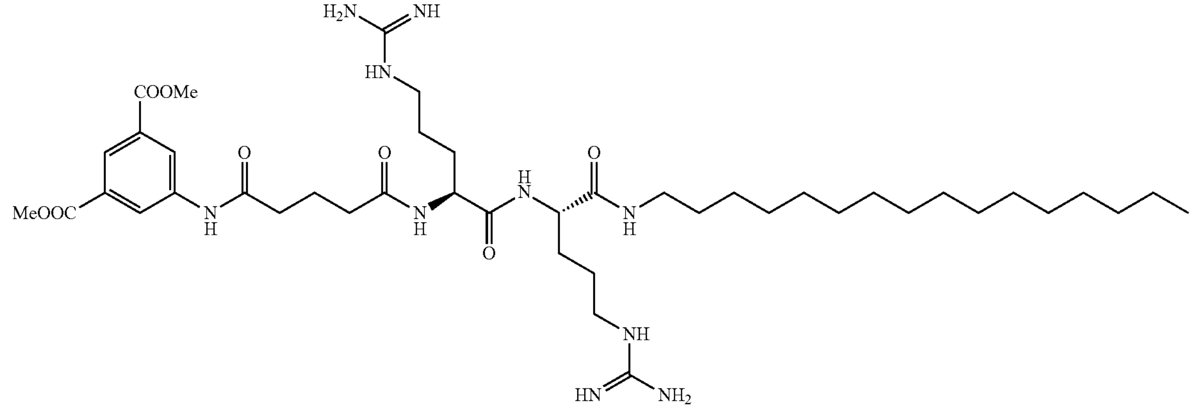 [SMILES: CCCCCCCCCCCCCCCCNC(=O)[C@H](CCCNC(=N)N)NC(=O)[C@H](CCCNC(=N)N)NC(=O)CCCC(=O)Nc1cc(C(=O)OC)cc(C(=O)OC)c1]

The antibacterial peptide H—$(R)_2$-Palm is synthesized on a Rink resin (load 0.52 mmol/g, synthesis scale: 0.25 mmol) functionalized beforehand with a benzotriazole by Fmoc/tBu strategy. Each coupling is followed by deprotection of the Fmoc group at N-ter.

Preparation of the Resin

The Rink-Amide resin is treated beforehand with piperidine (20% in the DMF) and washed (3*DMF, 1 *MeOH and 1 *DCM). 4-Amino 3-nitrobenzoic acid is coupled in DMF in the presence of 3 eq. of HATU and 6 eq. of DIEA. The reaction mixture is stirred for 2 h, then the resin is washed (3*DMF, 1 *MeOH and 1 *DCM), capped with acetic anhydride (15 ml of a solution at 10% v/v in DCM) and then washed (2*DCM, 3*DMF, 1 *MeOH and 1 *DCM). Reduction of the nitro group is carried out in a solution of 5 g of $SnCl_{12}$ ($2H_2O$) and 900 μL DBU per 10 ml of DMF, which is added to the resin while bubbling with nitrogen for 10 minutes. The reaction mixture is stirred for 15 h, syringe opened and washed (3*DMF, 3* DCM). Introduction of the peptide sequence —$(R)_2$— is performed by Fmoc/tBu strategy. Each coupling is followed by deprotection of the Fmoc group at N-ter. The peptide is then functionalized on a support after introduction of a glutaric spacer (or "linker") in DCM for 15 minutes using glutaric anhydride (5eq) in the presence of DIEA (7 eq). The resin is washed (3*DMF, 1 *MeOH and 1 *DCM). The amino dimethylisophthalate is coupled in DMF in the presence of 3 eq. of EDC.HCl and 1 eq. of DMAP. The reaction mixture is stirred overnight and then the resin is washed (3*DMF, 1*MeOH and 1*DCM).

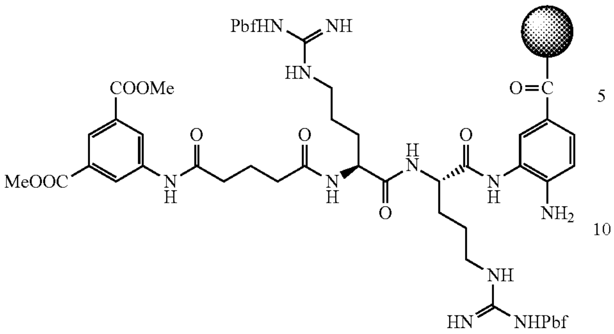

The resin is then treated with isoamyl nitrite (10 equivalents) for 90 minutes (washing DCM x5).

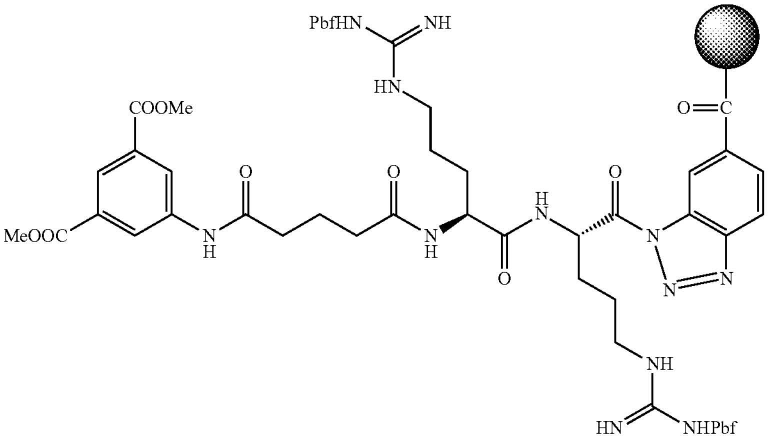

The nucleophile (4 equivalents/in this case hexadecylamine) in solution in DCM in the presence of DIEA (8 equivalents) is bubbled with nitrogen for 20 minutes before the end of cyclization, and then is introduced immediately on the resin. The reaction mixture is stirred, inducing cleavage of the peptide from the resin.

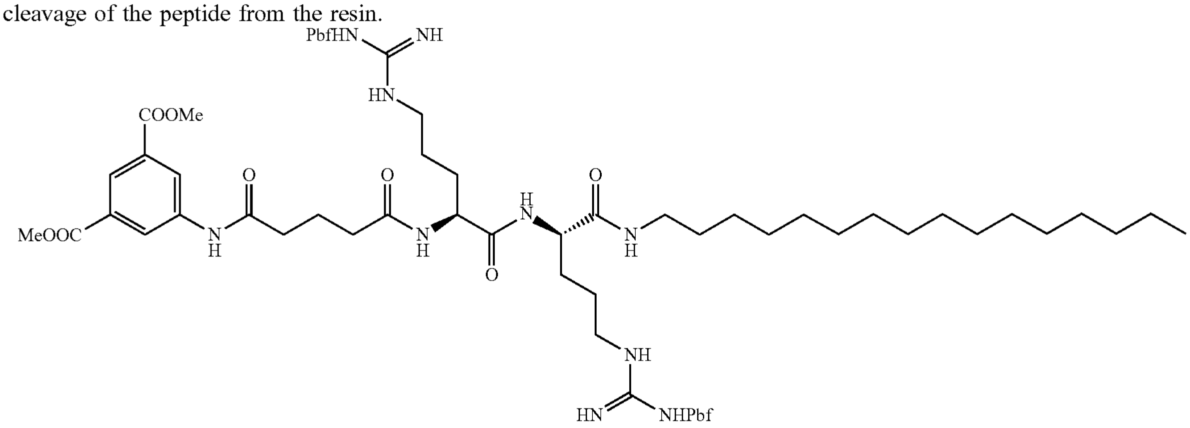

The peptide is cleaved in DCM/TFA/TIS/$H_2O$ mixture 50/47.5/2.5/2.5 for 2×1 h. The "cleavage" solution is concentrated at reduced pressure, and then the antibacterial peptide is precipitated in diethyl ether and finally purified by preparative HPLC (Column Vydac Denali 10 μm C18 120 Å (310×25 mm) using a gradient from 20 to 60% of buffer B in 40 min).

ESI-MS (m/z): $[M+H]^+$ theoretical $C_{43}H_{75}N_{10}O_8$: 860.13, experimental: 859.80.

Example 2: Preparation of Dimethyl Glutamate Monomers Substituted with a Peptide

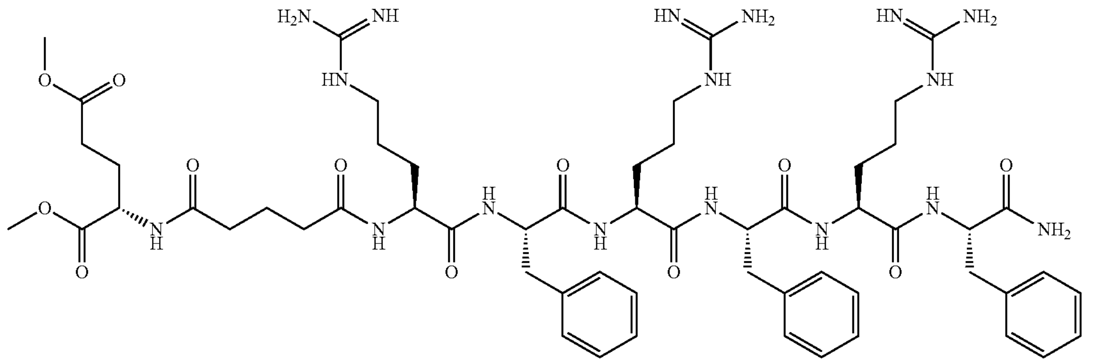 [SMILES: COC(=O)CC[C@H](NC(=O)CCCC(=O)N[C@@H](CCCNC(=N)N)C(=O)N[C@@H](Cc1ccccc1)C(=O)N[C@@H](CCCNC(=N)N)C(=O)N[C@@H](Cc1ccccc1)C(=O)N[C@@H](CCCNC(=N)N)C(=O)N[C@@H](Cc1ccccc1)C(N)=O)C(=O)OC]

The antibacterial peptide H—(RF)3-$NH_2$ is synthesized on a Rink resin (load 0.52 mmol/g, synthesis scale: 0.25 mmol) by Fmoc/tBu strategy. Each coupling is followed by deprotection of the Fmoc group at N-ter. The peptide is then functionalized on the support after introduction of a glutaric spacer in DCM for 15 minutes using glutaric anhydride (5 eq) in the presence of DIEA (7 eq). The resin is washed (3*DMF, 1 *MeOH and 1 *DCM). The dimethyl glutamate is coupled in DMF in the presence of 3 eq. of EDC.HCl and 1 eq. of DMAP. The reaction mixture is stirred overnight and then the resin is washed (3*DMF, 1 *MeOH and 1 *DCM) and cleaved in DCM/TFA/TIS/$H_2O$ mixture 50/47.5/2.5/2.5 for 2×1 h. The "cleavage" solution is concentrated at reduced pressure, and then the antibacterial peptide is precipitated in diethyl ether and finally purified by preparative HPLC (Column Vydac Denali 10 μm C18 120 Å (310×25 mm) using a gradient from 20 to 60% of buffer B in 40 min).

ESI-MS (m/z): $[M+H]^+$ theoretical $C_{57}H_{84}N_{17}O_{12}$: 1199.40, experimental: 1199.70

HPLC (retention time, min): 3.64

Example 3: Preparation of bis(2-hydroxyethyl) Isophthalate Monomers Substituted with a Peptide The antibacterial peptide H—(RF)3-$NH_2$ is synthesized on Rink Amide resin (load 0.52 mmol/g, synthesis scale: 0.25 mmol) by Fmoc/tBu strategy. Each coupling is followed by deprotection of the Fmoc group at N-ter. The peptide is then functionalized on the support after introduction of a glutaric spacer in DCM for 15 minutes using glutaric anhydride (5eq) in the presence of DIEA (7 eq). The resin is washed (3*DMF, 1 *MeOH and 1 *DCM). The 5-aminoisophthalic acid (3 eq.) is coupled in DMF after preactivation of the resin with HATU (3 eq.) in the presence of DIEA (6 eq.) for 15 minutes. The ethylene glycol (12 eq.) is coupled in DMF in the presence of 6 eq. of EDC.HCl and 1 eq. of DMAP. The reaction mixture is stirred overnight; then the resin is washed (3*DMF, 1 *MeOH and 1 *DCM) and cleaved in DCM/TFA/TIS/$H_2O$ mixture 50/47.5/2.5/2.5 for 2×1 h. The "cleavage" solution is concentrated at reduced pressure, and then the antibacterial peptide is precipitated in diethyl ether and finally purified by HPLC (Column Vydac Denali 10 μm C18 120 Å (310×25 mm) using a gradient from 20 to 60% of buffer B in 40 min).

ESI-MS (m/z): $[M+H]^+$ theoretical $C_{62}H_{86}N_{17}O_{14}$: 1293.47, experimental: 1293.70

HPLC (retention time, min): 2.71

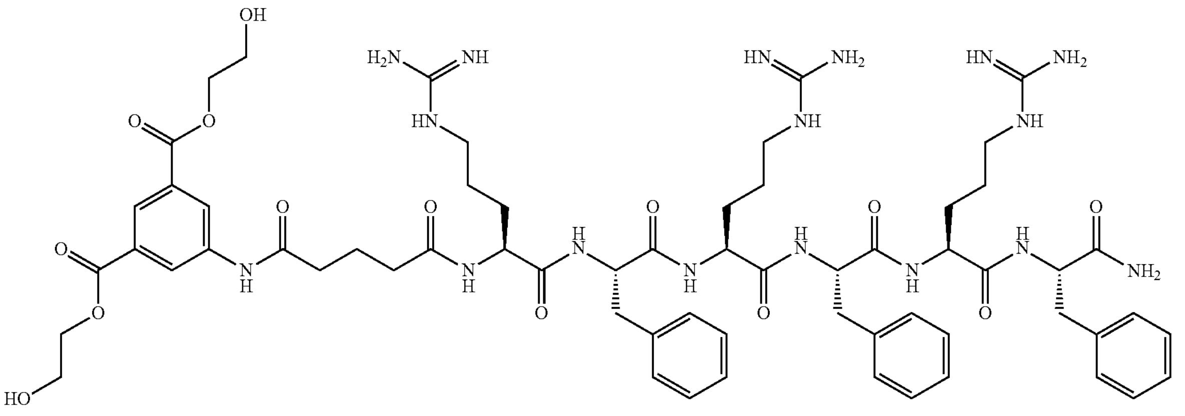 [SMILES: N=C(N)NCCC[C@H](NC(=O)CCCC(=O)Nc1cc(C(=O)OCCO)cc(C(=O)OCCO)c1)C(=O)N[C@@H](Cc1ccccc1)C(=O)N[C@@H](CCCNC(=N)N)C(=O)N[C@@H](Cc1ccccc1)C(=O)N[C@@H](CCCNC(=N)N)C(=O)N[C@@H](Cc1ccccc1)C(N)=O]

Example 4: Preparation of bis(4-hydroxybutyl) Isophthalate Monomers Substituted with a Peptide

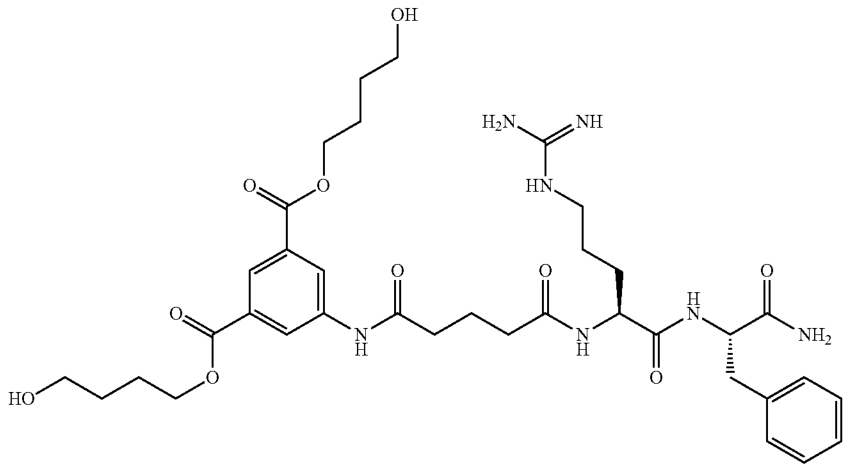 [SMILES: N=C(N)NCCC[C@H](NC(=O)CCCC(=O)Nc1cc(C(=O)OCCCCO)cc(C(=O)OCCCCO)c1)C(=O)N[C@@H](Cc1ccccc1)C(N)=O]

Method A

The antibacterial peptide H—(RF)—$NH_2$ is synthesized on Rink Amide resin (load 0.52 mmol/g, synthesis scale: 0.25 mmol) by Fmoc/tBu strategy. Each coupling is followed by deprotection of the Fmoc group at N-ter. The peptide is then functionalized on the support after introduction of a glutaric spacer in DCM for 15 minutes using glutaric anhydride (5 eq) in the presence of DIEA (7 eq). The resin is washed (3*DMF, 1 *MeOH and 1 *DCM). The 5-aminoisophthalic acid (3 eq.) is coupled in DMF after preactivation of the resin with HATU (3 eq.) in the presence of DIEA (6 eq.) for 15 minutes. The butylene glycol (12 eq.) is coupled in DMF in the presence of 6 eq. of EDC.HCl and 1 eq. of DMAP. The reaction mixture is stirred overnight. Then the resin is washed (3*DMF, 1 *MeOH and 1 *DCM) and cleaved in DCM/TFA/TIS/$H_2O$ mixture 50/47.5/2.5/2.5 for 2×1 h. The "cleavage" solution is concentrated at reduced pressure, and then the antibacterial peptide is precipitated in diethyl ether and finally purified by preparative HPLC. (Column Vydac Denali 10 μm C18 120 Å (310×25 mm) using a gradient from 20 to 60% of buffer B in 40 min).

ESI-MS (m/z): $[M+H]^+$ theoretical $C_{36}H_{52}N_7O_{10}$: 742.84, experimental: 742.54

HPLC (retention time, min): 3.29

Method B

The antibacterial peptide H—(RF)—$NH_2$ is synthesized on Rink Amide resin (load 0.52 mmol/g, synthesis scale: 0.25 mmol) by Fmoc/tBu strategy. Each coupling is followed by deprotection of the Fmoc group at N-ter. The peptide is then functionalized on a support after introduction of a glutaric spacer (or "linker") in DCM for 15 minutes using glutaric anhydride (5eq) in the presence of DIEA (7 eq). The resin is washed (3*DMF, 1 *MeOH and 1 *DCM). The amino dimethylisophthalate is coupled in DMF in the presence of 3 eq. of EDC.HCl and 1 eq. of DMAP. The reaction mixture is stirred overnight and then the resin is washed (3*DMF, 1*MeOH and 1*DCM) and cleaved in DCM/TFA/TIS/$H_2O$ mixture 50/47.5/2.5/2.5 for 2×1 h. The "cleavage" solution is concentrated at reduced pressure, and then the antibacterial peptide is precipitated in diethyl ether and finally purified by preparative HPLC. (Column Vydac Denali 10 μm C18 120 Å (310×25 mm) using a gradient from 20 to 60% of buffer B in 40 min).

Dimethyl isophthalate peptide:

ESI-MS (m/z): $[M+H]^+$ theoretical $C_{30}H_{40}N_7O_8$: 626.68, experimental: 626.32

HPLC (retention time, min): 3.38

The dimethyl isophthalate peptide is then transesterified in solution in 1,4-butanediol in the presence of catalyst for 2 h between 150 °C and 180 °C.

ESI-MS (m/z): $[M+H]^+$ theoretical $C_{36}H_{52}N_7O_{10}$: 742.84, experimental: 742.33

HPLC (retention time, min): 3.25

It was also observed that the transesterification (in the same conditions as for a diester compound, namely solution in 1,4-butanediol in the presence of catalyst for 2 h between 150 °C and 180 °C) starting from a diacid peptide compound led to degradation of the peptide.

Example 5: Preparation of Monomers of the Amino Ester Monoamide Type Substituted with a Peptide (Peptide (FR)4))

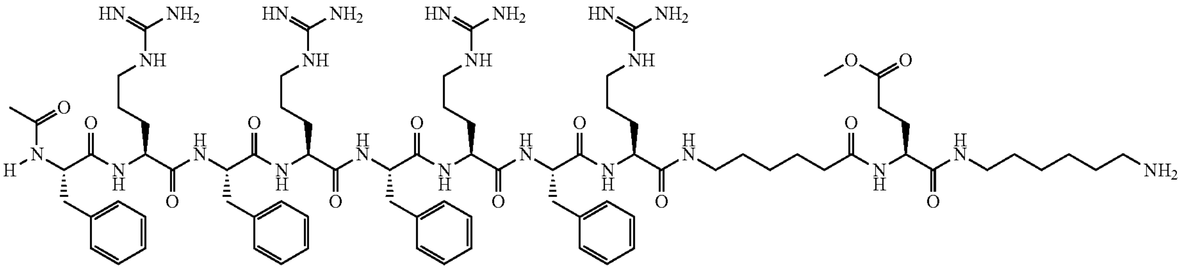

Molecular Weight: 1628,01

Figure 2:
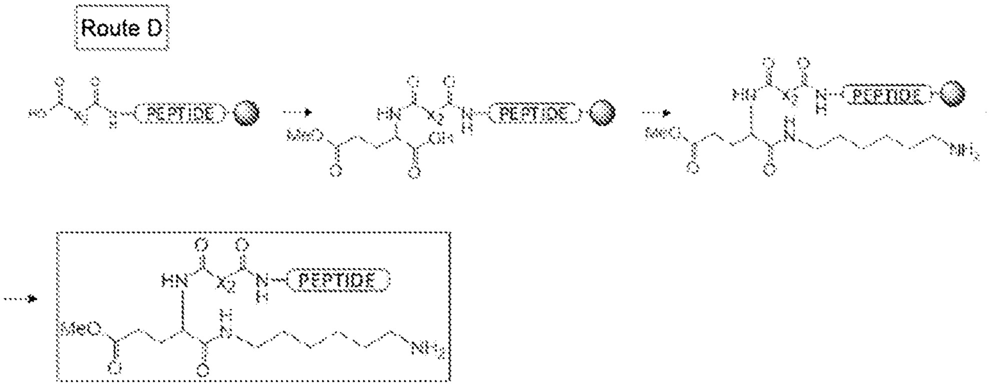
FIG. 2 shows a scheme of various syntheses of monomers of the amino ester monoamide type substituted with a peptide (X2=$(C_1-C_{12})$alkyl, aryl, or polyalkylene glycol).
Figure 2:
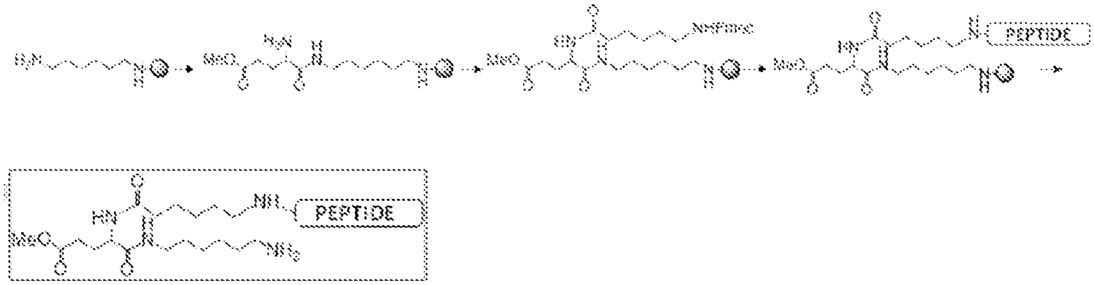
Figure 2:
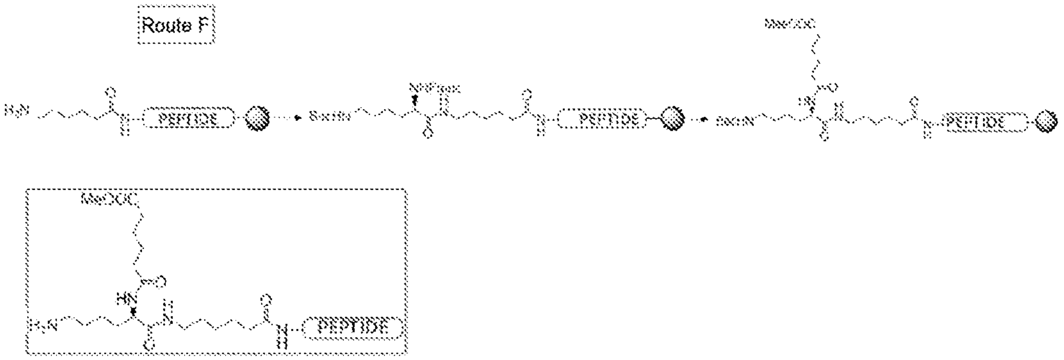
Figure 3:
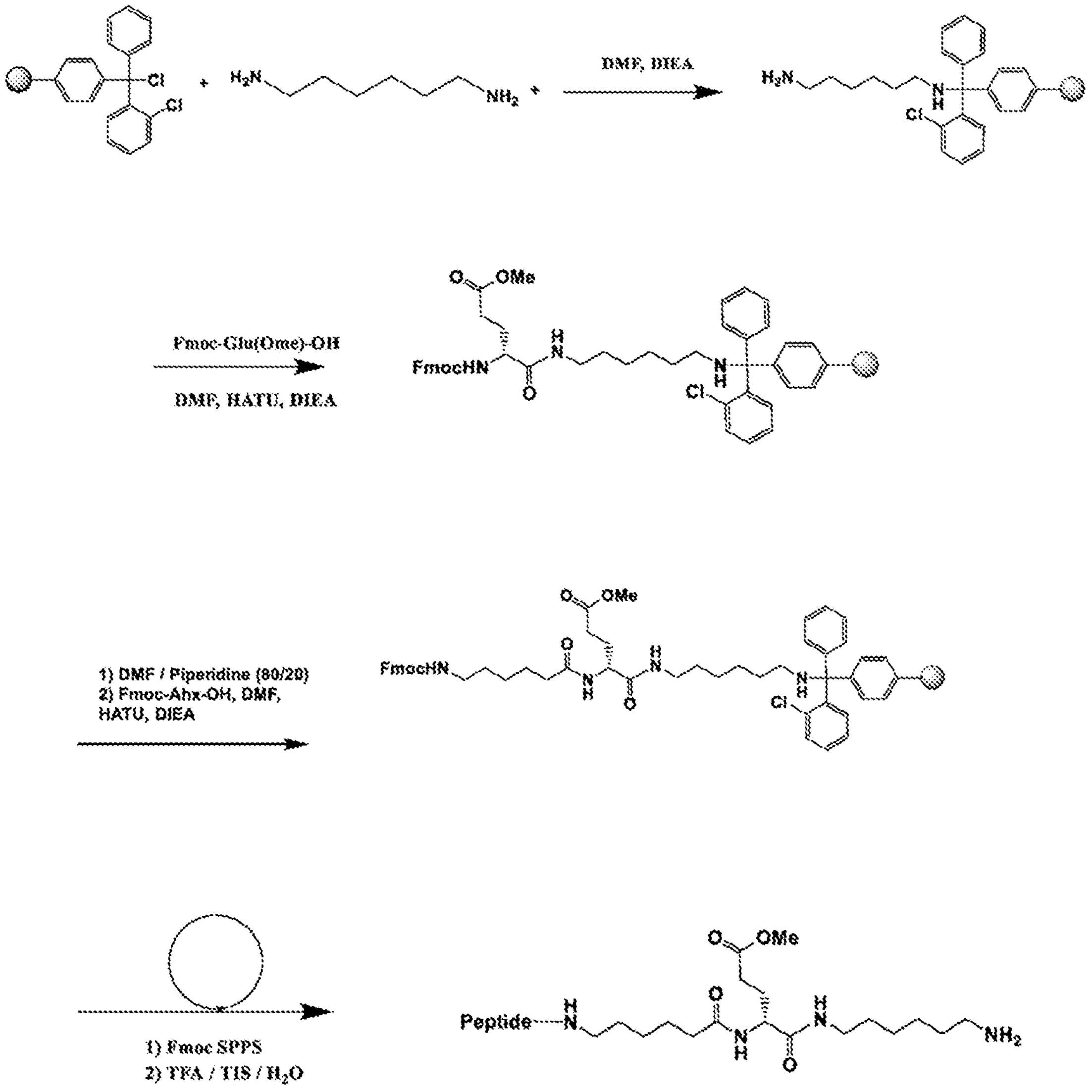
FIG. 3 shows a scheme of synthesis on 2-chlorotrityl resin, of monomers of the amino ester monoamide type substituted with a peptide.

The elementary block is synthesized on 2-chlorotrityl chloride resin (load 0.28 mmol/g, synthesis scale: 0.25 mmol) by Fmoc/tBu strategy (FIG. 2—Route E, and FIG. 3). After swelling the resin in DCM beforehand, hexamethylenediamine (5 eq.) is introduced onto the resin in DMF in the presence of DIEA (11 eq.) for 24 h. The reaction mixture is stirred overnight, and then the resin is washed (3*DMF, 1 *MeOH and 1 *DCM). After coupling of the amino acid Fmoc-Glu(Ome)-OH in the presence of 3 equivalents of HATU and 6 equivalents of DIEA, the resin is washed (3*DMF, 1 *MeOH and 1 *DCM). The spacer Fmoc-Ahx-OH is introduced in DMF in the presence of 3 equivalents of HATU and 6 equivalents of DIEA, and the resin is washed (3*DMF, 1 *MeOH and 1 *DCM). Synthesis of the peptide is then carried out conventionally using a peptide synthesizer of the Symphony X type (Protein Technologies, Inc., USA) by Fmoc/tert-butyl strategy using nitrogen bubbling as the method of agitation for the cycles of coupling and deprotection of the Fmoc groups in N-terminal position. Cleavage of the peptide from the resin is carried out by 2 methods:

Method A (The Peptide is Cleaved and Deprotected)

The resin is cleaved in DCM/TFA/TIS/$H_2O$ mixture 50/47.5/2.5/2.5 for 2×1 h. The "cleavage" solution is concentrated at reduced pressure, and then the antibacterial peptide is precipitated in diethyl ether and finally purified by preparative HPLC (Column Vydac Denali 10 µm C18 120 Å (310×25 mm) using a gradient from 20 to 60% of buffer B in 40 min).

ESI-MS (m/z): $[M+H]^+$ theoretical $C_{80}H_{123}N_{24}O_{13}$: 1629.01, experimental: 1629.37

HPLC (retention time, min): 2.63

Method B (The Peptide is Cleaved in its Protected Form)

The resin is cleaved in AcOH/TFE/DCM mixture (10/20/70) for 2×1 h. The "cleavage" solution is concentrated at reduced pressure, and then the antibacterial peptide is precipitated in diethyl ether and finally purified by HPLC preparative (Column Vydac Denali 10 µm C18 120 Å (310×25 mm) using a gradient from 20 to 60% of buffer B in 40 min).

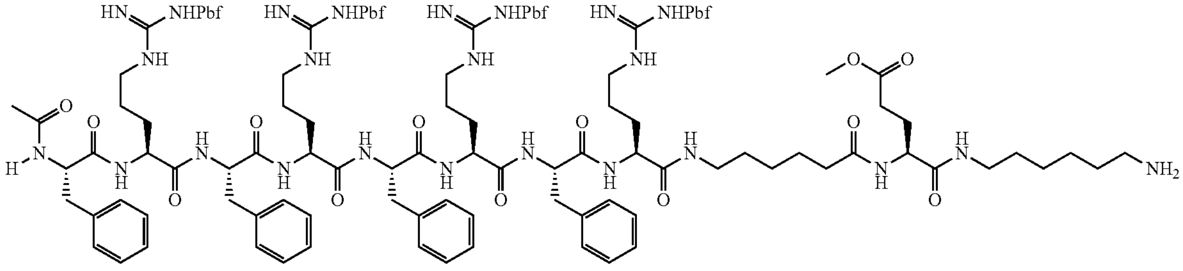

ESI-MS (m/z): $[M+H]^+$ theoretical $C_{132}H_{187}N_{24}O_{25}S_4$: 2638.32, experimental: 2638.28

HPLC (retention time, min): 5.97

B. Preparation of the Polymers

Example 6: Preparation of the Copolymers of poly(butylene adipate-co-terephthalate) (PBAT)

Synthesis of the copolymers of poly(butylene adipate-co-terephthalate) is carried out by polycondensation in two steps in the presence of catalyst ($Ti(OBu)^4$).

The first step is a transesterification between the diesters and 1,4-butanediol in excess to obtain oligomers, and the second step is polycondensation of these oligomers to remove the excess 1,4-butanediol to form polyesters with higher molecular weight (Mw) (scheme 1).

Scheme 1

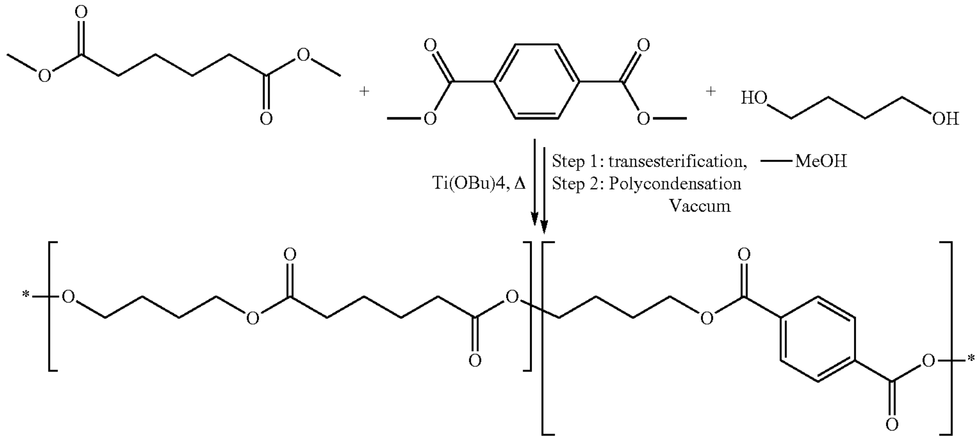

In the first step, which consists of a transesterification, the following elements, dimethyl adipate (DMA, 12.66 g (0.5 eq.)) and dimethyl terephthalate (DMT, 14.11 g (0.5 eq.)) in stoichiometric amount (total diester functions representing 1 equivalent (DMA+DMT=1 eq.)) are added to 1,4-butanediol in slight excess (15.07 g, 1.15 eq.) and to the catalyst (0.1%) in a 250 ml three-necked flask equipped with a watertight mechanical stirrer, a nitrogen inlet and a distilling head connected to a graduated tube for collecting the methanol distilled.

The reactor is purged with argon in 3 successive cycles and the transesterification step is carried out under argon atmosphere at 160 °C for 1 h until the reaction byproduct methanol is removed. Polycondensation is carried out by placing the system under vacuum (20 mbar) for 5 h between 160 °C and 180 °C.

After cooling, the reaction mixture is dissolved in dichloromethane and precipitated in methanol, filtered and dried.

Example 7: Preparation of the Copolymers of poly(butylene succinate-co-terephthalate)

Synthesis of the copolymers of poly(butylene succinate-co-terephthalate) with x% of aromatic units is carried out by polycondensation in two steps in the presence of catalyst (Ti(OBu)+). The first step is a transesterification between the diesters and 1,4-butanediol in excess to obtain oligomers, and the second step is polycondensation of these oligomers to remove the excess 1,4-butanediol to form polyesters with higher molecular weight (Mw) (Scheme 2).

Scheme 2

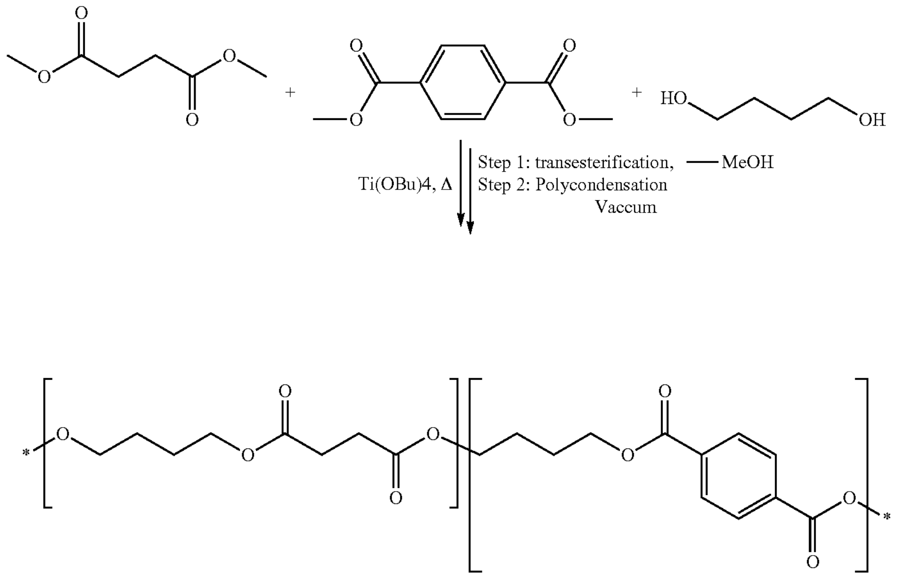

In the first step, which consists of a transesterification, the following elements, dimethyl succinate (DMS 15.94 g 0.75 eq.) and dimethyl terephthalate (DMT 7.06 g 0.25 eq.) in second step is polycondensation of these oligomers to remove the excess 1,4-butanediol to form polyesters with higher molecular weight (Mw) (Scheme 3).

Scheme 3

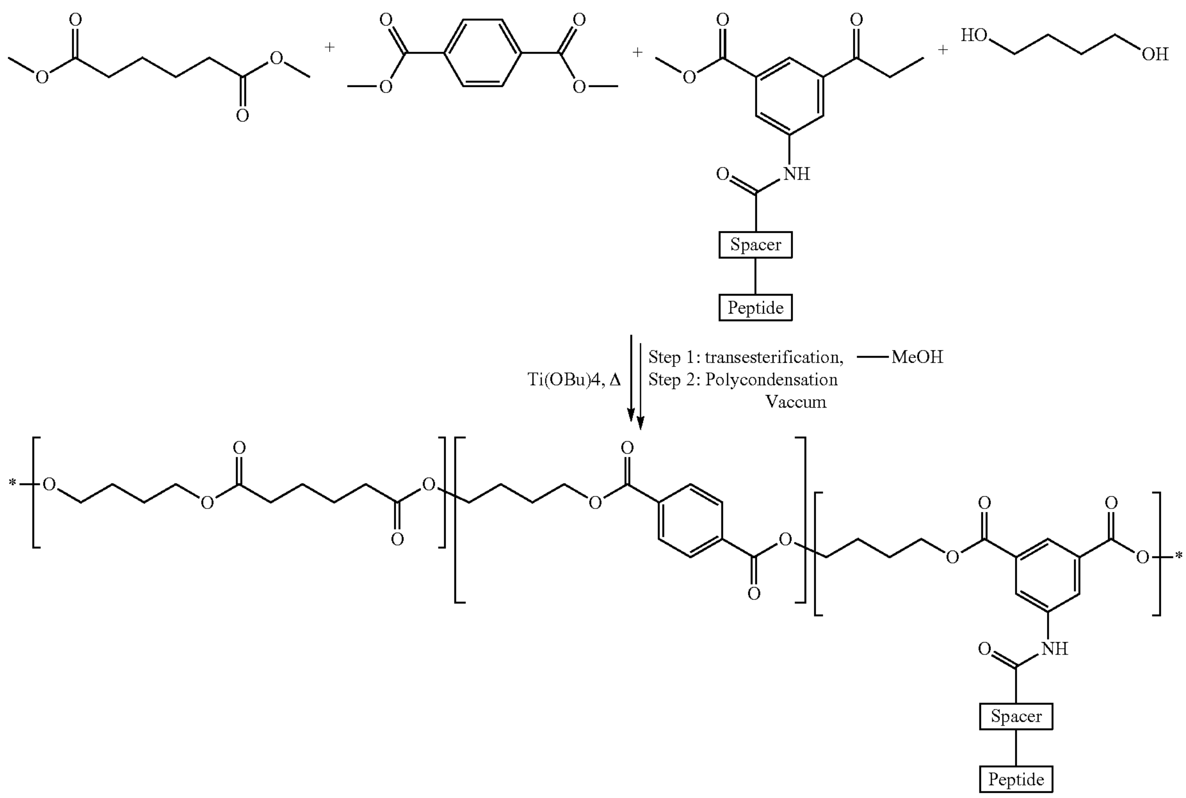

stoichiometric amount (total diester functions representing 1 equivalent (DMS+DMT=1 eq.)) are added to 1,4-butanediol in slight excess (BD 15.07 g 1.15 eq.) and to the catalyst (0.1%) in a 250 ml three-necked flask equipped with a watertight mechanical stirrer, a nitrogen inlet and a distilling head connected to a graduated tube for collecting the methanol distilled.

The reactor is purged with argon in 3 successive cycles and the transesterification step is carried out under argon atmosphere at 160 °C for 1 h until the reaction byproduct methanol is removed. Polycondensation is carried out by placing the system under vacuum (20 mbar) for 5 h between 160 °C and 180 °C.

After cooling, the reaction mixture is dissolved in dichloromethane and precipitated in methanol, filtered and dried.

Example 8: Preparation of the Copolymers of poly(butylene adipate-co-terephthalate-co-isophthalatopeptide) (PBAT-co-peptide)

Synthesis of the copolymers of poly(butylene adipate-co-terephthalate-co-isophthalatopeptide) with 50 mol % of aromatic units and with 0.5 wt % of peptide units is carried out by polycondensation in two steps in the presence of catalyst ($Ti(OBu)_4$).

The first step is a transesterification between the diesters and 1,4-butanediol in excess to obtain oligomers, and the second step is polycondensation of these oligomers to remove the excess 1,4-butanediol to form polyesters with higher molecular weight (Mw).

In the first step, which consists of a transesterification, the following elements, dimethyl adipate (DMA, 12.16 g 0.5 eq.), dimethyl terephthalate (DMT 14.11 g 0.5 eq) and isophthalatopeptide (DMIP peptide=monomer from Example 1a, 255 mg 0.5 wt %) in stoichiometric amount (total diester functions representing 1 equivalent (DMA+DMT+DMIPpeptide=1 eq.)) are added to 1,4-butanediol in slight excess (BD 15.07 g 1.15 eq.) and to the catalyst (0.1%) in a 250 ml three-necked flask equipped with a watertight mechanical stirrer, a nitrogen inlet and a distilling head connected to a graduated tube for collecting the methanol distilled.

The reactor is purged with argon in 3 successive cycles and the transesterification step is carried out under argon atmosphere at 160 °C for 1 h until the reaction byproduct methanol is removed.

Polycondensation is carried out by placing the system under vacuum (20 mbar) for 5 h between 160 °C and 180 °C.

After cooling, the reaction mixture is dissolved in dichloromethane and precipitated in methanol, filtered and dried.

Example 9: Preparation of the Copolymers of poly(butylene succinate-co-terephthalate-co-isophthalatopeptide)

Synthesis of the copolymers of poly(butylene succinate-co-terephthalate-co-isophthalatopeptide) with 50 mol % of aromatic units and with 0.5 wt % of peptide units is carried out by polycondensation in two steps in the presence of catalyst ($Ti(OBu)_4$).

The first step is a transesterification between the diesters and 1,4-butanediol in excess to obtain oligomers, and the second step is polycondensation of these oligomers to remove the excess 1,4-butanediol to form polyesters of high molecular weight (Mw) (Scheme 4).

Scheme 4

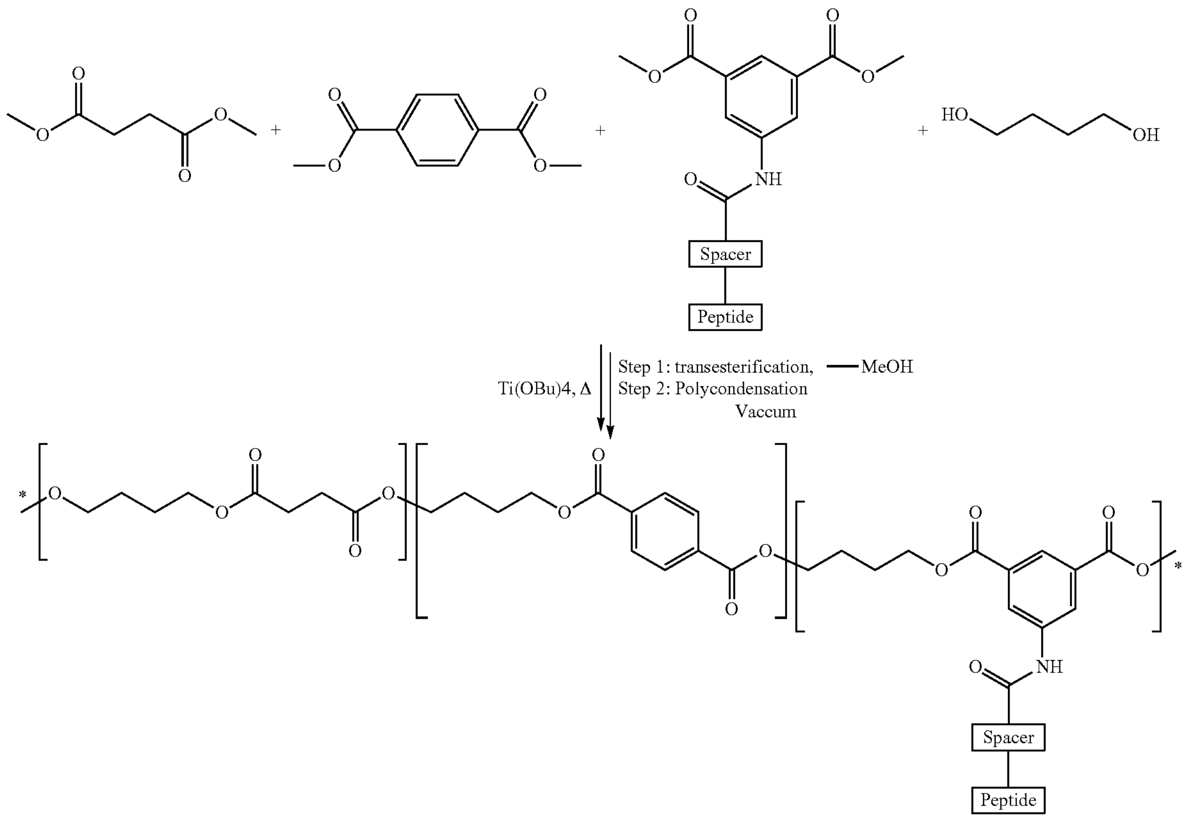

In the first step, which consists of a transesterification, the following elements, dimethyl succinate (DMS 15.94 g 0.75 eq.), dimethyl terephthalate (DMT 7.06 g 0.25 eq.) and isophthalatopeptide (DMIP peptide=monomer from Example 1a, 235 mg 0.5 wt %) in stoichiometric amount (total diester functions representing 1 equivalent (DMS+DMT+DMIPpeptide=1 eq.)) are added to 1,4-butanediol in slight excess (BD 15.07 g 1.15 eq.) and to the catalyst (0.1%) in a 250 ml three-necked flask equipped with a watertight mechanical stirrer, a nitrogen inlet and a distilling head connected to a graduated tube for collecting the methanol distilled.

The reactor is purged with argon in 3 successive cycles and the transesterification step is carried out under argon atmosphere at 160 °C for 1 h until the reaction byproduct methanol is removed. Polycondensation is carried out by placing the system under vacuum (20 mbar) for 5 h between 160 °C and 180 °C.

After cooling, the reaction mixture is dissolved in dichloromethane and precipitated in methanol, filtered and dried.

Example 10: Preparation of the Polymers of poly(butylene adipate)

Synthesis of the polymers of poly(butylene adipate) is carried out by polycondensation in two steps in the presence of catalyst (Ti(OBu)+).

The first step is a transesterification between the diester and 1,4-butanediol in excess to obtain oligomers, and the second step is polycondensation of these oligomers to remove the excess 1,4-butanediol to form polyesters with higher molecular weight (Mw) (Scheme 5).

Scheme 5

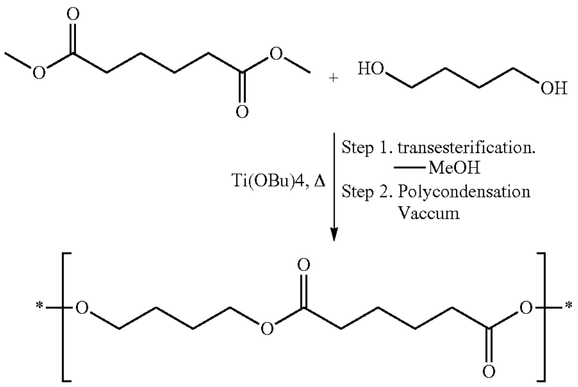

In the first step, which consists of a transesterification, the following element, dimethyl adipate (DMA 25.33 g 1 eq.), is added to 1,4-butanediol in slight excess (BD 15.07 g 1.15 eq.) and to the catalyst (0.1%) in a 250 ml three-necked flask equipped with a watertight mechanical stirrer, a nitrogen inlet and a distilling head connected to a graduated tube for collecting the methanol distilled.

The reactor is purged with argon in 3 successive cycles and the transesterification step is carried out under argon atmosphere at 160 °C for 1 h until the reaction byproduct methanol is removed. Polycondensation is carried out by placing the system under vacuum (20 mbar) for 5 h between 160 °C and 180 °C.

After cooling, the reaction mixture is dissolved in dichloromethane and precipitated in methanol, filtered and dried.

Example 11: Preparation of the Polymers of poly(butylene succinate) (PBS)

Synthesis of the polymers of poly(butylene succinate) is carried out by polycondensation in two steps in the presence of catalyst (Ti(OBu)$^4$).

The first step is a transesterification between the diester and 1,4-butanediol in excess to obtain oligomers, and the second step is polycondensation of these oligomers to remove the excess 1,4-butanediol to form polyesters of high molecular weight (Mw) (Scheme 6).

Scheme 6

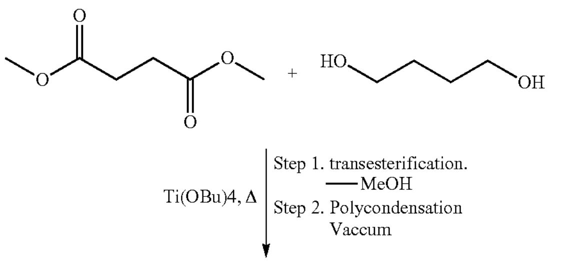

-continued

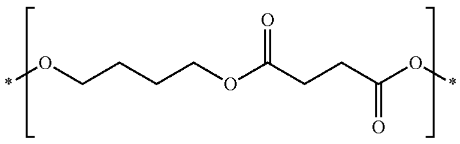

In the first step, which consists of a transesterification, the following element, dimethyl succinate (DMS 21.25 g 1 eq), is added to 1,4-butanediol in slight excess (BD 15.07 g 1.15 eq) and to the catalyst (0.1%) in a 250 ml three-necked flask equipped with a watertight mechanical stirrer, a nitrogen inlet and a distilling head connected to a graduated tube for collecting the methanol distilled.

The reactor is purged with argon in 3 successive cycles and the transesterification step is carried out under argon atmosphere at 160 °C for 1 h until the reaction byproduct methanol is removed. Polycondensation is carried out by placing the system under vacuum (20 mbar) for 5 h between 160 °C and 180 °C.

After cooling, the reaction mixture is dissolved in dichloromethane and precipitated in methanol, filtered and dried.

Example 12: Preparation of the Copolymers of poly(butylene adipate-co-isophthalatopeptide) (PBA-co-peptide)

Synthesis of the copolymers of poly(butylene adipate-co-isophthalatopeptide) with 0.5 wt % of peptide units is carried out by polycondensation in two steps in the presence of catalyst ($Ti(OBu)_4$).

The first step is a transesterification between the diesters and 1,4-butanediol in excess to obtain oligomers, and the second step is polycondensation of these oligomers to remove the excess 1,4-butanediol to form polyesters with higher molecular weight (Mw) (Scheme 7).

Scheme 7

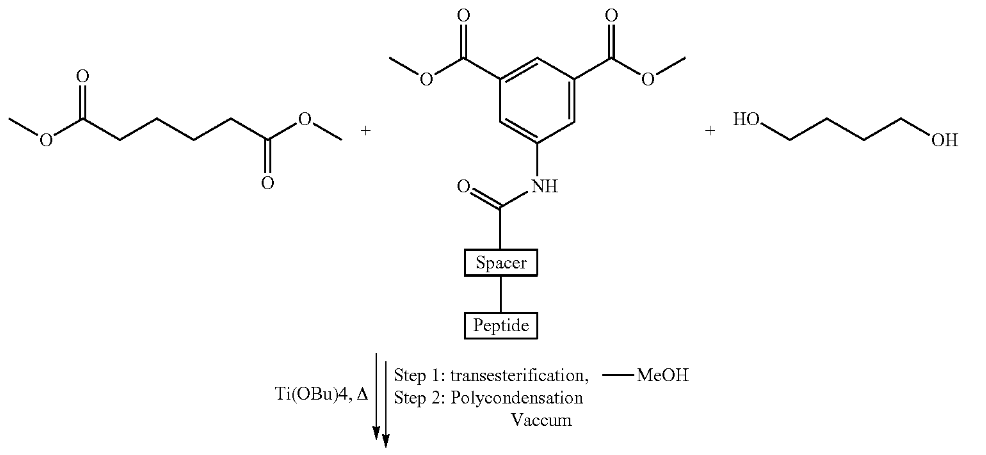

-continued

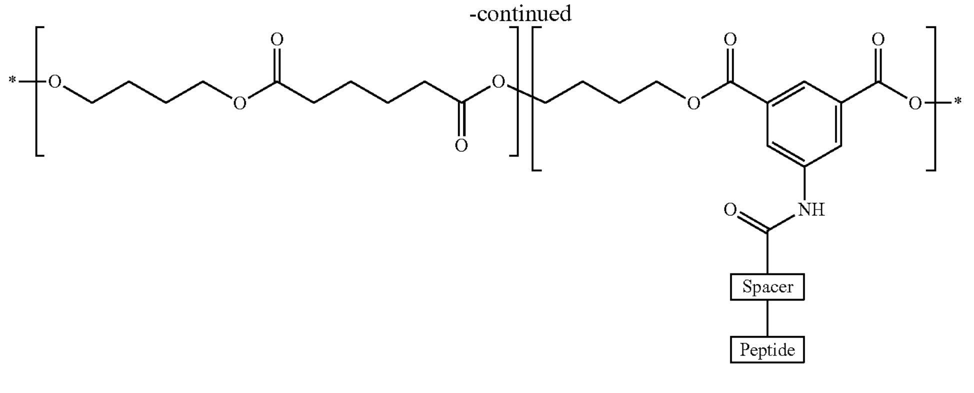

In the first step, which consists of a transesterification, the following elements, dimethyl adipate (DMA, 25.33 g 1 eq.) and isophthalatopeptide (DMIP peptide=monomer from Example 1a, 249 mg 0.5 wt %) in stoichiometric amount (total diester functions representing 1 equivalent (DMA+DMIPpeptide=1 eq.)) are added to 1,4-butanediol in slight excess (BD 15.07 g 1.15 eq.) and to the catalyst (0.1%) in a 250 ml three-necked flask equipped with a watertight mechanical stirrer, a nitrogen inlet and a distilling head connected to a graduated tube for collecting the methanol distilled.

The reactor is purged with argon in 3 successive cycles and the transesterification step is carried out under argon atmosphere at 160 °C for 1 h until the reaction byproduct methanol is removed. Polycondensation is carried out by placing the system under vacuum (20 mbar) for 5 h between 160 °C and 180 °C.

After cooling, the reaction mixture is dissolved in dichloromethane and precipitated in methanol, filtered and dried.

Example 13: Preparation of the Copolymers of poly(butylene succinate-co-terephthalate-co-isophthalatopeptide)

Synthesis of the copolymers of poly(butylene succinate-co-terephthalate-co-isophthalatopeptide) is carried out by polycondensation in two steps in the presence of catalyst ($Ti(OBu)^4$).

The first step is a transesterification between the diesters and 1,4-butanediol in excess to obtain oligomers, and the second step is polycondensation of these oligomers to remove the excess 1,4-butanediol to form polyesters of high molecular weight (Mw) (Scheme 8).

Scheme 8

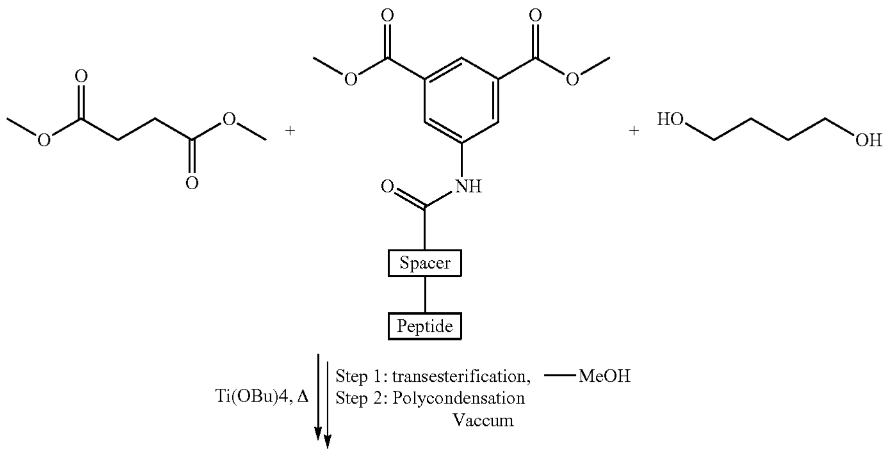

-continued

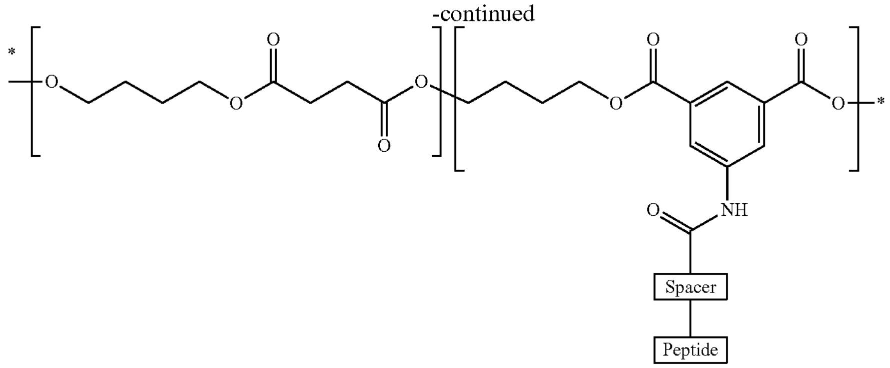

In the first step, which consists of a transesterification, the following elements, dimethyl succinate (DMS, 21.25 g 1 eq.) and isophthalatopeptide (DMIP peptide=monomer from Example 1a, 223 mg 0.5 wt %) in stoichiometric amount (total diester functions representing 1 equivalent (DMS +DMIPpeptide=1 eq.)) are added to 1,4-butanediol in slight excess (BD 15.07 g 1.15 eq.) and to the catalyst (0.1%) in a 250 ml three-necked flask equipped with a watertight mechanical stirrer, a nitrogen inlet and a distilling head connected to a graduated tube for collecting the methanol distilled.

The reactor is purged with argon in 3 successive cycles and the transesterification step is carried out under argon atmosphere at 160 °C for 1 h until the reaction byproduct methanol is removed. Polycondensation is carried out by placing the system under vacuum (20 mbar) for 5 h between 160 °C and 180 °C.

After cooling, the reaction mixture is dissolved in dichloromethane and precipitated in methanol, filtered and dried.

Example 14: Preparation of Polyurethane Polymers

Polyurethane is produced here by polyaddition, by reacting diisocyanates with diols.

A reactor is charged, under argon atmosphere, with 4,4'-diisocyanate diphenylmethylene (4.4 MDI 10 g 1.05 eq.) and the catalyst dibutyltin dilaurate (DBTL 126 mg 0.05%) in 50 ml of anhydrous dimethylacetamide at 0 °C. Bis(4-hydroxybutyl) terephthalate (278 mg) (optional) and 1,4-butanediol (1.71 g 0.5 eq.) in solution in 10 ml of anhydrous DMAc are added dropwise and the reaction mixture is stirred at room temperature for 30 minutes. Polyytetrahydrofuran 1000 (19 g, 0.5 eq.) is then added dropwise and the reaction mixture is stirred at 50 °C for 2 hours. 2 ml of ethanol is added to the reaction mixture and the solution is stirred for an additional 1 h. After cooling, the reaction mixture is precipitated in diethyl ether, filtered and dried.

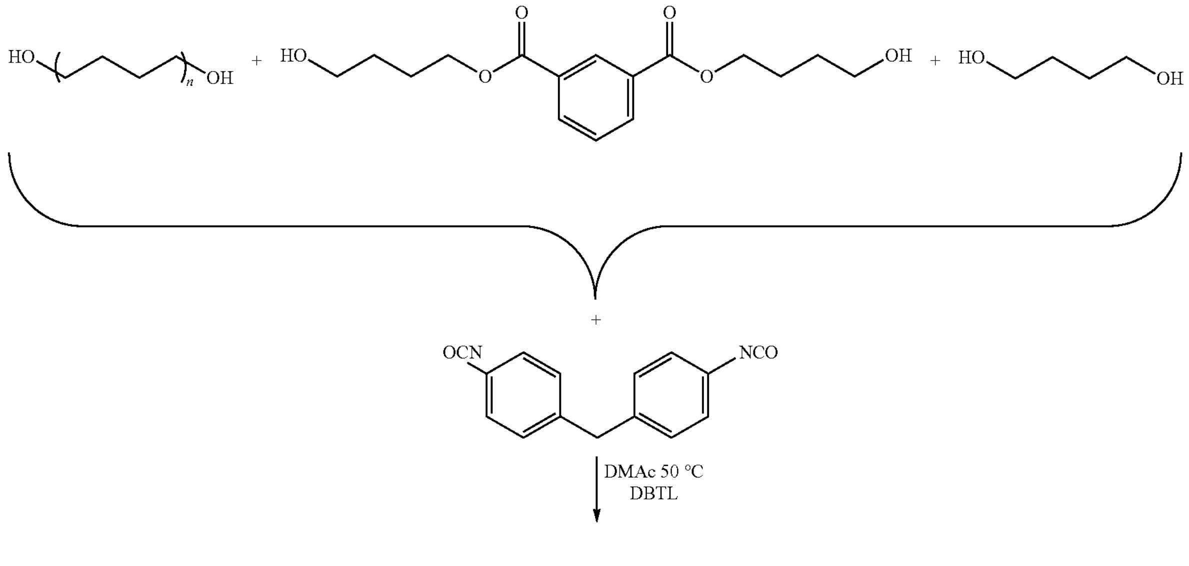

-continued

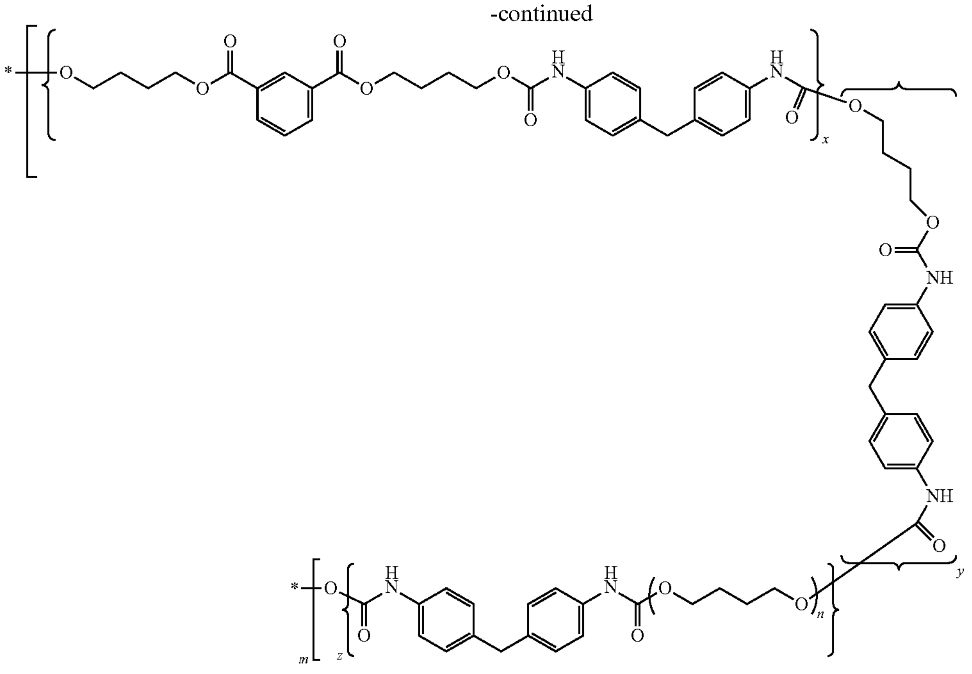

Example 15: Preparation of Peptide Polyurethane Polymers

Polyurethane is produced by polyaddition by reacting diisocyanates with diols. A reactor is charged, under argon atmosphere, with 4,4'-diisocyanate diphenylmethylene (4.4 MDI 10 g 1.05 eq) and the catalyst dibutyltin dilaurate (DBTL 126 mg 0.05%) in 50 ml of anhydrous dimethylacetamide at 0 °C. Bis(4-hydroxybutyl) isophthalato-peptide (example 4) (767 mg 0.5 wt %) and 1,4-butanediol in solution in 10 ml of anhydrous DMAc are added dropwise and the reaction mixture is stirred at room temperature for 30 minutes. Polyytetrahydrofuran 1000 is then added dropwise and the reaction mixture is stirred at 50 °C for 2 hours. 2 ml of ethanol is added to the reaction mixture and the solution is stirred for an additional 1 h. After cooling, the reaction mixture is precipitated in diethyl ether, filtered and dried.

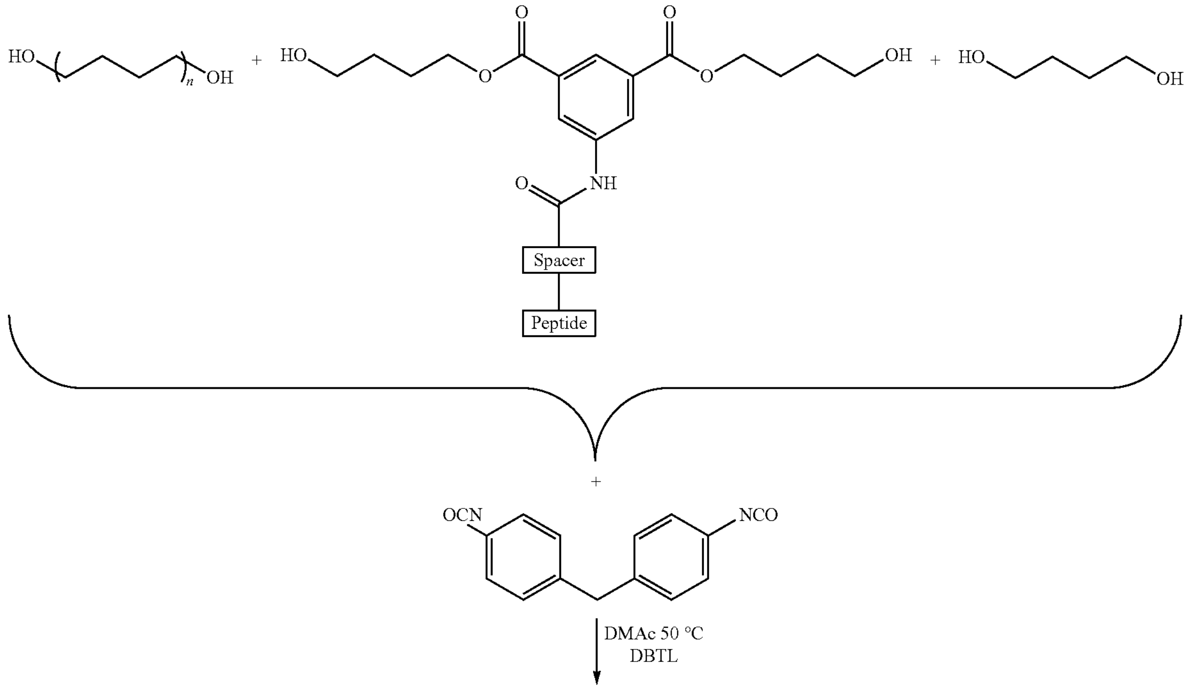

-continued

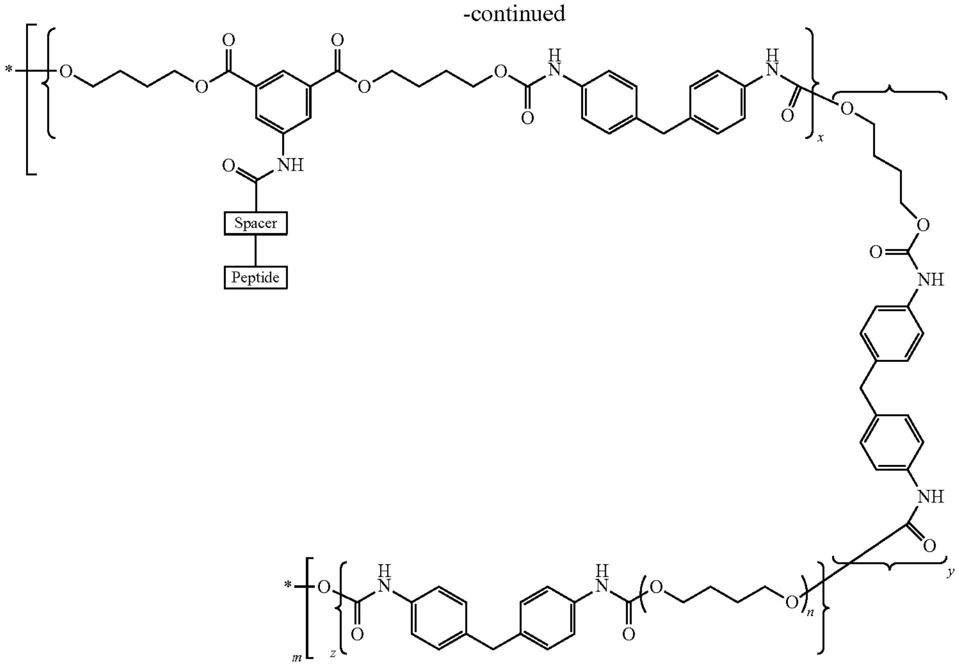

Example 16: Use of a Polymer According to the Invention in Antimicrobial Applications Forming Disks and Dumbbells Disks and dumbbells were formed by means of a Zamak Mercator micropress (IM15). The materials are introduced manually into a temperature-controlled barrel. A piston is then introduced into this barrel and then placed in the axis of the pneumatic piston. A heating time is applied as a function of the characteristics of each material. Then the material is injected through a conical mold to form the desired test specimens. Once cooled, the mold is then withdrawn and the test specimens are removed from the mold.

PBS: After stoving at 60 °C, pellets were injected at 110-115 °C with a mold temperature of 60 °C, a pressure of 6 bar and heating and cooling times of 50 s and 10 s respectively.

PBAT: After stoving at 60 °C, pellets of PBAT were injected at 100 °C or 80 °C with a mold temperature of 20 °C, a pressure of 4 bar and heating and cooling times of 60 s and 10 s respectively.

Antibacterial tests according to standard ISO 22196: 2011

The antibacterial activity according to standard ISO 22196: 2011 is intended to evaluate the antimicrobial activity of plastic products or of nonporous surfaces treated with antimicrobial agents. The method used in this study focuses solely on the evaluation of antibacterial activity. This study is intended to evaluate the antibacterial activity of the antibacterial material PBAT-co-peptide with respect to its reference without treatment according to the recommendations of standard ISO 22196: 2011 for a contact time of 24 hours:

Material PE (disk with diameter of 2.2 cm)

Figure 4:
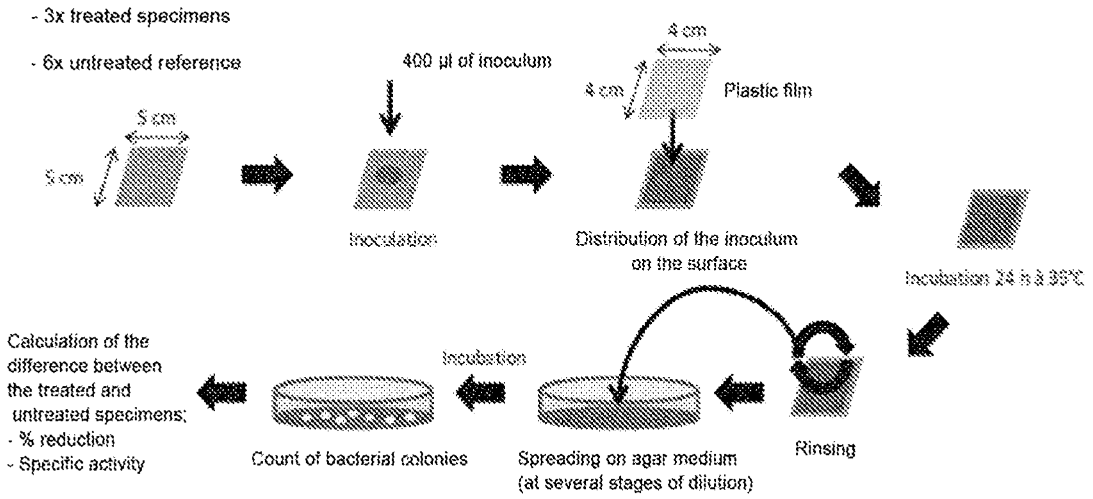
FIG. 4 shows a scheme illustrating the various steps of an antibacterial test (standard ISO 22196: 2011) on a 5 cm×5 cm specimen.

This study ideally uses samples of 5 cm×5 cm on which a known concentration of the test microorganism is deposited. After incubation for 24 hours at 35 °C, the quantity of viable microorganisms is evaluated by the technique of counting on agar medium. By comparing the bacterial concentrations obtained between the treated material and the untreated material, it is possible to determine the antibacterial activity of the formulation tested. FIG. 4 shows schematically the principle of the different steps of the analysis on a 5 cm×5 cm specimen.

The study conducted here was carried out on specimens in the form of disks with a diameter of 2.2 cm; the tests were performed with respect to bacterial strains stipulated by the standard, and very often involved in infections, Escherichia coli ATCC 8739 and *Staphylococcus aureus* ATCC 6538P.

Figure 5:
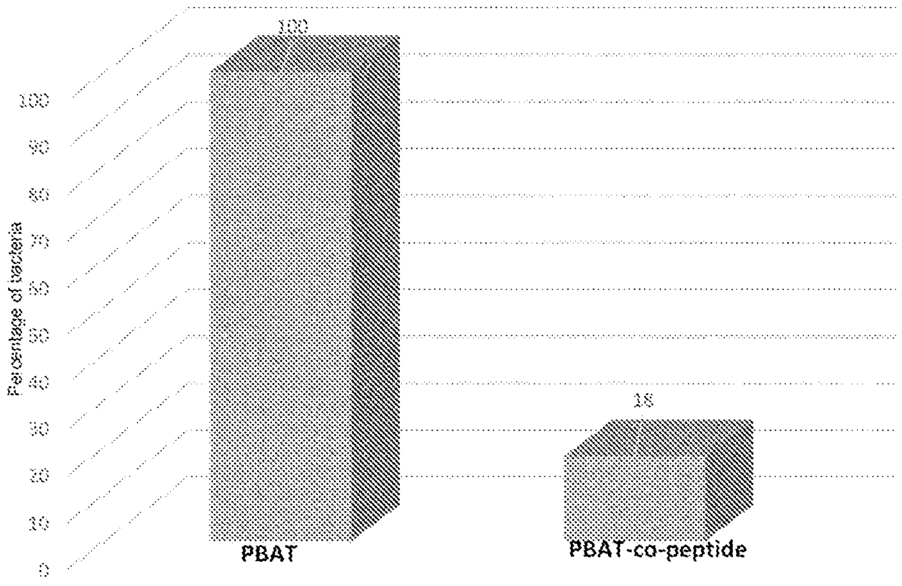
FIG. 5 shows the percentage of bacteria measured by the antibacterial test (standard ISO 22196: 2011) with poly(butylene adipate-co-terephthalate) (PBAT) and poly(butylene adipate-co-terephthalate-co-isophthalatopeptide) (PBAT-co-peptide).

The results showed significant inhibition with an 81% reduction of the growth of *Staphylococcus aureus* (Table 1 and FIG. 5).

TABLE 1

| Bacterial strain | PBAT | PBAT-co-peptide |
|---|---|---|
| *Staphylococcus aureus* | $2.73 \times 10^5$ | $5.06 \times 10^4$ |

The invention claimed is:

1. A polymer compound comprising:

repeat units of formula (I):

(I)

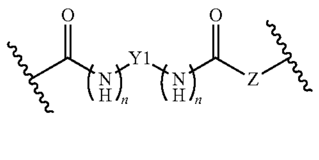

, in which n has a value of 0 or 1;

Y1 represents a radical selected from a ($C_1$-$C_{12}$)alkyl, an aryl, and an aryl-($C_1$-$C_{12}$)alkaryl; and Z represents a radical selected from:

a group represented by the following formula (Ia):

(Ia)

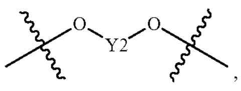

in which Y2 represents a ($C_1$-$C_{12}$)alkyl, aryl, or polyalkylene glycol; and a group represented by the following formula (Ib):

(Ib)

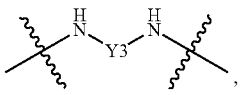

in which Y3 represents a ($C_1$-$C_{12}$)alkyl, aryl, or polyalkylene glycol;

and in which at least one of Y1, Y2, and Y3 is joined to a peptide residue via a functional residue, the functional residue and the peptide residue optionally being separated by a spacer fragment;

and repeat units of formula (II):

(II)

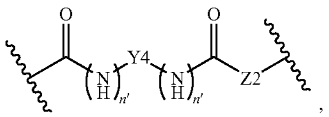

in which n' has a value of 0 or 1;

Y4 represents a radical selected from a ($C_1$-$C_{12}$)alkyl, an aryl, and an aryl-($C_1$-$C_{12}$)alkaryl; and Z2 represents a radical selected from:

a group represented by the following formula (IIa):

(IIa)

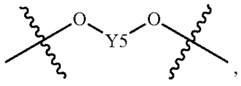

in which Y5 represents a ($C_1$-$C_{12}$)alkyl, aryl, or polyalkylene glycol; and a group represented by the following formula (IIb):

(IIb)

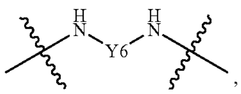

in which Y6 represents a ($C_1$-$C_{12}$)alkyl, aryl or polyalkylene glycol, provided that when n and n' have a value of 0 and Y3 is joined to a peptide residue via a functional residue, the polymer has at least one end of formula (E10) or (E40):

(E10)

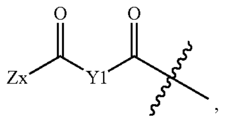

(E40)

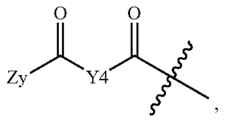

in which Zx and Zy represent independently a ($C_1$-$C_{12}$)alkyl-O— or aryl-O—.

2. The polymer compound as claimed in claim 1, in which:

n=0;

Z is a group represented by the following formula (Ia):

(Ia)

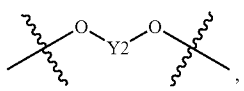

in which Y2 represents a ($C_1$-$C_{12}$)alkyl, aryl, or polyalkylene glycol; and n'=0;

Z2 is a group represented by the following formula (IIa):

(IIa)

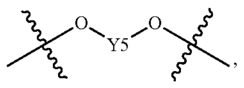

in which Y5 represents a ($C_1$-$C_{12}$)alkyl, aryl, or polyalkylene glycol;

and in which at least one of Y1 and Y2 is joined to a peptide residue via a functional residue, the functional residue and the peptide residue optionally being separated by a spacer fragment.

3. The polymer compound as claimed in claim 1, in which:

n=0;

Z is a group represented by the following formula (Ib):

(Ib)

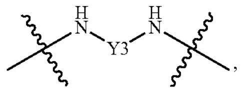

in which Y3 represents a ($C_1$-$C_{12}$)alkyl, aryl or polyalkylene glycol; and n'=0;

Z2 is a group represented by the following formula (IIb):

(IIb)

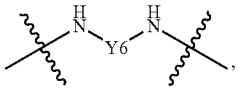

in which Y6 represents a $(C_1-C_{12})$alkyl, aryl, or polyalkylene glycol, and in which at least one of Y1 and Y3 is joined to a peptide residue via a functional residue, the functional residue and the peptide residue optionally being separated by a spacer fragment.

4. The polymer compound as claimed in claim 1, in which the peptide residue is a residue of the peptide Arg-Phe-Arg-Phe-Arg-Phe-Arg-Phe, Phe-Arg-Phe-Arg-Phe-Arg-Phe-Arg, or Arg-Arg-Palm, where Palm denotes a palmityl group.

5. The polymer compound as claimed in claim 1, said spacer fragment is of formula -(X1)-(X2)-(X3)-, in which X1 and X3 represent, each independently, —NH— or —CO—, and X2 represents a $(C_1-C_{12})$alkyl, aryl or a polyalkylene glycol.

6. A material comprising a polymer compound as defined in claim 1.

7. An article comprising a polymer compound as defined in claim 1.

* * * * *